US012774464B2

(12) United States Patent
Shao et al.

(10) Patent No.: US 12,774,464 B2
(45) Date of Patent: Oct. 27, 2026

(54) COMPOSITIONS AND METHODS FOR INHIBITING EXPRESSION OF METHYLATION-CONTROLLED J-PROTEIN (MCJ)

(71) Applicants: Mitotherapeutix LLC, Cheshire, CT (US); University of Vermont and State Agricultural College, Burlington, VT (US)

(72) Inventors: Pengcheng Patrick Shao, Fanwood, NJ (US); Mercedes Rincon, Aurora, CO (US)

(73) Assignees: Mitotherapeutix LLC, Cheshire, CT (US); University of Vermont and State Agricultural College, Burlington, VT (US)

(*) Notice: Subject to any disclaimer, the term of this patent is extended or adjusted under 35 U.S.C. 154(b) by 1040 days.

(21) Appl. No.: 17/801,095

(22) PCT Filed: Feb. 20, 2021

(86) PCT No.: PCT/US2021/018933

§ 371 (c)(1),
(2) Date: Aug. 19, 2022

(87) PCT Pub. No.: WO2021/168373

PCT Pub. Date: Aug. 26, 2021

(65) Prior Publication Data

US 2023/0092615 A1 Mar. 23, 2023

Related U.S. Application Data

(60) Provisional application No. 62/979,833, filed on Feb. 21, 2020.

(51) Int. Cl.
*C12N 15/113* (2010.01)
*A61K 31/713* (2006.01)

(52) U.S. Cl.
CPC .......... *C12N 15/113* (2013.01); *A61K 31/713* (2013.01); *C12N 2310/14* (2013.01); *C12N 2310/315* (2013.01); *C12N 2310/351* (2013.01)

(58) Field of Classification Search
CPC .............. C12N 15/113; C12N 2310/14; C12N 2310/315; C12N 2310/351; A61K 31/713
See application file for complete search history.

(56) References Cited

U.S. PATENT DOCUMENTS

| | | | | |
|---|---|---|---|---|
| 10,583,169 B2 * | 3/2020 | Rincon | .................. | A61K 38/17 |
| 10,655,126 B2 * | 5/2020 | Rincon | ................... | A61P 39/02 |
| 11,752,193 B2 * | 9/2023 | Rincon | .................. | A61K 45/06 424/139.1 |
| 2006/0275794 A1 * | 12/2006 | Carrino | ................ | C12Q 1/6876 435/6.1 |
| 2014/0288158 A1 * | 9/2014 | Rajeev | ................... | A61K 48/00 536/24.5 |
| 2023/0190785 A1 * | 6/2023 | Tremblay | ........... | A61K 31/7125 514/44 R |

FOREIGN PATENT DOCUMENTS

| | | | | |
|---|---|---|---|---|
| RU | 2644675 C1 * | 2/2018 | ........... | C12N 15/113 |
| WO | 2017011356 A2 | 1/2017 | | |
| WO | 2020191183 A1 | 9/2020 | | |

OTHER PUBLICATIONS

Watts, Jonathan K., et al. “Chemically Modified siRNA: Tools and Applications.” Drug Discovery Today, vol. 13, Nos. 19-20, Oct. 2008, pp. 842-855. (Year: 2008).*

Zhu, Lin, and Ram I. Mahato. “Targeted Delivery of siRNA to Hepatocytes and Hepatic Stellate Cells by Bioconjugation.” Bioconjugate Chemistry, vol. 21, No. 11, Nov. 2010, pp. 2119-2127. (Year: 2010).*

Eckstein, Fritz. “Phosphorothioates, Essential Components of Therapeutic Oligonucleotides.” Nucleic Acid Therapeutics, vol. 24, No. 6, Dec. 2014, pp. 374-387. (Year: 2014).*

Fakhr, E, et al. “Precise and Efficient siRNA Design: A Key Point in Competent Gene Silencing.” Cancer Gene Therapy, vol. 23, No. 4, Apr. 2016, pp. 73-82. (Year: 2016).*

International Search Report and Written Opinion from the International Searching Authority dated Jun. 9, 2021 from corresponding International Patent Application No. PCT/US2021 /018933 Filed on Feb. 20, 2021.

* cited by examiner

*Primary Examiner* — J. E. Angell
*Assistant Examiner* — Sarah E Allen
(74) *Attorney, Agent, or Firm* — Pierce Atwood LLP; Christopher A. Baxter

(57) ABSTRACT

Compositions and methods useful to reduce expression of methylation-controlled J-protein (MCJ) gene and for treatment of MCJ-associated diseases and conditions are provided. Provided are MCJ dsRNA agents, MCJ antisense polynucleotide agents, compositions comprising MCJ dsRNA agents, and, compositions comprising MCJ antisense polynucleotide agents that can be used to reduce MCJ expression in cells and subjects.

15 Claims, No Drawings

Specification includes a Sequence Listing.

SEQUENCE LISTING

<160> NUMBER OF SEQ ID NOS: 306

<210> SEQ ID NO 1
<211> LENGTH: 150
<212> TYPE: PRT
<213> ORGANISM: Homo sapiens

<400> SEQUENCE: 1

Met Ala Ala Arg Gly Val Ile Ala Pro Val Gly Glu Ser Leu Arg Tyr
1 5 10 15

Ala Glu Tyr Leu Gln Pro Ser Ala Lys Arg Pro Asp Ala Asp Val Asp
20 25 30

Gln Gln Arg Leu Val Arg Ser Leu Ile Ala Val Gly Leu Gly Val Ala
35 40 45

Ala Leu Ala Phe Ala Gly Arg Tyr Ala Phe Arg Ile Trp Lys Pro Leu
50 55 60

Glu Gln Val Ile Thr Glu Thr Ala Lys Lys Ile Ser Thr Pro Ser Phe
65 70 75 80

Ser Ser Tyr Tyr Lys Gly Gly Phe Glu Gln Lys Met Ser Arg Arg Glu
85 90 95

Ala Gly Leu Ile Leu Gly Val Ser Pro Ser Ala Gly Lys Ala Lys Ile
100 105 110

Arg Thr Ala His Arg Arg Val Met Ile Leu Asn His Pro Asp Lys Gly
115 120 125

Gly Ser Pro Tyr Val Ala Ala Lys Ile Asn Glu Ala Lys Asp Leu Leu
130 135 140

Glu Thr Thr Thr Lys His
145 150

<210> SEQ ID NO 2
<211> LENGTH: 2792
<212> TYPE: DNA
<213> ORGANISM: Homo sapiens

<400> SEQUENCE: 2
caccctcagg cactacagct agactccgag cttactgggc agtcatctga ttcgaccaac 60
atcagttcgc agggcttaag cccagtccct tacggcggcc tggggaggga ccaggcccaa 120
gtatataaag ctccctgagg gtccgcgttg gctttgcgcc tgtgagtgtg attcaagaac 180
gtcccagtgc ccttggctcc tttcggagtg tgaccccgtg cttgcacggg acacgttacc 240
cagctcgggt gagaagggta tcttccggga acctcgcctt taatagcaca acgagcgcag 300
agtccactgg atctgcgaga agaaaccgcg ctaactagtt tgtccctacg gccgcctcgt 360
agtcactgcc gcggcgcctt gagtctccgg gccgccttgc catggctgcc cgtggtgtca 420
tcgctccagt tggcgagagt ttgcgctacg ctgagtactt gcagccctcg gccaaacggc 480
cagacgccga cgtcgaccag cagagactgg taagaagttt gatagctgta ggactgggtg 540
ttgcagctct tgcatttgca ggtcgctacg catttcggat ctggaaacct ctagaacaag 600
ttatcacaga aactgcaaag aagatttcaa ctcctagctt ttcatcctac tataaaggag 660
gatttgaaca gaaaatgagt aggcgagaag ctggtcttat tttaggtgta agcccatctg 720
ctggcaaggc taagattaga acagctcata ggagagtcat gattttgaat cacccagata 780
aaggtggatc tccttacgta gcagccaaaa taaatgaagc aaaagacttg ctagaaacaa 840
ccaccaaaca ttgatgctta aggaccacac tgaaggaaaa aaaaagaggg gacttcgaaa 900
aaaaaaaaag ccctgcaaaa tattctaaaa catggtcttc ttaattttct atatggattg 960

-continued

```
accacagtct tatcttccac cattaagctg tataacaata aaatgttaat agtcttgctt   1020

tttattatct tttaaagatc tccttaaatt ctataactga tcttttttct tattttgttt   1080

gtgacattca tacattttta agatttttgt tatgttctga attccccccct acacacacac   1140

acacacacac acacacacac acgtgcaaaa aatatgatca agaatgcaat tgggatttgt   1200

gagcaatgag tagacctctt attgtttata tttgtaccct cattgtcaat tttttttttag   1260

ggaatttggg actctgccta tataaggtgt tttaaatgtc ttgagaacaa gcactggctg   1320

atacctcttg gagatatgat ctgaaatgta atggaattta ttaaatggtg tttagtaaag   1380

taggggttaa ggacttgtta aagaacccca ctatctctga gaccctatag ccaaagcatg   1440

aggacttgga gagctactaa aatgattcag gtttacaaaa tgagccctgt gaggaaaggt   1500

tgagagaagt ctgaggagtt tgtatttaat tatagtcttc cagtactgta tattcattca   1560

ttactcattc tacaaatatt tattgacccc ttttgatgtg caaggcacta tcgtgcgtcc   1620

cctgagagtt gcaagtatga agcagtcatg gatcatgaac caaaggaact tatatgtaga   1680

ggaaggataa atcacaaata gtgaatactg ttagatacag atgatatatt ttaaaagttc   1740

aaaggaagaa aagaatgtgt taaacactgc atgagaggag gaataagtgg catagagcta   1800

ggctttagaa aagaaaaata ttccgatacc atatgattgg tgaggtaagt gttattctga   1860

gatgagaatt agcagaaata gatatatcaa tcggagtgat tagagtgcag ggtttctgga   1920

aagcaaggtt tggacagagt ggtcatcaaa ggccagccct gtgacttaca ctgcattaaa   1980

ttaatttctt agaacatagt ccctgatcat tatcacttta ctattccaaa ggtgagagaa   2040

cagattcaga tagagtgcca gcattgtttc ccagtattcc tttacaaatc ttgggttcat   2100

tccaggtaaa ctgaactact gcattgtttc tatcttaaaa tactttttag atatcctaga   2160

tgcatctttc aacttctaac attctgtagt ttaggagttc tcaaccttgg cattattgac   2220

atgttaggcc aaataatttt ttttgtggga ggtctcttgt gcgttttaga tgattagcaa   2280

taatccctga cctgttatct actaaagact agtcgtttct catcagttgt gacaacaaaa   2340

atggttccag atattgccaa atgcccttta gaggacagta atcgccccca gttgagaacc   2400

atttcagtaa aactttaatt actatttttt cttttggttt ataaaataat gatcctgaat   2460

taaattgatg gaaccttgaa gtcgataaaa tatatttctt gctttaaagt ccccatacgt   2520

gtcctactaa ttttctcatg ctttagtgtt ttcacttttc tcctgttatc cttgtaccta   2580

agaatgccat cccaatcccc agatgtccac ctgcccaaag tctaggcata gctgaaggcc   2640

aagctaaaat gtatccctct ttttctggta catgcagcaa aagtaatatg aattatcagc   2700

tttctgagag caggcattgt atctgtcttg tttggtgtta cattggcacc caataaatat   2760

ttgttgagtg aatgaaaaaa aaaaaaaaaa aa                                 2792
```

```
<210> SEQ ID NO 3
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 3

agacgccgac gucgaccaan n                                              21


<210> SEQ ID NO 4
```

<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 4
uuggucgacg ucggcgucun n 21

<210> SEQ ID NO 5
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 5
agcuguagga cuggguguan n 21

<210> SEQ ID NO 6
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 6
uacacccagu ccuacagcun n 21

<210> SEQ ID NO 7
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 7
cuguaggacu ggguguugan n 21

<210> SEQ ID NO 8
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 8
ucaacaccca guccuacagn n 21

<210> SEQ ID NO 9
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 9
uguaggacug gguguugcan n 21

<210> SEQ ID NO 10
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 10
ugcaacaccc aguccuacan n 21

<210> SEQ ID NO 11
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 11
guaggacugg guguugcaan n 21

<210> SEQ ID NO 12
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 12
uugcaacacc caguccuacn n 21

<210> SEQ ID NO 13
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 13
gguguugcag cucuugcaan n 21

<210> SEQ ID NO 14
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 14
uugcaagagc ugcaacaccn n 21

<210> SEQ ID NO 15
<211> LENGTH: 21
<212> TYPE: RNA
<213> ORGANISM: Synthetic oligonucleotide
<220> FEATURE:

-continued

<221> NAME/KEY: misc_feature
<222> LOCATION: (20)..(21)
<223> OTHER INFORMATION: n is 2'-deoxythymidine-3'-phosphate

<400> SEQUENCE: 15
ugcagcucuu gcauuugcan n 21

<210> SEQ ID NO 16
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 16
ugcaaaugca agagcugcan n 21

<210> SEQ ID NO 17
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 17
agcucuugca uuugcaggan n 21

<210> SEQ ID NO 18
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 18
uccugcaaau gcaagagcun n 21

<210> SEQ ID NO 19
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 19
gcucuugcau uugcagguan n 21

<210> SEQ ID NO 20
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 20
uaccugcaaa ugcaagagcn n 21

<210> SEQ ID NO 21
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 21
ugcauuugca ggucgcuaan n 21

<210> SEQ ID NO 22
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 22
uuagcgaccu gcaaaugcan n 21

<210> SEQ ID NO 23
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 23
gcauuugcag gucgcuacan n 21

<210> SEQ ID NO 24
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 24
uguagcgacc ugcaaaugcn n 21

<210> SEQ ID NO 25
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 25
uuugcagguc gcuacgcaan n 21

<210> SEQ ID NO 26
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 26
uugcguagcg accugcaaan n 21

<210> SEQ ID NO 27
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 27
uugcaggucg cuacgcauan n 21

<210> SEQ ID NO 28
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 28
uaugcguagc gaccugcaan n 21

<210> SEQ ID NO 29
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 29
ugcaggucgc uacgcauuan n 21

<210> SEQ ID NO 30
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 30
uaaugcguag cgaccugcan n 21

<210> SEQ ID NO 31
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 31
gcaggucgcu acgcauuuan n 21

<210> SEQ ID NO 32
<211> LENGTH: 21
<212> TYPE: RNA
<213> ORGANISM: Synthetic oligonucleotide -continued
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 32
uaaaugcgua gcgaccugcn n 21

<210> SEQ ID NO 33
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 33
caggucgcua cgcauuucan n 21

<210> SEQ ID NO 34
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 34
ugaaaugcgu agcgaccugn n 21

<210> SEQ ID NO 35
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 35
gcauuucgga ucuggaaaan n 21

<210> SEQ ID NO 36
<211> LENGTH: 19
<212> TYPE: RNA
<213> ORGANISM: Synthetic oligonucleotide
<220> FEATURE:
<221> NAME/KEY: misc_feature
<222> LOCATION: (18)..(19)
<223> OTHER INFORMATION: n is 2'-deoxythymidine-3'-phosphate

<400> SEQUENCE: 36
uuuuccagau ccgaaaugc 19

<210> SEQ ID NO 37
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 37
cauuucggau cuggaaacan n 21

-continued

<210> SEQ ID NO 38
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 38
uguuuccaga uccgaaaugn n 21

<210> SEQ ID NO 39
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 39
aucuggaaac cucuagaaan n 21

<210> SEQ ID NO 40
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 40
uuucuagagg uuuccagaun n 21

<210> SEQ ID NO 41
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 41
ucuggaaacc ucuagaacan n 21

<210> SEQ ID NO 42
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 42
uguucuagag guuuccagan n 21

<210> SEQ ID NO 43
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 43
ccucuagaac aaguuaucan n 21

<210> SEQ ID NO 44
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 44
ugauaacuug uucuagaggn n 21

<210> SEQ ID NO 45
<211> LENGTH: 19
<212> TYPE: RNA
<213> ORGANISM: Synthetic oligonucleotide
<220> FEATURE:
<221> NAME/KEY: misc_feature
<222> LOCATION: (18)..(19)
<223> OTHER INFORMATION: n is 2'-deoxythymidine-3'-phosphate

<400> SEQUENCE: 45
uccuagcuuu ucauccuaa 19

<210> SEQ ID NO 46
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 46
uuaggaugaa aagcuaggan n 21

<210> SEQ ID NO 47
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 47
uagcuuuuca uccuacuaan n 21

<210> SEQ ID NO 48
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 48
uuaguaggau gaaaagcuan n 21

<210> SEQ ID NO 49
<211> LENGTH: 21
<212> TYPE: RNA

<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 49
agcuuuucau ccuacuauan n 21

<210> SEQ ID NO 50
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 50
uauaguagga ugaaaagcun n 21

<210> SEQ ID NO 51
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 51
gcuuuucauc cuacuauaan n 21

<210> SEQ ID NO 52
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 52
uuauaguagg augaaaagcn n 21

<210> SEQ ID NO 53
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 53
uucauccuac uauaaaggan n 21

<210> SEQ ID NO 54
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 54
uccuuuauag uaggaugaan n 21

<210> SEQ ID NO 55
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 55
ucauccuacu auaaaggaan n 21

<210> SEQ ID NO 56
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 56
uuccuuuaua guaggaugan n 21

<210> SEQ ID NO 57
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 57
cauccuacua uaaaggagan n 21

<210> SEQ ID NO 58
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 58
ucuccuuuau aguaggaugn n 21

<210> SEQ ID NO 59
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 59
cagaaaauga guaggcgaan n 21

<210> SEQ ID NO 60
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)

<223> OTHER INFORMATION: n is 2'-deoxythymidine-3'-phosphate

<400> SEQUENCE: 60
uucgccuacu cauuuucugn n 21

<210> SEQ ID NO 61
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 61
gcuggucuua uuuuaggUan n 21

<210> SEQ ID NO 62
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 62
uaccuaaaau aagaccagcn n 21

<210> SEQ ID NO 63
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 63
cuggucuuau uuuaggugan n 21

<210> SEQ ID NO 64
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 64
ucaccuaaaa uaagaccagn n 21

<210> SEQ ID NO 65
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 65
uggucuuauu uuagguguan n 21

<210> SEQ ID NO 66
<211> LENGTH: 21

<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 66
uacaccuaaa auaagaccan n 21

<210> SEQ ID NO 67
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 67
uuuuaggugu aagcccauan n 21

<210> SEQ ID NO 68
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 68
uaugggcuua caccuaaaan n 21

<210> SEQ ID NO 69
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 69
uuagguguaa gcccaucuan n 21

<210> SEQ ID NO 70
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 70
uagaugggcu uacaccuaan n 21

<210> SEQ ID NO 71
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 71
agguguaagc ccaucugcan n 21

<210> SEQ ID NO 72
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 72
ugcagauggg cuuacaccun n 21

<210> SEQ ID NO 73
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 73
agcccaucug cuggcaagan n 21

<210> SEQ ID NO 74
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 74
ucuugccagc agaugggcun n 21

<210> SEQ ID NO 75
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 75
caucugcugg caaggcuaan n 21

<210> SEQ ID NO 76
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 76
uuagccuugc cagcagaugn n 21

<210> SEQ ID NO 77
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 77
aucugcuggc aaggcuaaan n 21

<210> SEQ ID NO 78
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 78
uuuagccuug ccagcagaun n 21

<210> SEQ ID NO 79
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 79
ucugcuggca aggcuaagan n 21

<210> SEQ ID NO 80
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 80
ucuuagccuu gccagcagan n 21

<210> SEQ ID NO 81
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 81
cugcuggcaa ggcuaagaan n 21

<210> SEQ ID NO 82
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 82
uucuuagccu ugccagcagn n 21

<210> SEQ ID NO 83

<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 83
gcuggcaagg cuaagauuan n 21

<210> SEQ ID NO 84
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 84
uaaucuuagc cuugccagcn n 21

<210> SEQ ID NO 85
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 85
cuggcaaggc uaagauuaan n 21

<210> SEQ ID NO 86
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 86
uuaaucuuag ccuugccagn n 21

<210> SEQ ID NO 87
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 87
uggcaaggcu aagauuagan n 21

<210> SEQ ID NO 88
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 88
ucuaaucuua gccuugccan n 21

<210> SEQ ID NO 89
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 89
ggcaaggcua agauuagaan n 21

<210> SEQ ID NO 90
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 90
uucuaaucuu agccuugccn n 21

<210> SEQ ID NO 91
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 91
caaggcuaag auuagaacan n 21

<210> SEQ ID NO 92
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 92
uguucuaauc uuagccuugn n 21

<210> SEQ ID NO 93
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 93
ggcuaagauu agaacagcan n 21

<210> SEQ ID NO 94
<211> LENGTH: 21
<212> TYPE: RNA
<213> ORGANISM: Synthetic oligonucleotide
<220> FEATURE:

<221> NAME/KEY: misc_feature
<222> LOCATION: (20)..(21)
<223> OTHER INFORMATION: n is 2'-deoxythymidine-3'-phosphate

<400> SEQUENCE: 94
ugcuguucua aucuuagccn n 21

<210> SEQ ID NO 95
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 95
cccagauaaa gguggaucan n 21

<210> SEQ ID NO 96
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 96
ugauccaccu uuaucugggn n 21

<210> SEQ ID NO 97
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 97
ccagauaaag guggaucuan n 21

<210> SEQ ID NO 98
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 98
uagauccacc uuuaucuggn n 21

<210> SEQ ID NO 99
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 99
cagauaaagg uggaucucan n 21

<210> SEQ ID NO 100
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 100
ugagauccac cuuuaucugn n 21

<210> SEQ ID NO 101
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 101
aaagguggau cuccuuacan n 21

<210> SEQ ID NO 102
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 102
uguaaggaga uccaccuuun n 21

<210> SEQ ID NO 103
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 103
aagguggauc uccuuacgan n 21

<210> SEQ ID NO 104
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 104
ucguaaggag auccaccuun n 21

<210> SEQ ID NO 105
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 105
agguggaucu ccuuacguan n 21

<210> SEQ ID NO 106
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 106
uacguaagga gauccaccun n 21

<210> SEQ ID NO 107
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 107
gguggaucuc cuuacguaan n 21

<210> SEQ ID NO 108
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 108
uuacguaagg agauccaccn n 21

<210> SEQ ID NO 109
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 109
guggaucucc uuacguagan n 21

<210> SEQ ID NO 110
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 110
ucuacguaag gagauccacn n 21

<210> SEQ ID NO 111
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 111
uggaucuccu uacguagcan n 21

<210> SEQ ID NO 112
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 112
ugcuacguaa ggagauccan n 21

<210> SEQ ID NO 113
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 113
augaagcaaa agacuugcan n 21

<210> SEQ ID NO 114
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 114
ugcaagucuu uugcuucaun n 21

<210> SEQ ID NO 115
<211> LENGTH: 19
<212> TYPE: RNA
<213> ORGANISM: Homo sapiens

<400> SEQUENCE: 115
agacgccgac gucgaccag 19

<210> SEQ ID NO 116
<211> LENGTH: 19
<212> TYPE: RNA
<213> ORGANISM: Homo sapiens

<400> SEQUENCE: 116
agcuguagga cugggugu 19

<210> SEQ ID NO 117
<211> LENGTH: 19
<212> TYPE: RNA
<213> ORGANISM: Homo sapiens

<400> SEQUENCE: 117
cuguaggacu ggguguugc 19

<210> SEQ ID NO 118
<211> LENGTH: 19
<212> TYPE: RNA
<213> ORGANISM: Homo sapiens

<400> SEQUENCE: 118
uguaggacug gguguugca 19

<210> SEQ ID NO 119
<211> LENGTH: 19
<212> TYPE: RNA
<213> ORGANISM: Homo sapiens

<400> SEQUENCE: 119
guaggacugg guguugcag 19

<210> SEQ ID NO 120
<211> LENGTH: 19
<212> TYPE: RNA
<213> ORGANISM: Homo sapiens

<400> SEQUENCE: 120
gguguugcag cucuugcau 19

<210> SEQ ID NO 121
<211> LENGTH: 19
<212> TYPE: RNA
<213> ORGANISM: Homo sapiens

<400> SEQUENCE: 121
ugcagcucuu gcauuugca 19

<210> SEQ ID NO 122
<211> LENGTH: 19
<212> TYPE: RNA
<213> ORGANISM: Homo sapiens

<400> SEQUENCE: 122
agcucuugca uuugcaggu 19

<210> SEQ ID NO 123
<211> LENGTH: 19
<212> TYPE: RNA
<213> ORGANISM: Homo sapiens

<400> SEQUENCE: 123
gcucuugcau uugcagguc 19

<210> SEQ ID NO 124
<211> LENGTH: 19
<212> TYPE: RNA
<213> ORGANISM: Homo sapiens

<400> SEQUENCE: 124
ugcauuugca ggucgcuac 19

<210> SEQ ID NO 125
<211> LENGTH: 19
<212> TYPE: RNA
<213> ORGANISM: Homo sapiens

<400> SEQUENCE: 125
gcauuugcag gucgcuacg 19

<210> SEQ ID NO 126
<211> LENGTH: 19
<212> TYPE: RNA
<213> ORGANISM: Homo sapiens

<400> SEQUENCE: 126
uuugcagguc gcuacgcau 19

<210> SEQ ID NO 127
<211> LENGTH: 19
<212> TYPE: RNA
<213> ORGANISM: Homo sapiens

<400> SEQUENCE: 127
uugcaggucg cuacgcauu 19

<210> SEQ ID NO 128
<211> LENGTH: 19
<212> TYPE: RNA
<213> ORGANISM: Homo sapiens

<400> SEQUENCE: 128
ugcaggucgc uacgcauuu 19

<210> SEQ ID NO 129
<211> LENGTH: 19
<212> TYPE: RNA
<213> ORGANISM: Homo sapiens

<400> SEQUENCE: 129
gcaggucgcu acgcauuuc 19

<210> SEQ ID NO 130
<211> LENGTH: 19
<212> TYPE: RNA
<213> ORGANISM: Homo sapiens

<400> SEQUENCE: 130
caggucgcua cgcauuucg 19

<210> SEQ ID NO 131
<211> LENGTH: 19
<212> TYPE: RNA
<213> ORGANISM: Homo sapiens

<400> SEQUENCE: 131
gcauuucgga ucuggaaac 19

<210> SEQ ID NO 132
<211> LENGTH: 19
<212> TYPE: RNA
<213> ORGANISM: Homo sapiens

<400> SEQUENCE: 132
cauuucggau cuggaaacc 19

<210> SEQ ID NO 133
<211> LENGTH: 19
<212> TYPE: RNA
<213> ORGANISM: Homo sapiens

<400> SEQUENCE: 133
aucuggaaac cucuagaac 19

<210> SEQ ID NO 134
<211> LENGTH: 19
<212> TYPE: RNA
<213> ORGANISM: Homo sapiens

<400> SEQUENCE: 134
ucuggaaacc ucuagaaca 19

<210> SEQ ID NO 135
<211> LENGTH: 19
<212> TYPE: RNA
<213> ORGANISM: Homo sapiens

<400> SEQUENCE: 135
ccucuagaac aaguuauca 19

<210> SEQ ID NO 136
<211> LENGTH: 19
<212> TYPE: RNA
<213> ORGANISM: Homo sapiens

<400> SEQUENCE: 136
uccuagcuuu ucauccuac 19

<210> SEQ ID NO 137
<211> LENGTH: 19
<212> TYPE: RNA
<213> ORGANISM: Homo sapiens

<400> SEQUENCE: 137
uagcuuuuca uccuacuau 19

<210> SEQ ID NO 138
<211> LENGTH: 19
<212> TYPE: RNA
<213> ORGANISM: Homo sapiens

<400> SEQUENCE: 138
agcuuuucau ccuacuaua 19

<210> SEQ ID NO 139
<211> LENGTH: 19
<212> TYPE: RNA
<213> ORGANISM: Homo sapiens

<400> SEQUENCE: 139
gcuuuucauc cuacuauaa 19

<210> SEQ ID NO 140
<211> LENGTH: 19
<212> TYPE: RNA
<213> ORGANISM: Homo sapiens

<400> SEQUENCE: 140
uucauccuac uauaaagga 19

<210> SEQ ID NO 141
<211> LENGTH: 19
<212> TYPE: RNA
<213> ORGANISM: Homo sapiens

<400> SEQUENCE: 141
ucauccuacu auaaaggag 19

<210> SEQ ID NO 142
<211> LENGTH: 19
<212> TYPE: RNA
<213> ORGANISM: Homo sapiens

<400> SEQUENCE: 142
cauccuacua uaaaggagg 19

<210> SEQ ID NO 143
<211> LENGTH: 19
<212> TYPE: RNA
<213> ORGANISM: Homo sapiens

<400> SEQUENCE: 143
cagaaaauga guaggcgag 19

<210> SEQ ID NO 144
<211> LENGTH: 19
<212> TYPE: RNA
<213> ORGANISM: Homo sapiens

<400> SEQUENCE: 144
gcuggucuua uuuuaggug 19

<210> SEQ ID NO 145
<211> LENGTH: 19
<212> TYPE: RNA
<213> ORGANISM: Homo sapiens

<400> SEQUENCE: 145
cuggucuuau uuuaggugu 19

<210> SEQ ID NO 146
<211> LENGTH: 19
<212> TYPE: RNA
<213> ORGANISM: Homo sapiens

<400> SEQUENCE: 146
uggucuuauu uuaggugua 19

<210> SEQ ID NO 147
<211> LENGTH: 19
<212> TYPE: RNA
<213> ORGANISM: Homo sapiens

<400> SEQUENCE: 147
uuuuaggugu aagcccauc 19

<210> SEQ ID NO 148
<211> LENGTH: 19
<212> TYPE: RNA
<213> ORGANISM: Homo sapiens

<400> SEQUENCE: 148
uuagguguaa gcccaucug 19

<210> SEQ ID NO 149
<211> LENGTH: 19
<212> TYPE: RNA

<213> ORGANISM: Homo sapiens

<400> SEQUENCE: 149
agguguaagc ccaucugcu 19

<210> SEQ ID NO 150
<211> LENGTH: 19
<212> TYPE: RNA
<213> ORGANISM: Homo sapiens

<400> SEQUENCE: 150
agcccaucug cuggcaagg 19

<210> SEQ ID NO 151
<211> LENGTH: 19
<212> TYPE: RNA
<213> ORGANISM: Homo sapiens

<400> SEQUENCE: 151
caucugcugg caaggcuaa 19

<210> SEQ ID NO 152
<211> LENGTH: 19
<212> TYPE: RNA
<213> ORGANISM: Homo sapiens

<400> SEQUENCE: 152
aucugcuggc aaggcuaag 19

<210> SEQ ID NO 153
<211> LENGTH: 19
<212> TYPE: RNA
<213> ORGANISM: Homo sapiens

<400> SEQUENCE: 153
ucugcuggca aggcuaaga 19

<210> SEQ ID NO 154
<211> LENGTH: 19
<212> TYPE: RNA
<213> ORGANISM: Homo sapiens

<400> SEQUENCE: 154
cugcuggcaa ggcuaagau 19

<210> SEQ ID NO 155
<211> LENGTH: 19
<212> TYPE: RNA
<213> ORGANISM: Homo sapiens

<400> SEQUENCE: 155
gcuggcaagg cuaagauua 19

<210> SEQ ID NO 156
<211> LENGTH: 19
<212> TYPE: RNA
<213> ORGANISM: Homo sapiens

<400> SEQUENCE: 156
cuggcaaggc uaagauuag 19

<210> SEQ ID NO 157
<211> LENGTH: 19

-continued

<212> TYPE: RNA
<213> ORGANISM: Homo sapiens

<400> SEQUENCE: 157
uggcaaggcu aagauuaga 19

<210> SEQ ID NO 158
<211> LENGTH: 19
<212> TYPE: RNA
<213> ORGANISM: Homo sapiens

<400> SEQUENCE: 158
ggcaaggcua agauuagaa 19

<210> SEQ ID NO 159
<211> LENGTH: 19
<212> TYPE: RNA
<213> ORGANISM: Homo sapiens

<400> SEQUENCE: 159
caaggcuaag auuagaaca 19

<210> SEQ ID NO 160
<211> LENGTH: 19
<212> TYPE: RNA
<213> ORGANISM: Homo sapiens

<400> SEQUENCE: 160
ggcuaagauu agaacagcu 19

<210> SEQ ID NO 161
<211> LENGTH: 19
<212> TYPE: RNA
<213> ORGANISM: Homo sapiens

<400> SEQUENCE: 161
cccagauaaa gguggaucu 19

<210> SEQ ID NO 162
<211> LENGTH: 19
<212> TYPE: RNA
<213> ORGANISM: Homo sapiens

<400> SEQUENCE: 162
ccagauaaag guggaucuc 19

<210> SEQ ID NO 163
<211> LENGTH: 19
<212> TYPE: RNA
<213> ORGANISM: Homo sapiens

<400> SEQUENCE: 163
cagauaaagg uggaucucc 19

<210> SEQ ID NO 164
<211> LENGTH: 19
<212> TYPE: RNA
<213> ORGANISM: Homo sapiens

<400> SEQUENCE: 164
aaagguggau cuccuuacg 19

<210> SEQ ID NO 165

<211> LENGTH: 19
<212> TYPE: RNA
<213> ORGANISM: Homo sapiens

<400> SEQUENCE: 165
aagguggauc uccuuacgu 19

<210> SEQ ID NO 166
<211> LENGTH: 19
<212> TYPE: RNA
<213> ORGANISM: Homo sapiens

<400> SEQUENCE: 166
agguggaucu ccuuacgua 19

<210> SEQ ID NO 167
<211> LENGTH: 19
<212> TYPE: RNA
<213> ORGANISM: Homo sapiens

<400> SEQUENCE: 167
gguggaucuc cuuacguag 19

<210> SEQ ID NO 168
<211> LENGTH: 19
<212> TYPE: RNA
<213> ORGANISM: Homo sapiens

<400> SEQUENCE: 168
guggaucucc uuacguagc 19

<210> SEQ ID NO 169
<211> LENGTH: 19
<212> TYPE: RNA
<213> ORGANISM: Homo sapiens

<400> SEQUENCE: 169
uggaucuccu uacguagca 19

<210> SEQ ID NO 170
<211> LENGTH: 19
<212> TYPE: RNA
<213> ORGANISM: Homo sapiens

<400> SEQUENCE: 170
augaagcaaa agacuugcu 19

<210> SEQ ID NO 171
<211> LENGTH: 21
<212> TYPE: RNA
<213> ORGANISM: Synthetic oligonucleotide

<400> SEQUENCE: 171
acgcauuucg gaucuggaaa a 21

<210> SEQ ID NO 172
<211> LENGTH: 21
<212> TYPE: RNA
<213> ORGANISM: Synthetic oligonucleotide

<400> SEQUENCE: 172
uuuuccagau ccgaaaugcg u 21

<210> SEQ ID NO 173
<211> LENGTH: 21
<212> TYPE: RNA
<213> ORGANISM: Synthetic oligonucleotide

<400> SEQUENCE: 173
ggaucuggaa accucuagaa a 21

<210> SEQ ID NO 174
<211> LENGTH: 21
<212> TYPE: RNA
<213> ORGANISM: Synthetic oligonucleotide

<400> SEQUENCE: 174
uuucuagagg uuuccagauc c 21

<210> SEQ ID NO 175
<211> LENGTH: 21
<212> TYPE: RNA
<213> ORGANISM: Synthetic oligonucleotide

<400> SEQUENCE: 175
gaucuggaaa ccucuagaac a 21

<210> SEQ ID NO 176
<211> LENGTH: 21
<212> TYPE: RNA
<213> ORGANISM: Synthetic oligonucleotide

<400> SEQUENCE: 176
uguucuagag guuuccagau c 21

<210> SEQ ID NO 177
<211> LENGTH: 21
<212> TYPE: RNA
<213> ORGANISM: Synthetic oligonucleotide

<400> SEQUENCE: 177
aaccucuaga acaaguuauc a 21

<210> SEQ ID NO 178
<211> LENGTH: 21
<212> TYPE: RNA
<213> ORGANISM: Synthetic oligonucleotide

<400> SEQUENCE: 178
ugauaacuug uucuagaggu u 21

<210> SEQ ID NO 179
<211> LENGTH: 21
<212> TYPE: RNA
<213> ORGANISM: Synthetic oligonucleotide

<400> SEQUENCE: 179
gcuggucuua uuuuaggugu a 21

<210> SEQ ID NO 180
<211> LENGTH: 21
<212> TYPE: RNA
<213> ORGANISM: Synthetic oligonucleotide

<400> SEQUENCE: 180
uacaccuaaa auaagaccag c 21

<210> SEQ ID NO 181
<211> LENGTH: 21
<212> TYPE: RNA
<213> ORGANISM: Synthetic oligonucleotide

<400> SEQUENCE: 181
uuagguguaa gcccaucugc a 21

<210> SEQ ID NO 182
<211> LENGTH: 21
<212> TYPE: RNA
<213> ORGANISM: Synthetic oligonucleotide

<400> SEQUENCE: 182
ugcagauggg cuuacaccua a 21

<210> SEQ ID NO 183
<211> LENGTH: 21
<212> TYPE: RNA
<213> ORGANISM: Synthetic oligonucleotide

<400> SEQUENCE: 183
cccagauaaa gguggaucuc a 21

<210> SEQ ID NO 184
<211> LENGTH: 21
<212> TYPE: RNA
<213> ORGANISM: Synthetic oligonucleotide

<400> SEQUENCE: 184
ugagauccac cuuuaucugg g 21

<210> SEQ ID NO 185
<211> LENGTH: 21
<212> TYPE: RNA
<213> ORGANISM: Synthetic oligonucleotide

<400> SEQUENCE: 185
auaaaggugg aucuccuuac a 21

<210> SEQ ID NO 186
<211> LENGTH: 21
<212> TYPE: RNA
<213> ORGANISM: Synthetic oligonucleotide

<400> SEQUENCE: 186
uguaaggaga uccaccuuua u 21

<210> SEQ ID NO 187
<211> LENGTH: 21
<212> TYPE: RNA
<213> ORGANISM: Synthetic oligonucleotide

<400> SEQUENCE: 187
aaagguggau cuccuuacgu a 21

<210> SEQ ID NO 188
<211> LENGTH: 21
<212> TYPE: RNA
<213> ORGANISM: Synthetic oligonucleotide

<400> SEQUENCE: 188
uacguaagga gauccaccuu u 21

<210> SEQ ID NO 189
<211> LENGTH: 21
<212> TYPE: RNA
<213> ORGANISM: Synthetic oligonucleotide

<400> SEQUENCE: 189
aagguggauc uccuuacgua a 21

<210> SEQ ID NO 190
<211> LENGTH: 21
<212> TYPE: RNA
<213> ORGANISM: Synthetic oligonucleotide

<400> SEQUENCE: 190
uuacguaagg agauccaccu u 21

<210> SEQ ID NO 191
<211> LENGTH: 20
<212> TYPE: RNA
<213> ORGANISM: Synthetic oligonucleotide

<400> SEQUENCE: 191
gaucuggaaa ccucuagaaa 20

<210> SEQ ID NO 192
<211> LENGTH: 22
<212> TYPE: RNA
<213> ORGANISM: Synthetic oligonucleotide

<400> SEQUENCE: 192
uuucuagagg uuuccagauc uu 22

<210> SEQ ID NO 193
<211> LENGTH: 22
<212> TYPE: RNA
<213> ORGANISM: Synthetic oligonucleotide

<400> SEQUENCE: 193
gaucuggaaa ccucuagaaa uu 22

<210> SEQ ID NO 194
<211> LENGTH: 22
<212> TYPE: RNA
<213> ORGANISM: Synthetic oligonucleotide

<400> SEQUENCE: 194
uuucuagagg uuuccagauc uu 22

<210> SEQ ID NO 195
<211> LENGTH: 21
<212> TYPE: RNA
<213> ORGANISM: Synthetic oligonucleotide

<400> SEQUENCE: 195
ggaucuggaa accucuagaa a 21

<210> SEQ ID NO 196
<211> LENGTH: 21
<212> TYPE: RNA
<213> ORGANISM: Synthetic oligonucleotide

<400> SEQUENCE: 196
uuucuagagg uuuccagauc c 21

<210> SEQ ID NO 197
<211> LENGTH: 21
<212> TYPE: RNA
<213> ORGANISM: Synthetic oligonucleotide

<400> SEQUENCE: 197
ggaucuggaa accucuagaa a 21

<210> SEQ ID NO 198
<211> LENGTH: 21
<212> TYPE: RNA
<213> ORGANISM: Synthetic oligonucleotide

<400> SEQUENCE: 198
uuucuagagg uuuccagauc c 21

<210> SEQ ID NO 199
<211> LENGTH: 21
<212> TYPE: RNA
<213> ORGANISM: Synthetic oligonucleotide

<400> SEQUENCE: 199
ggaucuggaa accucuagaa a 21

<210> SEQ ID NO 200
<211> LENGTH: 21
<212> TYPE: RNA
<213> ORGANISM: Synthetic oligonucleotide

<400> SEQUENCE: 200
uuucuagagg uuuccagauc c 21

<210> SEQ ID NO 201
<211> LENGTH: 21
<212> TYPE: RNA
<213> ORGANISM: Synthetic oligonucleotide

<400> SEQUENCE: 201
ggaucuggaa accucuagaa a 21

<210> SEQ ID NO 202
<211> LENGTH: 21
<212> TYPE: RNA
<213> ORGANISM: Synthetic oligonucleotide

<400> SEQUENCE: 202
uuucuagagg uuuccagauc c 21

<210> SEQ ID NO 203
<211> LENGTH: 19
<212> TYPE: RNA
<213> ORGANISM: Synthetic oligonucleotide

<400> SEQUENCE: 203
ucuggaaacc ucuagaaca 19

<210> SEQ ID NO 204
<211> LENGTH: 21
<212> TYPE: RNA
<213> ORGANISM: Synthetic oligonucleotide

<400> SEQUENCE: 204
uguucuagag guuuccagau c 21

<210> SEQ ID NO 205
<211> LENGTH: 21
<212> TYPE: RNA
<213> ORGANISM: Synthetic oligonucleotide

<400> SEQUENCE: 205
gaucuggaaa ccucuagaac a 21

<210> SEQ ID NO 206
<211> LENGTH: 23
<212> TYPE: RNA
<213> ORGANISM: Synthetic oligonucleotide

<400> SEQUENCE: 206
uguucuagag guuuccagau cuu 23

<210> SEQ ID NO 207
<211> LENGTH: 21
<212> TYPE: RNA
<213> ORGANISM: Synthetic oligonucleotide

<400> SEQUENCE: 207
gaucuggaaa ccucuagaac a 21

<210> SEQ ID NO 208
<211> LENGTH: 21
<212> TYPE: RNA
<213> ORGANISM: Synthetic oligonucleotide

<400> SEQUENCE: 208
uguucuagag guuuccagaa c 21

<210> SEQ ID NO 209
<211> LENGTH: 21
<212> TYPE: RNA
<213> ORGANISM: Synthetic oligonucleotide

<400> SEQUENCE: 209
gaucuggaaa ccucuagaac a 21

<210> SEQ ID NO 210
<211> LENGTH: 21
<212> TYPE: RNA
<213> ORGANISM: Synthetic oligonucleotide

<400> SEQUENCE: 210
uguucuagag guuuccagaa c 21

<210> SEQ ID NO 211
<211> LENGTH: 21
<212> TYPE: RNA
<213> ORGANISM: Synthetic oligonucleotide

<400> SEQUENCE: 211
gaucuggaaa ccucuagaac a 21

<210> SEQ ID NO 212
<211> LENGTH: 21
<212> TYPE: RNA
<213> ORGANISM: Synthetic oligonucleotide

<400> SEQUENCE: 212
uguucuagag guuuccagaa c 21

<210> SEQ ID NO 213
<211> LENGTH: 21
<212> TYPE: RNA
<213> ORGANISM: Synthetic oligonucleotide

<400> SEQUENCE: 213
gaucuggaaa ccucuagaac a 21

<210> SEQ ID NO 214
<211> LENGTH: 21
<212> TYPE: RNA
<213> ORGANISM: Synthetic oligonucleotide

<400> SEQUENCE: 214
uguucuagag guuuccagaa c 21

<210> SEQ ID NO 215
<211> LENGTH: 21
<212> TYPE: RNA
<213> ORGANISM: Synthetic oligonucleotide

<400> SEQUENCE: 215
gaucuggaaa ccucuagaac a 21

<210> SEQ ID NO 216
<211> LENGTH: 23
<212> TYPE: RNA
<213> ORGANISM: Synthetic oligonucleotide

<400> SEQUENCE: 216
uguucuagag guuuccagau cuu 23

<210> SEQ ID NO 217
<211> LENGTH: 21
<212> TYPE: RNA
<213> ORGANISM: Synthetic oligonucleotide

<400> SEQUENCE: 217
gaucuggaaa ccucuagaac a 21

<210> SEQ ID NO 218
<211> LENGTH: 23
<212> TYPE: RNA
<213> ORGANISM: Synthetic oligonucleotide

<400> SEQUENCE: 218
uguucuagag guuuccagau ccg 23

<210> SEQ ID NO 219
<211> LENGTH: 21
<212> TYPE: RNA
<213> ORGANISM: Synthetic oligonucleotide

<400> SEQUENCE: 219
gaucuggaaa ccucuagaac a 21

<210> SEQ ID NO 220
<211> LENGTH: 21
<212> TYPE: RNA
<213> ORGANISM: Synthetic oligonucleotide

<400> SEQUENCE: 220
uguucuagag guuuccagau c 21

<210> SEQ ID NO 221
<211> LENGTH: 21
<212> TYPE: RNA
<213> ORGANISM: Synthetic oligonucleotide

<400> SEQUENCE: 221
gaucuggaaa ccucuagaac a 21

<210> SEQ ID NO 222
<211> LENGTH: 21
<212> TYPE: RNA
<213> ORGANISM: Synthetic oligonucleotide

<400> SEQUENCE: 222
uguucuagag guuuccagau c 21

<210> SEQ ID NO 223
<211> LENGTH: 21
<212> TYPE: RNA
<213> ORGANISM: Synthetic oligonucleotide

<400> SEQUENCE: 223
gaucuggaaa ccucuagaac a 21

<210> SEQ ID NO 224
<211> LENGTH: 21
<212> TYPE: RNA
<213> ORGANISM: Synthetic oligonucleotide

<400> SEQUENCE: 224
uguucuagag guuuccagau c 21

<210> SEQ ID NO 225
<211> LENGTH: 21
<212> TYPE: RNA
<213> ORGANISM: Synthetic oligonucleotide

<400> SEQUENCE: 225
gcucuggaaa ccucuagaac a 21

<210> SEQ ID NO 226
<211> LENGTH: 21
<212> TYPE: RNA
<213> ORGANISM: Synthetic oligonucleotide

<400> SEQUENCE: 226
uguucuagag guuuccagag c 21

<210> SEQ ID NO 227
<211> LENGTH: 20
<212> TYPE: RNA
<213> ORGANISM: Synthetic oligonucleotide

<400> SEQUENCE: 227
cucuggaaac cucuagaaca 20

<210> SEQ ID NO 228
<211> LENGTH: 20
<212> TYPE: RNA

<213> ORGANISM: Synthetic oligonucleotide

<400> SEQUENCE: 228
uguucuagag guuuccagag 20

<210> SEQ ID NO 229
<211> LENGTH: 21
<212> TYPE: RNA
<213> ORGANISM: Synthetic oligonucleotide

<400> SEQUENCE: 229
gaucuggaaa ccucuagaac a 21

<210> SEQ ID NO 230
<211> LENGTH: 23
<212> TYPE: RNA
<213> ORGANISM: Synthetic oligonucleotide

<400> SEQUENCE: 230
uguucuagag guuuccagau ccg 23

<210> SEQ ID NO 231
<211> LENGTH: 21
<212> TYPE: RNA
<213> ORGANISM: Synthetic oligonucleotide

<400> SEQUENCE: 231
gaucuggaaa ccucuagaac a 21

<210> SEQ ID NO 232
<211> LENGTH: 21
<212> TYPE: RNA
<213> ORGANISM: Synthetic oligonucleotide

<400> SEQUENCE: 232
uguucuagag guuuccagau c 21

<210> SEQ ID NO 233
<211> LENGTH: 21
<212> TYPE: RNA
<213> ORGANISM: Synthetic oligonucleotide

<400> SEQUENCE: 233
gcucuggaaa ccucuagaac a 21

<210> SEQ ID NO 234
<211> LENGTH: 21
<212> TYPE: RNA
<213> ORGANISM: Synthetic oligonucleotide

<400> SEQUENCE: 234
uguucuagag guuuccagag c 21

<210> SEQ ID NO 235
<211> LENGTH: 21
<212> TYPE: RNA
<213> ORGANISM: Synthetic oligonucleotide

<400> SEQUENCE: 235
cucuggaaac cucuagaaca a 21

<210> SEQ ID NO 236
<211> LENGTH: 21

-continued

<212> TYPE: RNA
<213> ORGANISM: Synthetic oligonucleotide

<400> SEQUENCE: 236
uuguucuaga gguuuccaga g 21

<210> SEQ ID NO 237
<211> LENGTH: 21
<212> TYPE: RNA
<213> ORGANISM: Synthetic oligonucleotide

<400> SEQUENCE: 237
cuggaaaccu cuagaacaag a 21

<210> SEQ ID NO 238
<211> LENGTH: 21
<212> TYPE: RNA
<213> ORGANISM: Synthetic oligonucleotide

<400> SEQUENCE: 238
ucuuguucua gagguuucca g 21

<210> SEQ ID NO 239
<211> LENGTH: 21
<212> TYPE: RNA
<213> ORGANISM: Synthetic oligonucleotide

<400> SEQUENCE: 239
uggaaaccuc uagaacaagu a 21

<210> SEQ ID NO 240
<211> LENGTH: 21
<212> TYPE: RNA
<213> ORGANISM: Synthetic oligonucleotide

<400> SEQUENCE: 240
uacuuguucu agagguuucc a 21

<210> SEQ ID NO 241
<211> LENGTH: 21
<212> TYPE: RNA
<213> ORGANISM: Synthetic oligonucleotide

<400> SEQUENCE: 241
ggaaaccucu agaacaaguu a 21

<210> SEQ ID NO 242
<211> LENGTH: 21
<212> TYPE: RNA
<213> ORGANISM: Synthetic oligonucleotide

<400> SEQUENCE: 242
uaacuuguuc uagagguuuc c 21

<210> SEQ ID NO 243
<211> LENGTH: 21
<212> TYPE: RNA
<213> ORGANISM: Synthetic oligonucleotide

<400> SEQUENCE: 243
gaaaccucua gaacaaguua a 21

<210> SEQ ID NO 244

-continued

<211> LENGTH: 21
<212> TYPE: RNA
<213> ORGANISM: Synthetic oligonucleotide

<400> SEQUENCE: 244
uuaacuuguu cuagagguuu c 21

<210> SEQ ID NO 245
<211> LENGTH: 21
<212> TYPE: RNA
<213> ORGANISM: Synthetic oligonucleotide

<400> SEQUENCE: 245
caaccucuag aacaaguuau a 21

<210> SEQ ID NO 246
<211> LENGTH: 21
<212> TYPE: RNA
<213> ORGANISM: Synthetic oligonucleotide

<400> SEQUENCE: 246
uauaacuugu ucuagagguu g 21

<210> SEQ ID NO 247
<211> LENGTH: 19
<212> TYPE: RNA
<213> ORGANISM: Synthetic oligonucleotide

<400> SEQUENCE: 247
ccucuagaac aaguuauca 19

<210> SEQ ID NO 248
<211> LENGTH: 21
<212> TYPE: RNA
<213> ORGANISM: Synthetic oligonucleotide

<400> SEQUENCE: 248
ugauaacuug uucuagaggu u 21

<210> SEQ ID NO 249
<211> LENGTH: 21
<212> TYPE: RNA
<213> ORGANISM: Synthetic oligonucleotide

<400> SEQUENCE: 249
caccucuaga acaaguuauc a 21

<210> SEQ ID NO 250
<211> LENGTH: 21
<212> TYPE: RNA
<213> ORGANISM: Synthetic oligonucleotide

<400> SEQUENCE: 250
ugauaacuug uucuagaggu g 21

<210> SEQ ID NO 251
<211> LENGTH: 21
<212> TYPE: RNA
<213> ORGANISM: Synthetic oligonucleotide

<400> SEQUENCE: 251
aaccucuaga acaaguuauc a 21

-continued

<210> SEQ ID NO 252
<211> LENGTH: 23
<212> TYPE: RNA
<213> ORGANISM: Synthetic oligonucleotide

<400> SEQUENCE: 252
ugauaacuug uucuagaggu uuc 23

<210> SEQ ID NO 253
<211> LENGTH: 21
<212> TYPE: RNA
<213> ORGANISM: Synthetic oligonucleotide

<400> SEQUENCE: 253
caccucuaga acaaguuauc a 21

<210> SEQ ID NO 254
<211> LENGTH: 21
<212> TYPE: RNA
<213> ORGANISM: Synthetic oligonucleotide

<400> SEQUENCE: 254
ugauaacuug uucuagaggu g 21

<210> SEQ ID NO 255
<211> LENGTH: 21
<212> TYPE: RNA
<213> ORGANISM: Synthetic oligonucleotide

<400> SEQUENCE: 255
caccucuaga acaaguuauc a 21

<210> SEQ ID NO 256
<211> LENGTH: 21
<212> TYPE: RNA
<213> ORGANISM: Synthetic oligonucleotide

<400> SEQUENCE: 256
ugauaacuug uucuagaggu g 21

<210> SEQ ID NO 257
<211> LENGTH: 21
<212> TYPE: RNA
<213> ORGANISM: Synthetic oligonucleotide

<400> SEQUENCE: 257
gaccucuaga acaaguuauc a 21

<210> SEQ ID NO 258
<211> LENGTH: 21
<212> TYPE: RNA
<213> ORGANISM: Synthetic oligonucleotide

<400> SEQUENCE: 258
ugauaacuug uucuagaggu c 21

<210> SEQ ID NO 259
<211> LENGTH: 21
<212> TYPE: RNA
<213> ORGANISM: Synthetic oligonucleotide

<400> SEQUENCE: 259
caccucuaga acaaguuauc a 21

<210> SEQ ID NO 260
<211> LENGTH: 21
<212> TYPE: RNA
<213> ORGANISM: Synthetic oligonucleotide

<400> SEQUENCE: 260
ugauaacuug uucuagaggu g 21

<210> SEQ ID NO 261
<211> LENGTH: 21
<212> TYPE: RNA
<213> ORGANISM: Synthetic oligonucleotide

<400> SEQUENCE: 261
caccucuaga acaaguuauc a 21

<210> SEQ ID NO 262
<211> LENGTH: 21
<212> TYPE: RNA
<213> ORGANISM: Synthetic oligonucleotide

<400> SEQUENCE: 262
ugauaacuug uucuagaggu g 21

<210> SEQ ID NO 263
<211> LENGTH: 19
<212> TYPE: RNA
<213> ORGANISM: Synthetic oligonucleotide

<400> SEQUENCE: 263
ccucuagaac aaguuauca 19

<210> SEQ ID NO 264
<211> LENGTH: 19
<212> TYPE: RNA
<213> ORGANISM: Synthetic oligonucleotide

<400> SEQUENCE: 264
ugauaacuug uucuagagg 19

<210> SEQ ID NO 265
<211> LENGTH: 21
<212> TYPE: RNA
<213> ORGANISM: Synthetic oligonucleotide

<400> SEQUENCE: 265
caccucuaga acaaguuauc a 21

<210> SEQ ID NO 266
<211> LENGTH: 21
<212> TYPE: RNA
<213> ORGANISM: Synthetic oligonucleotide

<400> SEQUENCE: 266
ugauaacuug uucuagaggu g 21

<210> SEQ ID NO 267
<211> LENGTH: 21
<212> TYPE: RNA
<213> ORGANISM: Synthetic oligonucleotide

<400> SEQUENCE: 267
caccucuaga acaaguaauc a 21

<210> SEQ ID NO 268
<211> LENGTH: 21
<212> TYPE: RNA
<213> ORGANISM: Synthetic oligonucleotide

<400> SEQUENCE: 268
ugauuacuug uucuagaggu g 21

<210> SEQ ID NO 269
<211> LENGTH: 21
<212> TYPE: RNA
<213> ORGANISM: Synthetic oligonucleotide

<400> SEQUENCE: 269
gccucuagaa caaguuauca a 21

<210> SEQ ID NO 270
<211> LENGTH: 21
<212> TYPE: RNA
<213> ORGANISM: Synthetic oligonucleotide

<400> SEQUENCE: 270
uugauaacuu guucuagagg c 21

<210> SEQ ID NO 271
<211> LENGTH: 21
<212> TYPE: RNA
<213> ORGANISM: Synthetic oligonucleotide

<400> SEQUENCE: 271
ccucuagaac aaguuaucac a 21

<210> SEQ ID NO 272
<211> LENGTH: 21
<212> TYPE: RNA
<213> ORGANISM: Synthetic oligonucleotide

<400> SEQUENCE: 272
ugugauaacu uguucuagag g 21

<210> SEQ ID NO 273
<211> LENGTH: 20
<212> TYPE: RNA
<213> ORGANISM: Synthetic oligonucleotide

<400> SEQUENCE: 273
ccagauaaag guggaucuca 20

<210> SEQ ID NO 274
<211> LENGTH: 20
<212> TYPE: RNA
<213> ORGANISM: Synthetic oligonucleotide

<400> SEQUENCE: 274
ugagauccac cuuuaucugg 20

<210> SEQ ID NO 275
<211> LENGTH: 20
<212> TYPE: RNA
<213> ORGANISM: Synthetic oligonucleotide

<400> SEQUENCE: 275
caaaggugga ucuccuuaca 20

<210> SEQ ID NO 276
<211> LENGTH: 20
<212> TYPE: RNA
<213> ORGANISM: Synthetic oligonucleotide

<400> SEQUENCE: 276
uguaaggaga uccaccuuug 20

<210> SEQ ID NO 277
<211> LENGTH: 19
<212> TYPE: RNA
<213> ORGANISM: Synthetic oligonucleotide

<400> SEQUENCE: 277
agguggaucu ccuuacgua 19

<210> SEQ ID NO 278
<211> LENGTH: 21
<212> TYPE: RNA
<213> ORGANISM: Synthetic oligonucleotide

<400> SEQUENCE: 278
uacguaagga gauccaccuu u 21

<210> SEQ ID NO 279
<211> LENGTH: 20
<212> TYPE: RNA
<213> ORGANISM: Synthetic oligonucleotide

<400> SEQUENCE: 279
cagguggauc uccuuacgua 20

<210> SEQ ID NO 280
<211> LENGTH: 20
<212> TYPE: RNA
<213> ORGANISM: Synthetic oligonucleotide

<400> SEQUENCE: 280
uacguaagga gauccaccug 20

<210> SEQ ID NO 281
<211> LENGTH: 21
<212> TYPE: RNA
<213> ORGANISM: Synthetic oligonucleotide

<400> SEQUENCE: 281
caagguggau cuccuuacgu a 21

<210> SEQ ID NO 282
<211> LENGTH: 21
<212> TYPE: RNA
<213> ORGANISM: Synthetic oligonucleotide

<400> SEQUENCE: 282
uacguaagga gauccaccuu g 21

<210> SEQ ID NO 283
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 283
cuggaaaccu cuagaacaan n 21

<210> SEQ ID NO 284
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 284
uuguucuaga gguuuccagn n 21

<210> SEQ ID NO 285
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 285
ggaaaccucu agaacaagan n 21

<210> SEQ ID NO 286
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 286
ucuuguucua gagguuuccn n 21

<210> SEQ ID NO 287
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 287
gaaaccucua gaacaaguan n 21

<210> SEQ ID NO 288
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 288
uacuuguucu agagguuucn n 21

<210> SEQ ID NO 289

<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 289
aaaccucuag aacaaguuan n 21

<210> SEQ ID NO 290
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 290
uaacuuguuc uagagguuun n 21

<210> SEQ ID NO 291
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 291
aaccucuaga acaaguuaan n 21

<210> SEQ ID NO 292
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 292
uuaacuuguu cuagagguun n 21

<210> SEQ ID NO 293
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 293
accucuagaa caaguuauan n 21

<210> SEQ ID NO 294
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 294
uauaacuugu ucuagaggun n 21

<210> SEQ ID NO 295
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 295
cucuagaaca aguuaucaan n 21

<210> SEQ ID NO 296
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 296
uugauaacuu guucuagagn n 21

<210> SEQ ID NO 297
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 297
ucuagaacaa guuaucacan n 21

<210> SEQ ID NO 298
<211> LENGTH: 21
<212> TYPE: RNA
<213> ORGANISM: Synthetic oligonucleotide
<220> FEATURE:
<221> NAME/KEY: misc_feature
<222> LOCATION: (20)..(21)
<223> OTHER INFORMATION: n is 2'-deoxythymidine-3'-phosphate

<400> SEQUENCE: 298
ugugauaacu uguucuagan n 21

<210> SEQ ID NO 299
<211> LENGTH: 19
<212> TYPE: RNA
<213> ORGANISM: Homo sapiens

<400> SEQUENCE: 299
cuggaaaccu cuagaacaa 19

<210> SEQ ID NO 300
<211> LENGTH: 19
<212> TYPE: RNA
<213> ORGANISM: Homo sapiens

<400> SEQUENCE: 300
ggaaaccucu agaacaagu 19

-continued

<210> SEQ ID NO 301
<211> LENGTH: 19
<212> TYPE: RNA
<213> ORGANISM: Homo sapiens

<400> SEQUENCE: 301
gaaaccucua gaacaaguu 19

<210> SEQ ID NO 302
<211> LENGTH: 19
<212> TYPE: RNA
<213> ORGANISM: Homo sapiens

<400> SEQUENCE: 302
aaaccucuag aacaaguua 19

<210> SEQ ID NO 303
<211> LENGTH: 19
<212> TYPE: RNA
<213> ORGANISM: Homo sapiens

<400> SEQUENCE: 303
aaccucuaga acaaguuau 19

<210> SEQ ID NO 304
<211> LENGTH: 19
<212> TYPE: RNA
<213> ORGANISM: Homo sapiens

<400> SEQUENCE: 304
accucuagaa caaguuauc 19

<210> SEQ ID NO 305
<211> LENGTH: 19
<212> TYPE: RNA
<213> ORGANISM: Homo sapiens

<400> SEQUENCE: 305
cucuagaaca aguuaucac 19

<210> SEQ ID NO 306
<211> LENGTH: 19
<212> TYPE: RNA
<213> ORGANISM: Homo sapiens

<400> SEQUENCE: 306
ucuagaacaa guuaucaca 19

COMPOSITIONS AND METHODS FOR INHIBITING EXPRESSION OF METHYLATION-CONTROLLED J-PROTEIN (MCJ)

RELATED APPLICATIONS

This application claims priority under 35 U.S.C. § 371 to International application number PCT/US2021/018933 filed Feb. 20, 2021, which claims benefit under 35 U.S.C. § 119 (e) of U.S. Provisional application Ser. No. 62/979,833 filed Feb. 21, 2020, the disclosure of each of which is incorporated by reference herein in its entirety.

FIELD OF THE INVENTION

The invention relates, in part, to compositions and methods that can be used to inhibit expression of methylation-controlled J-protein (MCJ) expression.

REFERENCE TO AN ELECTRONIC SEQUENCE LISTING

The contents of the electronic sequence listing (MIX004USsequencelisting.txt, Size: 66,256 bytes; and Date of Creation: Aug. 18, 2022) is herein incorporated by reference in its entirety.

BACKGROUND

Various inhibitory RNA molecules have been identified that can be used to reduce expression of a specific gene in a cell resulting in a reduction of activity in the cell. Such methods can be applied as treatments to a disease and/or condition that is caused or modulated by expression of the specific gene. Methylation-controlled J-Protein (MCJ) protein has been identified as playing an important role in many diseases and conditions such as: metabolic disorders, steatosis, liver diseases, kidney disease, and more.

SUMMARY OF THE INVENTION

According to an aspect of the invention, a double-stranded ribonucleic acid (dsRNA) agent for inhibiting expression of methylation-controlled J-protein (MCJ) is provided, the dsRNA agent including a sense strand and an antisense strand, the antisense strand including a region of complementarity to an MCJ RNA transcript, which includes at least 15 contiguous nucleotides and differs by no more than 3 nucleotides from one of the antisense sequences listed in Table 1 or Table 6 (L optional), and wherein the dsRNA agent optionally includes a targeting ligand. In some embodiments, the MCJ RNA transcript is any one of the target regions of SEQ ID NO: 2 provided in Table 2. In certain embodiments, the dsRNA agent includes a sense strand sequence set forth in Table 1 or Table 6 (linker is optional). In some embodiments the sense strand of the dsRNA agent has a sequence of a sense strand shown in Table 6 but without a targeting ligand (L). In some embodiments, the dsRNA agent includes an antisense strand sequence set forth in Table 1 or Table 6 (linker is optional. In some embodiments, the dsRNA agent includes at least one modified nucleotide. In certain embodiments, the at least one modified nucleotide includes a 2'-O-methyl nucleotide, 2'-Fluoro nucleotide, 2'-deoxy nucleotide, 2'3'-seco nucleotide mimic, locked nucleotide, 2'-F-Arabino nucleotide, 2'-methoyxyethyl nucleotide, abasic nucleotide, ribitol, inverted nucleotide, inverted abasic nucleotide, inverted 2'-OMe nucleotide, inverted 2'deoxy nucleotide, 2'-amino-modified nucleotide, 2'-alkyl-modified nucleotide, mopholino nucleotide, and 3'-OMe nucleotide, a nucleotide comprising a 5'-phosphorothioate group, or a terminal nucleotide linked to a cholesteryl derivative or dodecanoic acid bisdecylamide group, a 2'-amino-modified nucleotide, 2'-alkyl-modified nucleotide, a phosphoramidate, or a non-natural base comprising nucleotide. In certain embodiments, the dsRNA agent comprises at least one phosphorothioate internucleoside linkage. In some embodiments, the sense strand comprises at least one phosphorothioate internucleoside linkage. In some embodiments, the antisense strand comprises at least one phosphorothioate internucleoside linkage. In certain embodiments, the sense strand comprises 1, 2, 3, 4, 5, or 6, phosphorothioate internucleoside linkages. In some embodiments, the antisense strand comprises 1, 2, 3, 4, 5, or 6, phosphorothioate internucleoside linkages. In some embodiments, all or substantially all of the nucleotides of the sense strand and the antisense strand are modified nucleotides. In some embodiments, the sense strand is complementary to the antisense strand, and the region of complementarity is between 16 and 23 nucleotides in length. In certain embodiments, the region of complementarity is 19-21 nucleotides in length. In some embodiments, each strand is no more than 30 nucleotides in length. In some embodiments, each strand is no more than 25 nucleotides in length. In certain embodiments, each strand is no more than 23 nucleotides in length. In certain embodiments, the dsRNA agent comprises at least one modified nucleotide and further comprises one or more targeting groups or linking groups. In some embodiments, the one or more targeting groups or linking groups are conjugated to the sense strand. In some embodiments, the targeting group or linking group comprises N-acetyl-galactosamine (GalNAc). In some embodiments, GalNAc is targeting ligand Mito-F. In certain embodiments, dsRNA agent comprises a targeting group that is conjugated to the 5'-terminal end of the sense strand. In certain embodiments, the dsRNA agent has two blunt ends. In some embodiments, at least one strand comprises a 3' overhang of at least 1 nucleotide. In some embodiments, at least one strand comprises a 3' overhang of at least 2 nucleotides. In certain embodiments, the dsRNA agent comprises at least one modified nucleotide and does not include a targeting group or agent.

According to another aspect of the invention, a composition including an embodiment of a dsRNA agent of any of the aforementioned compositions is provided. In certain embodiments, the composition also includes a pharmaceutically acceptable carrier. In some embodiments, the composition also includes 1, 2, 3, 4, or more additional therapeutic agents. In some embodiments, the composition is packaged in a kit, container, pack, dispenser, pre-filled syringe, or vial. In some embodiments, the composition is formulated for subcutaneous administration or is formulated for intravenous (IV) administration.

According to another aspect of the invention, a cell including comprising a dsRNA agent of any of the aforementioned compositions is provided. In certain embodiments, the cell is a mammalian cell, optionally a human cell.

According to another aspect of the invention, a method of inhibiting the expression of a methylation-controlled J-protein (MCJ) gene in a cell is provided, the method including: (a) preparing a cell comprising an effective amount of any embodiment of a double-stranded ribonucleic acid (dsRNA) agent of any of the aforementioned compositions is provided. In some embodiments, the method also includes (b)

maintaining the cell prepared in (a) for a time sufficient to obtain degradation of the mRNA transcript of an MCJ gene, thereby inhibiting expression of the MCJ gene in the cell. In some embodiments, the cell is in a subject and the dsRNA agent is administered to the subject subcutaneously. In certain embodiments, the cell is in a subject and the dsRNA agent is administered to the subject by IV administration.

According to another aspect of the invention, a method of inhibiting expression of a methylation-controlled J-protein (MCJ) gene in a subject is provided, the method including administering to the subject an effective amount of a double-stranded ribonucleic acid (dsRNA) agent of any including an embodiment of a dsRNA agent of any of the aforementioned aspects of the invention, and/or any embodiment of an aforementioned composition. To inhibit expression of the MCJ gene in the subject. In some embodiments, the dsRNA agent is administered to the subject subcutaneously. In some embodiments, the dsRNA agent is administered to the subject by IV administration.

According to another aspect of the invention, a method of treating a disease or condition associated with the presence or a level of methylation-controlled J-protein (MCJ) in a subject is provided, the method including administering to the subject an effective amount of any embodiment of a double-stranded ribonucleic acid (dsRNA) agent of any of the aforementioned aspects of the invention, or any embodiment of an aforementioned composition to inhibit MCJ gene expression. In some embodiments, the disease or condition is one or more of: a metabolic disease or condition, a lipid accumulation disease or condition, a cancer, a liver disease or condition, a cardiac disease or condition, a kidney disease or condition, an immune system disease or condition, a neurological disease or condition, and a lung disease or condition. In certain embodiments, the disease or condition is hepatitis, non-alcoholic fatty liver disease, overweight, weight gain, obesity, diabetes, insulin-resistance, alcoholic fatty liver disease, dyslipidemia, steatosis, liver steatosis, heart steatosis, kidney steatosis, muscle steatosis, abetalipoproteinemia, glycogen storage disease, Weber-Christian disease, lipodystrophy; a liver disease, liver inflammation, hepatitis, cholestasis, liver failure, steatohepatitis, Hepatitis C, Genotype 3 Hepatitis C, Alpha 1-antitrypsin deficiency, acute fatty liver of pregnancy, Wilson disease; a kidney disease; chronic kidney disease, polycystic kidney disease, a cardiac disease, hypertension, ischemia, heart failure, cardiomyopathy; overdose, poisoning; HIV; a neurodegenerative disease, liver transplantation, kidney transplantation, heart transplantation, Parkinson's disease, Alzheimer's disease; cancer, or physical exercise. In some embodiments, the dsRNA agent is administered to the subject subcutaneously. In some embodiments, the dsRNA agent is administered to the subject by IV administration. In some embodiments, treating the disease or condition reduces the level of MCJ compared to a control level.

According to another aspect of the invention, a method of decreasing a level of methylation-controlled J-protein (MCJ) in a subject compared to a baseline pre-treatment level of MCJ in the subject is provided, the method including administering to the subject an effective amount of any embodiment of a double-stranded ribonucleic acid (dsRNA) agent of any of the aforementioned aspects of the invention, or any embodiment of an aforementioned composition to inhibit MCJ gene expression, to decrease the level of MCJ gene expression. In certain embodiments, the dsRNA agent is administered to the subject subcutaneously or is administered to the subject by IV administration.

According to another aspect of the invention, an antisense polynucleotide agent for inhibiting expression of methylation controlled-J-protein (MCJ) is provided, wherein the agent includes from 10 to 30 contiguous nucleotides, wherein at least one of the contiguous nucleotides is a modified nucleotide, and wherein the nucleotide sequence of the agent is about 80% or is about 85% complementary over its entire length to the equivalent region of the nucleotide sequence of SEQ ID NO: 2. In some embodiments, the equivalent region is any one of the target regions of SEQ ID NO: 2 provided in Table 2. In some embodiments, the antisense polynucleotide agent comprises one of the antisense sequences provided in Table 6. In some embodiments the sense strand of the dsRNA agent has a sequence of a sense strand shown in Table 6 but without a targeting ligand (L)

According to another aspect of the invention, a composition including any embodiment of any aforementioned antisense polynucleotide agent is provided. In certain embodiments, the composition also includes a pharmaceutically acceptable carrier. In some embodiments, the composition also includes 1, 2, 3, 4, 5, or more additional therapeutic agents for treatment of an MCJ-associated disease or condition. In certain embodiments, the composition is packaged in a kit, container, pack, dispenser, pre-filled syringe, or vial. In some embodiments, the composition is formulated for subcutaneous or IV administration.

According to another aspect of the invention, a cell including any embodiment of any aforementioned antisense polynucleotide agent is provided. In some embodiments, the cell is a mammalian cell, optionally a human cell.

According to another aspect of the invention, a method of inhibiting the expression of a methylation-controlled J-protein (MCJ) gene in a cell is provided, the method including (a) preparing a cell comprising an effective amount of any embodiment of an aforementioned antisense polynucleotide agent. In certain embodiments, the method also includes (b) maintaining the cell prepared in (a) for a time sufficient to obtain degradation of the mRNA transcript of an MCJ gene, thereby inhibiting expression of the MCJ gene in the cell.

According to another aspect of the invention, a method of inhibiting expression of a methylation-controlled J-protein (MCJ) gene in a subject is provided, the method including: administering to the subject an effective amount of any embodiment of any aforementioned MCJ antisense polynucleotide agent or any embodiment of an aforementioned composition to inhibit MCJ gene expression.

According to another aspect of the invention, a method of treating a disease or condition associated with the presence of methylation-controlled J-protein (MCJ) is provided, the method including administering to a subject an effective amount of any embodiment of any aforementioned MCJ antisense polynucleotide agent, or any embodiment of an aforementioned composition that includes an MCJ antisense polynucleotide agent, to inhibit MCJ gene expression. In some embodiments, the disease or condition is one or more of: a metabolic disease or condition, a lipid accumulation disease or condition, a cancer, a liver disease or condition, a cardiac disease or condition, a kidney disease or condition, an immune system disease or condition, a neurological disease or condition, and a lung disease or condition.

According to another aspect of the invention, a method of decreasing a level of methylation-controlled J-protein (MCJ) in a subject compared to a baseline pre-treatment level of MCJ in the subject is provided, the method including administering to the subject an effective amount of any embodiment of any aforementioned MCJ antisense polynucleotide agent, or any embodiment of an aforementioned composition that includes an MCJ antisense polynucleotide agent an antisense polynucleotide agent to decrease the level of MCJ gene expression. In some embodiments, the antisense polynucleotide agent is administered to the subject subcutaneously or by IV administration.

According to another aspect of the invention, an antisense polynucleotide agent for inhibiting expression of methylation controlled J-protein (MCJ) is provided, wherein the agent includes from 10 to 30 contiguous nucleotides, wherein at least one of the contiguous nucleotides is a modified nucleotide, and wherein the nucleotide sequence of the agent is about 80% or about 85% complementary over its entire length to the equivalent region of the nucleotide sequence of SEQ ID NO: 2.

The present invention is not intended to be limited to a composition or method that must satisfy one or more of any stated objects or features of the invention. It is also important to note that the present invention is not limited to the exemplary or primary embodiments described herein. Modifications and substitutions by one of ordinary skill in the art are considered to be within the scope of the present invention.

BRIEF DESCRIPTION OF THE SEQUENCES

SEQ ID NO: 1 is amino acid sequence of human methylation-controlled J-protein (MCJ) with Genbank® Accession No. NP_037370.2:

```
MAARGVIAPVGESLRYAEYLQPSAKRPDADVDQQRLVRSLIAVGLGVAA
LAFAGRYAFRIWKPLEQVITETAKKISTPSFSSYYKGGFEQKMSRREAG
LILGVSPSAGKAKIRTAHRRVMILNHPDKGGSPYVAAKINEAKDLLETT
TKH.
```

SEQ ID NO: 2 is mRNA sequence of human methylation-controlled J-protein (MCJ) with Genbank® Accession No.: NM_013238.2:

```
caccctcaggcactacagctagactccgagcttactgggcagtcatctg
attcgaccaacatcagttcgcagggcttaagcccagtcccttacggcgg
cctggggagggaccaggcccaagtatataaagctccctgagggtccgcg
ttggctttgcgcctgtgagtgtgattcaagaacgtcccagtgcccttgg
ctcctttcggagtgtgaccccgtgcttgcacgggacacgttacccagct
cgggtgagaagggtatcttccgggaacctcgcctttaatagcacaacga
gcgcagagtccactggatctgcgagaagaaaccgcgctaactagtttgt
ccctacggccgcctcgtagtcactgccgcggcgccttgagtctccgggc
cgccttgccatggctgcccgtggtgtcatcgctccagttggcgagagtt
tgcgctacgctgagtacttgcagccctcggccaaacggccagacgccga
cgtcgaccagcagagactggtaagaagtttgatagctgtaggactgggt
gttgcagctcttgcatttgcaggtcgctacgcatttcggatctggaaac
ctctagaacaagttatcacagaaactgcaaagaagatttcaactcctag
cttttcatcctactataaaggaggatttgaacagaaaatgagtaggcga
gaagctggtcttattttaggtgtaagcccatctgctggcaaggctaaga
```

-continued

```
ttagaacagctcataggagagtcatgattttgaatcacccagataaagg
tggatctccttacgtagcagccaaaataaatgaagcaaaagacttgcta
gaaacaaccaccaaacattgatgcttaaggaccacactgaaggaaaaa
aaagaggggacttcgaaaaaaaaaaaagccctgcaaaatattctaaaac
atggtcttcttaattttctatatggattgaccacagtcttatcttccac
cattaagctgtataacaataaaatgttaatagtcttgctttttattatc
ttttaaagatctccttaaattctataactgatctttttcttattttgt
ttgtgacattcatacattttaagatttttgttatgttctgaattcccc
cctacacacacacacacacacacacacacacacgtgcaaaaaatatg
atcaagaatgcaattgggatttgtgagcaatgagtagacctcttattgt
ttatatttgtaccctcattgtcaattttttttagggaatttgggactc
tgcctatataaggtgttttaaatgtcttgagaacaagcactggctgata
cctcttggagatatgatctgaaatgtaatggaatttattaaatggtgtt
tagtaaagtaggggttaaggacttgttaaagaaccccactatctctgag
accctatagccaaagcatgaggacttggagagctactaaaatgattcag
gtttacaaaatgagccctgtgaggaaaggttgagagaagtctgaggagt
ttgtatttaattatagtcttccagtactgtatattcattcattactcat
tctacaaatatttattgacccctttgatgtgcaaggcactatcgtgcg
tcccctgagagttgcaagtatgaagcagtcatggatcatgaaccaaagg
aacttatatgtagaggaaggataaatcacaaatagtgaatactgttaga
tacagatgatatattttaaaagttcaaaggaagaaaagaatgtgttaaa
cactgcatgagaggaggaataagtggcatagagctaggctttagaaaag
aaaaatattccgataccatatgattggtgaggtaagtgttattctgaga
tgagaattagcagaaatagatatatcaatcggagtgattagagtgcagg
gtttctggaaagcaaggtttggacagagtggtcatcaaaggccagccct
gtgacttacactgcattaaattaatttcttagaacatagtccctgatca
ttatcactttactattccaaaggtgagagaacagattcagatagagtgc
cagcattgtttcccagtattcctttacaaatcttgggttcattccaggt
aaactgaactactgcattgtttctatcttaaaatactttttagatatcc
tagatgcatctttcaacttctaacattctgtagtttaggagttctcaac
cttggcattattgacatgttaggccaaataatttttttgtgggaggtc
tcttgtgcgttttagatgattagcaataatccctgacctgttatctact
aaagactagtcgtttctcatcagttgtgacaacaaaaatggttccagat
attgccaaatgccctttagaggacagtaatcgcccccagttgagaacca
tttcagtaaaactttaattactatttttttcttttggtttataaaataat
gatcctgaattaaattgatggaaccttgaagtcgataaaatatatttct
tgctttaaagtccccatacgtgtcctactaattttctcatgctttagtg
ttttcacttttctcctgttatccttgtacctaagaatgccatcccaatc
cccagatgtccacctgcccaaagtctaggcatagctgaaggccaagcta
aaatgtatccctctttttctggtacatgcagcaaaagtaatatgaatta
```

-continued

```
tcagctttctgagagcaggcattgtatctgtcttgtttggtgttacatt

ggcacccaataaatatttgttgagtgaatgaaaaaaaaaaaaaaaaaa.
```

SEQ ID NOs: 3-114 and 283-298 are shown in Table 1 in which double-stranded sequences are referred to as MITO-1 through MITO-64 and each includes the sense and antisense strands in the rows corresponding to the MITO numbers. The SEQ ID NOs for each of the single strands are shown in the last column on the right as SEQ ID NOs: 3-114 and 283-298.

SEQ ID NOs: 115-170 and 299-306 are provided in Table 2. These sequences are also referred to as: target regions in the MCJ RNA transcript. DNAJC15/MCJ sequences (also referred to herein as MCJ RNA sequences) targeted by the MITO siRNAs are shown in the third column of Table 2 with the SEQ ID NO for each of the DNAJC15/MCJ sequences provided in the fourth column.

SEQ ID NOs: 171-282 are shown in Table 6, with symbols applicable in Table 6 shown in Table 5. A targeting ligand, shown as "L" on sense-strand sequences is optional and in some embodiments of methods and compositions of the invention a dsRNA agent sense strand has a sense-strand sequence shown in Table 6 but without a targeting ligand (L).

DETAILED DESCRIPTION

Methylation-controlled J-protein (MCJ) is a member of the DnaJ family of co-chaperones. A wild-type, full-length MCJ polypeptide amino acid sequence is set forth as Genbank® Accession No. NP_037370.2 (SEQ ID NO: 1). A nucleic acid sequence encoding wild-type, full-length, human MCJ polypeptide is set forth as Genbank® Accession No.: NM_013238.2 (SEQ ID NO: 2). Described herein are inhibiting RNA (iRNA) agents that can be used to inhibit expression of an MCJ gene in a cell or a subject. An MCJ dsRNA agent of the invention directs the sequence-specific degradation of MCJ mRNA through a process known as RNA interference (RNAi). The terms" "siMCJ," "MCJ siRNA," and "MCJ iRNA" may be used interchangeably herein and terms MCJ dsRNA agent and MCJ antisense polynucleotide agent are siMCJ, MCJ siRNA, and MCJ iRNA agents.

An iRNA agent that targets an MCJ gene and inhibits MCJ gene expression may be referred to herein as: an MCJ iRNA agent and an MCJ double-strand RNA (dsRNA) agent or an MCJ antisense polynucleotide agent. Also provided are compositions and methods for reducing MCJ expression in cells and subjects that can be used to treat diseases associated with MCJ expression. The terms "associated with MCJ expression" and MCJ-associated" as used herein in relation to diseases and conditions means diseases and/or conditions for which reduction of MCJ expression can be beneficial in treating the disease and/or condition. As used herein, "associated with MCJ expression and MCJ-associated diseases and/or conditions are those diseases and/or conditions that are impacted by a change in one or more of: the expression of an MCJ gene and activity level of the MCJ gene product. In some embodiments of the invention reducing MCJ expression in a cell or subject treats a disease or condition associated with MCJ expression in the cell or subject, respectively. Non-limiting examples of diseases and conditions that may be treated by reducing MCJ activity are: a metabolic disease or condition, a cancer, a lipid accumulation disease or condition, a drug-induced disease or condition, as well as other disease and conditions disclosed herein that are caused by or modulated by the expression of an MCJ gene. Examples of such disease or conditions include but are not limited to: metabolic diseases and conditions, liver diseases and conditions, kidney diseases and conditions, drug-induced diseases and conditions, cancers, etc. The following describes how to make and use compositions comprising MCJ dsRNA agents or MCJ antisense polynucleotide agents to inhibit MCJ gene expression, as well as compositions and methods for treating diseases and conditions caused by or modulated by MCJ gene expression.

As used herein, the term "iRNA" refers to an agent that comprises RNA and mediates targeted cleavage of an RNA transcript via an RNA-induced silencing complex (RISC) pathway. As is known in the art, an iRNA a target region refers to a contiguous portion of the nucleotide sequence of an mRNA molecule formed during the transcription of a gene, including messenger RNA (mRNA) that is a product of RNA processing of a primary transcription product. The target portion of the sequence will be at least long enough to serve as a substrate for iRNA-directed cleavage at or near that portion. A target sequence may be between 8-30 nucleotides long (inclusive), including all lengths in that range. In some embodiments of the invention, a target sequence is between such as 9-25 nucleotides long (inclusive), including all sub-ranges and integers there between. For example, though not intended to be limiting, in certain embodiments of the invention a target sequence can be 9-25 nucleotides in length, 10-25 nucleotides in length, 11-25 nucleotides in length, 12-25 nucleotides in length, 13-25 nucleotides in length, 14-25 nucleotides in length, 15-25 nucleotides in length 16-25 nucleotides in length, 17-25 nucleotides in length, 18-25 nucleotides in length, 19-25 nucleotides in length, 20-25 nucleotides in length, 21-25 nucleotides in length, 18-24 nucleotides in length, 18-23 nucleotides in length, 19-21 nucleotides in length, 16 nucleotides in length, 17 nucleotides in length, 18 nucleotides in length, 19 nucleotides in length, 20 nucleotides in length, with the ranges inclusive and including all integers in the ranges. The terms "oligonucleotide" and "polynucleotide" are used interchangeably herein in reference to a polymer of linked nucleosides each of which can be independently modified or unmodified.

Embodiments of methods of the invention include delivering to a cell an RNAi agent that targets an MCJ gene thereby reducing a level of expression of MCJ protein in that cell. Use of MCJ iRNA agents as described herein permits targeted degradation of mRNAs of the MCJ gene, which have been identified as implicated in pathologies associated with MCJ expression in mammals. It has now been determined that MCJ dsRNA agents and MCJ antisense polynucleotide agents such as those described herein can be used to mediate RNA interference (RNAi), which results in reduced MCJ gene expression. Using in-vitro and in-vivo assays, it has now been determined that MCJ dsRNA agents and MCJ antisense polynucleotide agents targeting MCJ can specifically and efficiently reduce MCJ gene expression in cells, tissues, and subjects and that methods and compositions of the invention can be used to reduce MCJ activity in cells, tissues, and subjects and can be used to a disease or condition associate with MCJ protein activity. The terms protein and polypeptide may be used interchangeably herein. Certain embodiments of methods of the invention comprise administration of a single-stranded RNA, for example, an antisense polynucleotide strand such as one listed in Table 1 or Table 6.

Compositions included in certain embodiments of the invention comprise an MCJ dsRNA agent having an antisense strand comprising a region that is 23 nucleotides or less in length that may be 15-23 nucleotides in length, wherein the region is substantially complementary to at least part of an RNA transcript of an MCJ gene. In some embodiments a composition of the invention further comprises a pharmaceutically acceptable carrier. In certain embodiments of the invention, a composition may comprise an MCJ dsRNA agent having an antisense strand with a region of complementarity that is 23, 22, 21, 20, 19, 18, 17, 16, 15, 14, nucleotides or less in length, with the region substantially complementary to at least part of an RNA transcript of an MCJ gene. Some aspects of the invention include pharmaceutical compositions comprising one or more MCJ dsRNA agents and a pharmaceutically acceptable carrier. In certain embodiments of the invention, an MCJ iRNA as described herein inhibits expression of MCJ protein.

As used herein, a "dsRNA agent" means a composition that contains an RNA or RNA-like (e.g., chemically modified RNA) oligonucleotide molecule that is capable of degrading or inhibiting translation of messenger RNA (mRNA) transcripts of a target mRNA in a sequence specific manner. Although not wishing to be limited to a particular theory, dsRNA agents of the invention may operate through the RNA interference mechanism (i.e., inducing RNA interference through interaction with the RNA interference pathway machinery (RNA-induced silencing complex or RISC) of mammalian cells), or by any alternative mechanism(s) or pathway(s). Methods for silencing genes in plant, invertebrate, and vertebrate cells are well known in the art [see, for example, (Sharp et al., Genes Dev. 2001, 15:485; Bernstein, et al., (2001) Nature 409:363; Nykanen, et al., (2001) Cell 107:309; and Elbashir, et al., (2001) Genes Dev. 15:188)], the disclosure of each of which is incorporated herein by reference in its entirety.]. Art-known gene silencing procedures can be used in conjunction with the disclosure provided herein to inhibit expression of MCJ.

dsRNA agents disclosed herein are comprised of a sense strand and an antisense strand, and include, but are not limited to: short interfering RNAs (siRNAs), RNAi agents, micro RNAs (miRNAs), short hairpin RNAs (shRNA), and dicer substrates. The antisense strand of the dsRNA agents described herein is at least partially complementary to the mRNA being targeted. It is understood in the art that different lengths of dsRNA duplex structure can be used to inhibit target gene expression. For example, dsRNAs having a duplex structure of 20, 21, 22, and 23 base pairs are known to be effective to induce RNA interference (Elbashir et al., EMBO 2001, 20:6877-6888). It is also known in the art that shorter or longer RNA duplex structures are also effective to induce RNA interference. MCJ dsRNAs in certain embodiments of the invention can include at least one strand of a length of minimally 21 nt or may have shorter duplexes based on one of the sequences set forth in Table 1 minus 1, 2, 3, or 4 nucleotides on one or both ends may be also be effective as compared to the dsRNAs set forth in Table 1. In some embodiments of the invention, MCJ dsRNA agents may have a partial sequence of at least 15, 16, 17, 18, 19, 20, or more contiguous nucleotides from sequences of Table 1, and differ in their ability to inhibit the expression of an MCJ gene by not more than 5, 10, 15, 20, 25, or 30% from the level of inhibition resulting from a dsRNA comprising the full sequence, which is also referred to herein as the "parent" sequence.

Certain embodiments of compositions and methods of the invention comprise a single-strand RNA in a composition and/or administered to a subject. For example, an antisense strand such as one listed in Table 1 or Table 6 may be a composition or in a composition administered to a subject to reduce MCJ polypeptide activity and/or expression of MCJ gene in the subject. A single-strand antisense molecule that may be included in certain compositions and/or administered in certain methods of the invention are referred to herein as a "single-strand agent" or an "antisense polynucleotide agent".

Table 1 shows certain MCJ dsRNA agent antisense strand and sense strand core stretch base sequences. The first nucleotide in the 3'-end of sense strand (overhanging nucleotides not considered) was set as "a" regardless which nucleotide was in the natural sequence. The first nucleotide in the 5'-end of antisense strand was set as "u" regardless which nucleotide was the complementing nucleotide for the nucleotide in the sense strand of natural sequence. The table includes the nucleotide sequence of the sense and antisense strands of MCJ dsRNAs Mito-1 through Mito-64, which are SEQ ID NO: 3-298, respectively. In some embodiments of the invention includes method and/or compositions comprising sequences SEQ ID NO: 3-114 and 283-298, but without [dT][dT].

TABLE 1

Certain siRNAs designed to reduce MCJ levels. Column 1 shows the siRNA ID (ID) for each of the double-strand siRNA sequences. Column 2 indicates the position in the MCJ sequence SEQ ID NO: 2, "Pos." is "Position" of the siRNA on the MCJ sequence. Column 3, "Strnd", indicates the siRNA strand of the sequence, "S" for sense strand and "AS" for antisense strand. Column 4 shows the sequences, with [dT] representing 2'-deoxythymidine-3'-phosphate. Column 5, "Calc. MW" is calculated molecular weight. Column 6, "Obs Mass" is observed Mass, with "nc" indicating not calculated.

| siRNA ID | Pos. | Strnd | Sequences (5' to 3') | Calc MW | Obs Mass | SEQ ID NO |
|---|---|---|---|---|---|---|
| Mito-1 | 482 | S | agacgccgacgucgaccaa[dT][dT] | 6690.16 | 6693 | 3 |
| | 482 | AS | uuggucgacgucggcgucu[dT][dT] | 6655.02 | 6654.6 | 4 |
| Mito-2 | 524 | S | agcuguaggacugggugua[dT][dT] | 6766.15 | 6770.7 | 5 |
| | 524 | AS | uacacccaguccuacagcu[dT][dT] | 6549.01 | 6550.7 | 6 |
| Mito-3 | 526 | S | cuguaggacuggguguuga[dT][dT] | 6743.11 | 6747.6 | 7 |
| | 526 | AS | ucaacacccaguccuacag[dT][dT] | 6572.05 | 6573.8 | 8 |

TABLE 1-continued

Certain siRNAs designed to reduce MCJ levels. Column 1 shows the siRNA ID (ID) for each of the double-strand siRNA sequences. Column 2 indicates the position in the MCJ sequence SEQ ID NO: 2, "Pos." is "Position" of the siRNA on the MCJ sequence. Column 3, "Strnd", indicates the siRNA strand of the sequence, "S" for sense strand and "AS" for antisense strand. Column 4 shows the sequences, with [dT] representing 2'-deoxythymidine-3'-phosphate. Column 5, "Calc. MW" is calculated molecular weight. Column 6, "Obs Mass" is observed Mass, with "nc" indicating not calculated.

| siRNA ID | Pos. | Strnd | Sequences (5' to 3') | Calc MW | Obs Mass | SEQ ID NO |
|---|---|---|---|---|---|---|
| Mito-4 | 527 | S | uguaggacuggguguugca[dT][dT] | 6743.11 | 6746.9 | 9 |
| | 527 | AS | ugcaacacccaguccuaca[dT][dT] | 6572.05 | 6572.2 | 10 |
| Mito-5 | 528 | S | guaggacuggguguugcaa[dT][dT] | 6766.15 | 6770.6 | 11 |
| | 528 | AS | uugcaacacccaguccuac[dT][dT] | 6549.01 | 6551.8 | 12 |
| Mito-6 | 537 | S | gguguugcagcucuugcaa[dT][dT] | 6663.05 | 6666.1 | 13 |
| | 537 | AS | uugcaagagcugcaacacc[dT][dT] | 6652.11 | 6653.9 | 14 |
| Mito-7 | 542 | S | ugcagcucuugcauuugca[dT][dT] | 6583.98 | 6587.6 | 15 |
| | 542 | AS | ugcaaaugcaagagcugca[dT][dT] | 6716.17 | 6718 | 16 |
| Mito-8 | 545 | S | agcucuugcauuugcagga[dT][dT] | 6647.05 | 6650.8 | 17 |
| | 545 | AS | uccugcaaaugcaagagcu[dT][dT] | 6653.1 | 6654.5 | 18 |
| Mito-9 | 546 | S | gcucuugcauuugcaggua[dT][dT] | 6624.01 | 6627 | 19 |
| | 546 | AS | uaccugcaaaugcaagagc[dT][dT] | 6676.14 | 6677.2 | 20 |
| Mito-10 | 551 | S | ugcauuugcaggucgcuaa[dT][dT] | 6647.05 | 6650.6 | 21 |
| | 551 | AS | uuagcgaccugcaaaugca[dT][dT] | 6653.1 | 6657.7 | 22 |
| Mito-11 | 552 | S | gcauuugcaggucgcuaca[dT][dT] | 6646.06 | 6650.4 | 23 |
| | 552 | AS | uguagcgaccugcaaaugc[dT][dT] | 6669.1 | 6670.2 | 24 |
| Mito-12 | 555 | S | uuugcaggucgcuacgcaa[dT][dT] | 6646.06 | 6650.4 | 25 |
| | 555 | AS | uugcguagcgaccugcaaa[dT][dT] | 6669.1 | 6670.2 | 26 |
| Mito-13 | 556 | S | uugcaggucgcuacgcaua[dT][dT] | 6646.06 | 6649.8 | 27 |
| | 556 | AS | uaugcguagcgaccugcaa[dT][dT] | 6669.1 | 6671.9 | 28 |
| Mito-14 | 557 | S | ugcaggucgcuacgcauua[dT][dT] | 6646.06 | 6649.9 | 29 |
| | 557 | AS | uaaugcguagcgaccugca[dT][dT] | 6669.1 | 6668.2 | 30 |
| Mito-15 | 558 | S | gcaggucgcuacgcauuua[dT][dT] | 6646.06 | 6649 | 31 |
| | 558 | AS | uaaaugcguagcgaccugc[dT][dT] | 6669.1 | 6669.6 | 32 |
| Mito-16 | 559 | S | caggucgcuacgcauuuca[dT][dT] | 6606.03 | 6610.8 | 33 |
| | 559 | AS | ugaaaugcguagcgaccug[dT][dT] | 6709.13 | 6711.3 | 34 |
| Mito-17 | 570 | S | gcauuucggaucuggaaaa[dT][dT] | 6694.12 | 6698 | 35 |
| | 570 | AS | uuuuccagauccgaaaugc[dT][dT] | 6591.02 | 6591.3 | 36 |
| Mito-18 | 571 | S | cauuucggaucuggaaaca[dT][dT] | 6654.09 | 6658 | 37 |
| | 571 | AS | uguuuccagauccgaaaug[dT][dT] | 6631.05 | 6632.3 | 38 |
| Mito-19 | 579 | S | aucuggaaaccucuagaaa[dT][dT] | 6661.13 | 6665.3 | 39 |
| | 579 | AS | uuucuagagguuuccagau[dT][dT] | 6609 | 6608.8 | 40 |
| Mito-20 | 580 | S | ucuggaaaccucuagaaca[dT][dT] | 6637.1 | 6641.5 | 41 |
| | 580 | AS | uguucuagagguuuccaga[dT][dT] | 6648.04 | 6648.8 | 42 |
| Mito-21 | 588 | S | ccucuagaacaaguuauca[dT][dT] | 6598.06 | 6601.9 | 43 |
| | 588 | AS | ugauaacuuguucuagagg[dT][dT] | 6672.07 | 6672 | 44 |
| Mito-22 | 632 | S | uccuagcuuuucauccuaa[dT][dT] | 6488.91 | 6493.7 | 45 |
| | 632 | AS | uuaggaugaaaagcuagga[dT][dT] | 6781.22 | 6782.2 | 46 |
| Mito-23 | 635 | S | uagcuuuucauccuacuaa[dT][dT] | 6512.94 | 6517.2 | 47 |
| | 635 | AS | uuaguaggaugaaaagcua[dT][dT] | 6742.18 | 6744.1 | 48 |
| Mito-24 | 636 | S | agcuuuucauccuacuaua[dT][dT] | 6512.94 | 6516.9 | 49 |
| | 636 | AS | uauaguaggaugaaaagcu[dT][dT] | 6742.18 | 6742.8 | 50 |
| Mito-25 | 637 | S | gcuuuucauccuacuauaa[dT][dT] | 6512.94 | 6516.5 | 51 |
| | 637 | AS | uuauaguaggaugaaaagc[dT][dT] | 6742.18 | 6743.7 | 52 |

TABLE 1-continued

Certain siRNAs designed to reduce MCJ levels. Column 1 shows the siRNA ID (ID) for each of the double-strand siRNA sequences. Column 2 indicates the position in the MCJ sequence SEQ ID NO: 2, "Pos." is "Position" of the siRNA on the MCJ sequence. Column 3, "Strnd", indicates the siRNA strand of the sequence, "S" for sense strand and "AS" for antisense strand. Column 4 shows the sequences, with [dT] representing 2'-deoxythymidine-3'-phosphate. Column 5, "Calc. MW" is calculated molecular weight. Column 6, "Obs Mass" is observed Mass, with "nc" indicating not calculated.

| siRNA ID | Pos. | Strnd | Sequences (5' to 3') | Calc MW | Obs Mass | SEQ ID NO |
|---|---|---|---|---|---|---|
| Mito-26 | 641 | S | uucauccuacuauaaagga[dT][dT] | 6599.05 | 6603.3 | 53 |
| | 641 | AS | uccuuuauaguaggaugaa[dT][dT] | 6656.07 | 6654.5 | 54 |
| Mito-27 | 642 | S | ucauccuacuauaaaggaa[dT][dT] | 6622.09 | 6626 | 55 |
| | 642 | AS | uuccuuuauaguaggauga[dT][dT] | 6633.03 | 6633.6 | 56 |
| Mito-28 | 643 | S | cauccuacuauaaaggaga[dT][dT] | 6661.13 | 6665.6 | 57 |
| | 643 | AS | ucuccuuuauaguaggaug[dT][dT] | 6609 | 6612.7 | 58 |
| Mito-29 | 669 | S | cagaaaaugaguaggcgaa[dT][dT] | 6803.27 | 6807.6 | 59 |
| | 669 | AS | uucgccuacucauuuucug[dT][dT] | 6481.87 | 6483.7 | 60 |
| Mito-30 | 690 | S | gcuggucuuauuuuaggua[dT][dT] | 6625.99 | 6629.6 | 61 |
| | 690 | AS | uaccuaaaauaagaccagc[dT][dT] | 6644.14 | 6645.6 | 62 |
| Mito-31 | 691 | S | cuggucuuauuuuagguga[dT][dT] | 6625.99 | 6630.4 | 63 |
| | 691 | AS | ucaccuaaaauaagaccag[dT][dT] | 6644.14 | 6644.7 | 642 |
| Mito-32 | 692 | S | uggucuuauuuuaggugua[dT][dT] | 6626.98 | 6631.1 | 65 |
| | 692 | AS | uacaccuaaaauaagacca[dT][dT] | 6628.14 | 6627.7 | 66 |
| Mito-33 | 700 | S | uuuuagguguaagcccaua[dT][dT] | 6632.04 | 6635.7 | 67 |
| | 700 | AS | uaugggcuuacaccuaaaa[dT][dT] | 6638.09 | 6639.9 | 68 |
| Mito-34 | 702 | S | uuagguguaagcccaucua[dT][dT] | 6631.05 | 6635.1 | 69 |
| | 702 | AS | uagaugggcuuacaccuaa[dT][dT] | 6654.09 | 6655.6 | 70 |
| Mito-35 | 704 | S | agguguaagcccaucugca[dT][dT] | 6669.1 | 6673 | 71 |
| | 704 | AS | ugcagaugggcuuacaccu[dT][dT] | 6646.06 | 6647.7 | 72 |
| Mito-36 | 711 | S | agcccaucugcuggcaaga[dT][dT] | 6668.11 | 6672.1 | 73 |
| | 711 | AS | ucuugccagcagaugggcu[dT][dT] | 6662.06 | 6663.4 | 74 |
| Mito-37 | 715 | S | caucugcuggcaaggcuaa[dT][dT] | 6669.1 | 6673.5 | 75 |
| | 715 | AS | uuagccuugccagcagaug[dT][dT] | 6646.06 | 6645.3 | 76 |
| Mito-38 | 716 | S | aucugcuggcaaggcuaaa[dT][dT] | 6693.13 | 6697.2 | 77 |
| | 716 | AS | uuuagccuugccagcagau[dT][dT] | 6607.02 | 6608.1 | 78 |
| Mito-39 | 717 | S | ucugcuggcaaggcuaaga[dT][dT] | 6709.13 | 6712.2 | 79 |
| | 717 | AS | ucuuagccuugccagcaga[dT][dT] | 6606.03 | 6605.8 | 80 |
| Mito-40 | 718 | S | cugcuggcaaggcuaagaa[dT][dT] | 6732.17 | 6736.4 | 81 |
| | 718 | AS | uucuuagccuugccagcag[dT][dT] | 6582.99 | 6584.6 | 82 |
| Mito-41 | 720 | S | gcuggcaaggcuaagauua[dT][dT] | 6733.16 | 6736 | 83 |
| | 720 | AS | uaaucuuagccuugccagc[dT][dT] | 6566.99 | 6568.8 | 84 |
| Mito-42 | 721 | S | cuggcaaggcuaagauuaa[dT][dT] | 6717.16 | 6721.6 | 85 |
| | 721 | AS | uuaaucuuagccuugccag[dT][dT] | 6567.98 | 6568.9 | 86 |
| Mito-43 | 722 | S | uggcaaggcuaagauuaga[dT][dT] | 6757.19 | 6761.2 | 87 |
| | 722 | AS | ucuaaucuuagccuugcca[dT][dT] | 6527.95 | 6529.8 | 88 |
| Mito-44 | 723 | S | ggcaaggcuaagauuagaa[dT][dT] | 6780.23 | 6783.4 | 89 |
| | 723 | AS | uucuaaucuuagccuugcc[dT][dT] | 6504.91 | 6506.4 | 90 |
| Mito-45 | 725 | S | caaggcuaagauuagaaca[dT][dT] | 6724.2 | 6728.7 | 91 |
| | 725 | AS | uguucuaaucuuagccuug[dT][dT] | 6545.93 | 6547.1 | 92 |
| Mito-46 | 728 | S | ggcuaagauuagaacagca[dT][dT] | 6740.2 | 6743.2 | 93 |
| | 728 | AS | ugcuguucuaaucuuagcc[dT][dT] | 6544.94 | 6544.9 | 94 |
| Mito-47 | 773 | S | cccagauaaagguggauca[dT][dT] | 6716.17 | 6720.9 | 95 |
| | 773 | AS | ugauccaccuuuaucuggg[dT][dT] | 6583.98 | 6584.6 | 96 |

TABLE 1-continued

Certain siRNAs designed to reduce MCJ levels. Column 1 shows the siRNA ID (ID) for each of the double-strand siRNA sequences. Column 2 indicates the position in the MCJ sequence SEQ ID NO: 2, "Pos." is "Position" of the siRNA on the MCJ sequence. Column 3, "Strnd", indicates the siRNA strand of the sequence, "S" for sense strand and "AS" for antisense strand. Column 4 shows the sequences, with [dT] representing 2'-deoxythymidine-3'-phosphate. Column 5, "Calc. MW" is calculated molecular weight. Column 6, "Obs Mass" is observed Mass, with "nc" indicating not calculated.

| siRNA ID | Pos. | Strnd | Sequences (5' to 3') | Calc MW | Obs Mass | SEQ ID NO |
|---|---|---|---|---|---|---|
| Mito-48 | 774 | S | ccagauaaagguggaucua[dT][dT] | 6717.16 | 6721.9 | 97 |
| | 774 | AS | uagauccaccuuuaucugg[dT][dT] | 6567.98 | 6572.3 | 98 |
| Mito-49 | 775 | S | cagauaaagguggaucuca[dT][dT] | 6717.16 | 6721.8 | 99 |
| | 775 | AS | ugagauccaccuuuaucug[dT][dT] | 6567.98 | 6568.8 | 100 |
| Mito-50 | 780 | S | aaagguggaucuccuuaca[dT][dT] | 6654.09 | 6658.5 | 101 |
| | 780 | AS | uguaaggagauccaccuuu[dT][dT] | 6631.05 | 6632.3 | 102 |
| Mito-51 | 781 | S | aagguggaucuccuuacga[dT][dT] | 6670.09 | 6673.3 | 103 |
| | 781 | AS | ucguaaggagauccaccuu[dT][dT] | 6630.06 | 6631.3 | 104 |
| Mito-52 | 782 | S | agguggaucuccuuacgua[dT][dT] | 6647.05 | 6649.5 | 105 |
| | 782 | AS | uacguaaggagauccaccu[dT][dT] | 6653.1 | 6654.6 | 106 |
| Mito-53 | 783 | S | gguggaucuccuuacguaa[dT][dT] | 6647.05 | 6649.8 | 107 |
| | 783 | AS | uuacguaaggagauccacc[dT][dT] | 6653.1 | 6654.5 | 108 |
| Mito-54 | 784 | S | guggaucuccuuacguaga[dT][dT] | 6647.05 | 6650.7 | 109 |
| | 784 | AS | ucuacguaaggagauccac[dT][dT] | 6653.1 | 6653.1 | 110 |
| Mito-55 | 785 | S | uggaucuccuuacguagca[dT][dT] | 6607.02 | 6610.6 | ill |
| | 785 | AS | ugcuacguaaggagaucca[dT][dT] | 6693.13 | 6693.7 | 112 |
| Mito-56 | 814 | S | augaagcaaaagacuugca[dT][dT] | 6724.2 | 6728.4 | 113 |
| | 814 | AS | ugcaagucuuuugcuucau[dT][dT] | 6545.93 | 6547.2 | 114 |
| Mito-57 | 581 | S | cuggaaaccucuagaacaa[dT][dT] | 6660.1 | nc | 283 |
| | 581 | AS | uuguucuagagguuuccag[dT][dT] | 6625 | nc | 284 |
| Mito-58 | 583 | S | ggaaaccucuagaacaaga[dT][dT] | 6723.2 | nc | 285 |
| | 583 | AS | ucuuguucuagagguuucc[dT][dT] | 6561.9 | nc | 286 |
| Mito-59 | 584 | S | gaaaccucuagaacaagua[dT][dT] | 6684.1 | nc | 287 |
| | 584 | AS | uacuuguucuagagguuuc[dT][dT] | 6585.9 | nc | 288 |
| Mito-60 | 585 | S | aaaccucuagaacaaguua[dT][dT] | 6645.1 | nc | 289 |
| | 585 | AS | uaacuuguucuagagguuu[dT][dT] | 6609.9 | nc | 290 |
| Mito-61 | 586 | S | aaccucuagaacaaguuaa[dT][dT] | 6645.1 | nc | 291 |
| | 586 | AS | uuaacuuguucuagagguu[dT][dT] | 6609.9 | nc | 292 |
| Mito-62 | 587 | S | accucuagaacaaguuaua[dt][dt] | 6622.1 | nc | 293 |
| | 587 | AS | uauaacuuguucuagaggu[dT][dT] | 6633 | nc | 294 |
| Mito-64 | 589 | S | cucuagaacaaguuaucaa[dT][dT] | 6622.1 | nc | 295 |
| | 589 | AS | uugauaacuuguucuagag[dT][dT] | 6633 | nc | 296 |
| Mito-64 | 590 | S | ucuagaacaaguuaucaca[dT][dT] | 6622.1 | nc | 297 |
| | 590 | AS | ugugauaacuuguucuaga[dT][dT] | 6633 | nc | 298 |

Some embodiments of an MCJ dsRNA agent or antisense polynucleotide agent of the invention may contain one or more mismatches to the MCJ target sequence. In one embodiment, an MCJ dsRNA agent includes no more than 3 mismatches. In some embodiments of the invention, an antisense strand of an MCJ dsRNA agent contains mismatches to an MCJ target sequence that are not located in the center of the region of complementarity. In some embodiments, the antisense strand of the MCJ dsRNA agent includes 1, 2, 3, 4, or more mismatches that are within the last 5 nucleotides from either the 5' or 3' end of the region of complementarity. Methods described herein and/or methods known in the art can be used to determine whether an MCJ dsRNA agent containing a mismatch to an MCJ target sequence is effective in inhibiting the expression of the MCJ gene.

Table 2 shows DNAJC15/MCJ target sequences assigned identifying numbers MCJ-1-64. Column one shows the assigned identifier for the MCJ sequences. Column two shows the position in the DNAJC15/MCJ sequence (SEQ ID NO: 2) of the first nucleic acid in the DNAjC15/MCJ sequence shown in column three. Certain of the siRNA sequences disclosed herein were designed based on sequences MCJ-1-64. The fourth column shows the SEQ ID NO of the MCJ-1-64 sequences as SEQ ID NOs: 115-170 and 299-306, respectively. Table 2 sets forth the position and DNAJC15/MCJ sequences targeted by certain siRNAs disclosed herein.

TABLE 2

DNAJC15/MCJ target sequences

| Assigned MCJ Number | Positions | DNAJC15/MCJ Sequence | SEQ ID NO |
|---|---|---|---|
| MCJ-1 | 482 | agacgccgacgucgaccag | 115 |
| MCJ-2 | 524 | agcuguaggacuggguguu | 116 |
| MCJ-3 | 526 | cuguaggacugggguguugc | 117 |
| MCJ-4 | 527 | uguaggacuggguguugca | 118 |
| MCJ-5 | 528 | guaggacuggguguugcag | 119 |
| MCJ-6 | 537 | gguguugcagcucuugcau | 120 |
| MCJ-7 | 542 | ugcagcucuugcauuugca | 121 |
| MCJ-8 | 545 | agcucuugcauuugcaggu | 122 |
| MCJ-9 | 546 | gcucuugcauuugcagguc | 123 |
| MCJ-10 | 551 | ugcauuugcaggucgcuac | 124 |
| MCJ-11 | 552 | gcauuugcaggucgcuacg | 125 |
| MCJ-12 | 555 | uuugcaggucgcuacgcau | 126 |
| MCJ-13 | 556 | uugcaggucgcuacgcauu | 127 |
| MCJ-14 | 557 | ugcaggucgcuacgcauuu | 128 |
| MCJ-15 | 558 | gcaggucgcuacgcauuuc | 129 |
| MCJ-16 | 559 | caggucgcuacgcauuucg | 130 |
| MCJ-17 | 570 | gcauuucggaucuggaaac | 131 |
| MCJ-18 | 571 | cauuucggaucuggaaacc | 132 |
| MCJ-19 | 579 | aucuggaaaccucuagaac | 133 |
| MCJ-20 | 580 | ucuggaaaccucuagaaca | 134 |
| MCJ-21 | 588 | ccucuagaacaaguuauca | 135 |
| MCJ-22 | 632 | uccuagcuuuucauccuac | 136 |
| MCJ-23 | 635 | uagcuuuucauccuacuau | 137 |
| MCJ-24 | 636 | agcuuuucauccuacuaua | 138 |
| MCJ-25 | 637 | gcuuuucauccuacuauaa | 139 |
| MCJ-26 | 641 | uucauccuacuauaaagga | 140 |
| MCJ-27 | 642 | ucauccuacuauaaaggag | 141 |
| MCJ-28 | 643 | cauccuacuauaaaggagg | 142 |
| MCJ-29 | 669 | cagaaaaugaguaggcgag | 143 |
| MCJ-30 | 690 | gcuggucuuauuuuaggug | 144 |
| MCJ-31 | 691 | cuggucuuauuuuaggugu | 145 |
| MCJ-32 | 692 | uggucuuauuuuaggugua | 146 |
| MCJ-33 | 700 | uuuuagguguaagcccauc | 147 |
| MCJ-34 | 702 | uuagguguaagcccaucug | 148 |

TABLE 2-continued

DNAJC15/MCJ target sequences

| Assigned MCJ Number | Positions | DNAJC15/MCJ Sequence | SEQ ID NO |
|---|---|---|---|
| MCJ-35 | 704 | agguguaagcccaucugcu | 149 |
| MCJ-36 | 711 | agcccaucugcuggcaagg | 150 |
| MCJ-37 | 715 | caucugcuggcaaggcuaa | 151 |
| MCJ-38 | 716 | aucugcuggcaaggcuaag | 152 |
| MCJ-39 | 717 | ucugcuggcaaggcuaaga | 153 |
| MCJ-40 | 718 | cugcuggcaaggcuaagau | 154 |
| MCJ-41 | 720 | gcuggcaaggcuaagauua | 155 |
| MCJ-42 | 721 | cuggcaaggcuaagauuag | 156 |
| MCJ-43 | 722 | uggcaaggcuaagauuaga | 157 |
| MCJ-44 | 723 | ggcaaggcuaagauuagaa | 158 |
| MCJ-45 | 725 | caaggcuaagauuagaaca | 159 |
| MCJ-46 | 728 | ggcuaagauuagaacagcu | 160 |
| MCJ-47 | 773 | cccagauaaagguggaucu | 161 |
| MCJ-48 | 774 | ccagauaaagguggaucuc | 162 |
| MCJ-49 | 775 | cagauaaagguggaucucc | 163 |
| MCJ-50 | 780 | aaagguggaucuccuuacg | 164 |
| MCJ-51 | 781 | aagguggaucuccuuacgu | 165 |
| MCJ-52 | 782 | agguggaucuccuuacgua | 166 |
| MCJ-53 | 783 | gguggaucuccuuacguag | 167 |
| MCJ-54 | 784 | guggaucuccuuacguagc | 168 |
| MCJ-55 | 785 | uggaucuccuuacguagca | 169 |
| MCJ-56 | 814 | augaagcaaaagacuugcu | 170 |
| MCJ-57 | 581 | cuggaaaccucuagaacaa | 299 |
| MCJ-58 | 583 | ggaaaccucuagaacaagu | 300 |
| MCJ-59 | 584 | gaaaccucuagaacaaguu | 301 |
| MCJ-60 | 585 | aaaccucuagaacaaguua | 302 |
| MCJ-61 | 586 | aaccucuagaacaaguuau | 303 |
| MCJ-62 | 587 | accucuagaacaaguuauc | 304 |
| MCJ-63 | 589 | cucuagaacaaguuaucac | 305 |
| MCJ-64 | 590 | ucuagaacaaguuaucaca | 306 |

Complementarity

As used herein, unless otherwise indicated, the term "complementary," when used to describe a first nucleotide sequence (e.g., MCJ dsRNA agent sense strand or targeted MCJ mRNA) in relation to a second nucleotide sequence (e.g., MCJ dsRNA agent antisense strand or a single-stranded antisense polynucleotide), means the ability of an oligonucleotide or polynucleotide including the first nucleotide sequence to hybridize [form base pair hydrogen bonds under mammalian physiological conditions (or similar conditions in vitro)] and form a duplex or double helical structure under certain conditions with an oligonucleotide or polynucleotide including the second nucleotide sequence. Other conditions, such as physiologically relevant conditions as can be encountered inside an organism, can apply. A skilled artisan will be able to determine the set of conditions most appropriate for a test of complementarity of two sequences in accordance with the ultimate application of the hybridized nucleotides. Complementary sequences include Watson-Crick base pairs or non-Watson-Crick base pairs and include natural or modified nucleotides or nucleotide mimics, at least to the extent that the above hybridization requirements are fulfilled. Sequence identity or complementarity is independent of modification.

Complementary sequences, for example, within an MCJ dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. It will be understood that in embodiments when two oligonucleotides are designed to form, upon hybridization, one or more single stranded overhangs, such overhangs are not regarded herein as mismatches with regard to the determination of complementarity. For example, an MCJ dsRNA agent comprising one oligonucleotide 19 nucleotides in length and another oligonucleotide 20 nucleotides in length, wherein the longer oligonucleotide comprises a sequence of 19 nucleotides that is fully complementary to the shorter oligonucleotide, can yet be referred to as "fully complementary" for the purposes described herein. Thus, as used herein, "fully complementary" means that all (100%) of the bases in a contiguous sequence of a first polynucleotide will hybridize with the same number of bases in a contiguous sequence of a second polynucleotide. The contiguous sequence may comprise all or a part of a first or second nucleotide sequence.

The term "substantially complementary" as used herein means that in a hybridized pair of nucleobase sequences, at least about 85%, but not all, of the bases in a contiguous sequence of a first polynucleotide will hybridize with the same number of bases in a contiguous sequence of a second polynucleotide. The term "substantially complementary" can be used in reference to a first sequence with respect to a second sequence if the two sequences include one or more, for example at least 1, 2, 3, 4, or 5 mismatched base pairs upon hybridization for a duplex up to 15, 16, 17, 18, 19, 20, 21, 22, 23, 24, 25, 26, 27, 28, 29 or 30 base pairs (bp), while retaining the ability to hybridize under the conditions most relevant to their ultimate application, e.g., inhibition of MCJ gene expression via a RISC pathway. The term, "partially complementary" may be used herein in reference to a hybridized pair of nucleobase sequences, in which at least 75%, but not all, of the bases in a contiguous sequence of a first polynucleotide will hybridize with the same number of bases in a contiguous sequence of a second polynucleotide.

The terms "complementary," "fully complementary," "substantially complementary," and "partially complementary" are used herein in reference to the base matching between the sense strand and the antisense strand of a MCJ dsRNA agent, between the antisense strand of an MCJ dsRNA agent and a sequence of a target MCJ mRNA, or between a single-stranded antisense oligonucleotide and a sequence of a target MCJ mRNA.

As used herein, the term "substantially identical" or "substantial identity" used in reference to a nucleic acid sequence means a nucleic acid sequence comprising a sequence with at least about 85% sequence identity or more, preferably at least 90%, at least 91%, at least 92%, at least 93%, at least 94%, at least 95%, at least 96%, at least 97%, at least 98%, or at least 99%, compared to a reference sequence. Percentage of sequence identity is determined by comparing two optimally aligned sequences over a comparison window. The percentage is calculated by determining the number of positions at which the identical nucleic acid base occurs in both sequences to yield the number of matched positions, dividing the number of matched positions by the total number of positions in the window of comparison and multiplying the result by 100 to yield the percentage of sequence identity. The inventions disclosed herein encompasses nucleotide sequences substantially identical to those disclosed herein. e.g., in Tables 1, 2, and 6. In some embodiments, the sequences disclosed herein are exactly identical, or at least about 85%, 86%, 87%, 88%, 89%, 90%, 91%, 92%, 93%, 94%, 95%, 96%, 97%, 98%, or 99% percent identical to those disclosed herein, e.g., in Tables 1, 2, and 6.

As used herein, the term "strand comprising a sequence" means an oligonucleotide comprising a chain of nucleotides that is described by the sequence referred to using the standard nucleotide nomenclature. The term "double-stranded RNA" or "dsRNA," as used herein, refers to an iRNA that includes an RNA molecule or complex of molecules having a hybridized duplex region comprising two anti-parallel and substantially or fully complementary nucleic acid strands, which are referred to as having "sense" and "antisense" orientations with respect to a target MCJ RNA. The duplex region can be of any length that permits specific degradation of a desired target MCJ RNA through a RISC pathway, but will typically range from 9 to 30 base pairs in length, e.g., 15-30 base pairs in length. Considering a duplex between 9 and 30 base pairs, the duplex can be any length in this range, for example, 9, 10, 11, 12, 13, 14, 15, 16, 17, 18, 19, 20, 21, 22, 23, 24, 25, 26, 27, 28, 29, or 30, and any sub-range therein between, including, but not limited to 15-30 base pairs, 15-26 base pairs, 15-23 base pairs, 15-22 base pairs, 15-21 base pairs, 15-20 base pairs, 15-19 base pairs, 15-18 base pairs, 15-17 base pairs, 18-30 base pairs, 18-26 base pairs, 18-23 base pairs, 18-22 base pairs, 18-21 base pairs, 18-20 base pairs, 19-30 base pairs, 19-26 base pairs, 19-23 base pairs, 19-22 base pairs, 19-21 base pairs, 19-20 base pairs, 20-30 base pairs, 20-26 base pairs, 20-25 base pairs, 20-24 base pairs, 20-23 base pairs, 20-22 base pairs, 20-21 base pairs, 21-30 base pairs, 21-26 base pairs, 21-25 base pairs, 21-24 base pairs, 21-23 base pairs, or 21-22 base pairs. MCJ dsRNA agents generated in the cell by processing with Dicer and similar enzymes are generally in the range of 19-22 base pairs in length. One strand of the duplex region of an MCJ dsDNA agent comprises a sequence that is substantially complementary to a region of a target MCJ RNA. The two strands forming the duplex structure can be from a single RNA molecule having at least one self-complementary region, or can be formed from two or more separate RNA molecules. Where the duplex region is formed from two strands of a single molecule, the molecule can have a duplex region separated by a single stranded chain of nucleotides (herein referred to as a "hairpin loop") between the 3'-end of one strand and the 5'-end of the respective other strand forming the duplex structure. In some embodiments of the invention, a hairpin look comprises at least 1, 2, 3, 4, 5, 6, 7, 8, 9, 10, 11, 12, 13, 14, 15, 16, 17, 18, 19, 20, or more unpaired nucleotides. Where the two substantially complementary strands of an MCJ dsRNA agent are comprised by separate RNA molecules, those molecules need not, but can be covalently connected.

Where the two strands are connected covalently by means other than a hairpin loop, the connecting structure is referred to as a "linker." The term "siRNA" is also used herein to refer to a dsRNA agent as described herein.

In some embodiments of the invention an MCJ dsRNA agent may include a sense and antisense sequence that have no-unpaired nucleotides or nucleotide analogs at one or both terminal ends of the dsRNA agent. An end with no unpaired nucleotides is referred to as a "blunt end" and as having no nucleotide overhang. If both ends of a dsRNA agent are blunt, the dsRNA is referred to as "blunt ended." In some embodiments of the invention, a first end of a dsRNA agent is blunt, in some embodiments a second end of a dsRNA agent is blunt, and in certain embodiments of the invention, both ends of an MCJ dsRNA agent are blunt.

In some embodiments of dsRNA agents of the invention, the dsRNA does not have one or two blunt ends. In such instances there is at least one unpaired nucleotide at the end of a strand of a dsRNA agent. For example, when a 3'-end of one strand of a dsRNA extends beyond the 5'-end of the other strand, or vice versa, there is a nucleotide overhang.

A dsRNA can comprise an overhang of at least 1, 2, 3, 4, 5, 6, or more nucleotides. A nucleotide overhang can comprise or consist of a nucleotide/nucleoside analog, including a deoxynucleotide/nucleoside. It will be understood that in some embodiments a nucleotide overhang is on a sense strand of a dsRNA agent, on an antisense strand of a dsRNA agent, or on both ends of a dsRNA agent and nucleotide(s) of an overhang can be present on the 5' end, 3' end or both ends of either an antisense or sense strand of a dsRNA. In certain embodiments of the invention, one or more of the nucleotides in an overhang is replaced with a nucleoside thiophosphate.

As used herein, the term "antisense strand" or "guide strand" refers to the strand of an MCJ dsRNA agent that includes a region that is substantially complementary to an MCJ target sequence. As used herein the term "sense strand," or "passenger strand" refers to the strand of an MCJ dsRNA agent that includes a region that is substantially complementary to a region of the antisense strand of the MCJ dsRNA agent.

Modifications

In some embodiments of the invention the RNA of an MCJ siRNA agent is chemically modified to enhance stability and/or one or more other beneficial characteristics. Nucleic acids in certain embodiments of the invention may be synthesized and/or modified by methods well established in the art, for example, those described in "Current protocols in Nucleic Acid Chemistry," Beaucage, S. L. et al. (Eds.), John Wiley & Sons, Inc., New York, N.Y., USA, which is incorporated herein by reference. Modifications that can be present in certain embodiments of MCJ dsRNA agents of the invention include, for example, (a) end modifications, e.g., 5' end modifications (phosphorylation, conjugation, inverted linkages, etc.) 3' end modifications (conjugation, DNA nucleotides, inverted linkages, etc.), (b) base modifications, e.g., replacement with stabilizing bases, destabilizing bases, or bases that base pair with an expanded repertoire of partners, removal of bases (abasic nucleotides), or conjugated bases, (c) sugar modifications (e.g., at the 2' position or 4' position) or replacement of the sugar, as well as (d) backbone modifications, including modification or replacement of the phosphodiester linkages. Specific examples of RNA compounds useful in certain embodiments of MCJ dsRNA agents and MCJ antisense polynucleotide agents of the invention include, but are not limited to RNAs comprising modified backbones or no natural internucleoside linkages. As a non-limiting example, an RNA having a modified backbone may not have a phosphorus atom in the backbone. RNAs that do not have a phosphorus atom in their internucleoside backbone may be referred to as oligonucleosides. In certain embodiments of the invention, a modified RNA has a phosphorus atom in its internucleoside backbone.

It will be understood that the term "RNA molecule" or "RNA" or "ribonucleic acid molecule" encompasses not only RNA molecules as expressed or found in nature, but also analogs and derivatives of RNA comprising one or more ribonucleotide/ribonucleoside analogs or derivatives as described herein or as known in the art. The terms "ribonucleoside" and "ribonucleotide" may be used interchangeably herein. An RNA molecule can be modified in the nucleobase structure or in the ribose-phosphate backbone structure, e.g., as described herein below, and molecules comprising ribonucleoside analogs or derivatives must retain the ability to form a duplex. As non-limiting examples, an RNA molecule can also include at least one modified ribonucleoside including but not limited to a 2'-O-methyl modified nucleoside, a nucleoside comprising a 5' phosphorothioate group, a terminal nucleoside linked to a cholesteryl derivative or dodecanoic acid bisdecylamide group, a locked nucleoside, an abasic nucleoside, a 2'-deoxy-2'-fluoro modified nucleoside, a 2'-amino-modified nucleoside, 2'-alkyl-modified nucleoside, morpholino nucleoside, a phosphoramidate or a non-natural base comprising nucleoside, or any combination thereof. In some embodiments of the invention, an RNA molecule comprises at least 1, 2, 3, 4, 5, 6, 7, 8, 9, 10, 11, 12, 13, 14, 15, 16, 17, 18, 19, 20, or up to the full length of the MCJ dsRNA agent molecule's ribonucleosides that are modified ribonucleosides. The modifications need not be the same for each of such a plurality of modified ribonucleosides in an RNA molecule.

dsRNA agents or MCJ antisense polynucleotide agents of the invention may, in some embodiments comprise one or more independently selected modified nucleotides and/or one or more independently selected non-phosphodiester linkages. As used herein the term "independently selected" used in reference to a selected element, such as a modified nucleotide, non-phosphodiester linkage, etc., means that two or more selected elements can but need not be the same as each other.

As used herein, a "nucleotide base," or "nucleobase" is a heterocyclic pyrimidine or purine compound, which is a standard constituent of all nucleic acids, and includes the bases that form the nucleotides adenine (A), guanine (G), cytosine (C), thymine (T), and uracil (U). A nucleobase may further be modified to include, though not intended to be limiting: universal bases, hydrophobic bases, promiscuous bases, size-expanded bases, and fluorinated bases. The term "ribonucleotide" or "nucleotide" may be used herein to refer to an unmodified nucleotide, a modified nucleotide, or a surrogate replacement moiety. Those in the art will recognize that guanine, cytosine, adenine, and uracil can be replaced by other moieties without substantially altering the base pairing properties of an oligonucleotide comprising a nucleotide bearing such replacement moiety.

In one embodiment, modified RNAs contemplated for use in methods and compositions described herein are peptide nucleic acids (PNAs) that have the ability to form the required duplex structure and that permit or mediate the specific degradation of a target RNA via a RISC pathway. In certain embodiments of the invention, an MCJ RNA interference agent includes a single stranded RNA that interacts with a target MCJ RNA sequence to direct the cleavage of the target MCJ RNA.

Modified RNA backbones can include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those) having inverted polarity wherein the adjacent pairs of nucleoside units are linked 3'-5' to 5'-3' or 2'-5' to 5'-2'. Various salts, mixed salts and free acid forms are also included. Means of preparing phosphorus-containing linkages are routinely practiced in the art and such methods can be used to prepare certain modified MCJ dsRNA agents or certain modified MCJ antisense polynucleotide agents of the invention.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. Means of preparing modified RNA backbones that do not include a phosphorus atom are routinely practiced in the art and such methods can be used to prepare certain modified MCJ dsRNA agents or certain modified antisense polynucleotide agents of the invention.

In certain embodiments of the invention, RNA mimetics are included in MCJ dsRNAs or MCJ antisense polynucleotides, such as, but not limited to: replacement of the sugar and the internucleoside linkage, i.e., the backbone, of the nucleotide units with novel groups. In such embodiments, base units are maintained for hybridization with an appropriate MCJ nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Means of preparing RNA mimetics are routinely practiced in the art and such methods can be used to prepare certain modified MCJ dsRNA agents of the invention.

Some embodiments of the invention include RNAs with phosphorothioate backbones and oligonucleosides with heteroatom backbones, and in particular $—CH_2—NH—CH_2—$, $—CH_2—N(CH_3)—O—CH_2—$[known as a methylene (methylimino) or MMI backbone], $—CH_2—O—N(CH_3)—CH_2—$, $—CH_2—N(CH_3)—N(CH_3)—CH_2—$ and $—N(CH_3)—CH_2—$ [wherein the native phosphodiester backbone is represented as $—O—P—O—CH_2—$]. Means of preparing RNAs with phosphorothioate backbones and oligonucleosides with heteroatom backbones are routinely practiced in the art and such methods can be used to prepare certain modified MCJ dsRNA agents or certain MCJ antisense polynucleotide agents of the invention.

Modified RNAs can also contain one or more substituted sugar moieties. MCJ dsRNAs or MCJ antisense polynucleotides of the invention may comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Exemplary suitable modifications include $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an MCJ dsRNA agent, or a group for improving the pharmacodynamic properties of an MCJ dsRNA agent or MCJ antisense polynucleotide agent, and other substituents having similar properties. In some embodiments, the modification includes a 2'-methoxyethoxy ($2'-O—CH_2CH_2OCH_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethyl aminooxyethoxy, i.e., a $O(CH_2)_2ON(CH_3)_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., $2'-O—CH_2—O—CH_2—N(CH_2)_2$. Means of preparing modified RNAs such as those described are routinely practiced in the art and such methods can be used to prepare certain modified MCJ dsRNA agents of the invention.

Other modifications include 2'-methoxy ($2'-OCH_3$), 2'-aminopropoxy ($2'-OCH_2CH_2CH_2NH_2$) and 2'-fluoro (2'-F). Similar modifications can also be made at other positions on the RNA of an MCJ dsRNA agent or MCJ antisense polynucleotide agent of the invention, particularly the 3' position of the sugar on the 3' terminal nucleotide or in 2'-5' linked MCJ dsRNAs or MCJ antisense polynucleotides, and the 5' position of 5' terminal nucleotide. MCJ dsRNA agents or MCJ antisense polynucleotide agents may also have sugar mimetics such as cyclobutyl moieties in place of the pentofuranosyl sugar. Means of preparing modified RNAs such as those described are routinely practiced in the art and such methods can be used to prepare certain modified MCJ dsRNA agents or MCJ antisense polynucleotide agents of the invention.

An MCJ dsRNA agent or MCJ antisense polynucleotide agent may, in some embodiments, include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Additional nucleobases that may be included in certain embodiments of MCJ dsRNA agents of the invention are known in the art, see for example: Modified Nucleosides in Biochemistry, Biotechnology and Medicine, Herdewijn, P. Ed. Wiley-VCH, 2008; The Concise Encyclopedia Of Polymer Science And Engineering, pages 858-859, Kroschwitz, J. L, Ed. John Wiley & Sons, 1990, Englisch et al., Angewandte Chemie, International Edition, 1991, 30, 613, Sanghvi, Y S., Chapter 15, dsRNA Research and Applications, pages 289-302, Crooke, S. T. and Lebleu, B., Ed., CRC Press, 1993. Means of preparing dsRNAs or MCJ antisense polynucleotides that comprise nucleobase modifications and/or substitutions such as those described herein are routinely practiced in the art and such methods can be used to prepare certain modified MCJ dsRNA agents or MCJ antisense polynucleotide agents of the invention.

Certain embodiments of MCJ dsRNA agents or MCJ antisense polynucleotide agents of the invention include RNA modified to include one or more locked nucleic acids (LNA). A locked nucleic acid is a nucleotide with a modified ribose moiety comprising an extra bridge connecting the 2' and 4' carbons. This structure effectively "locks" the ribose in the 3'-endo structural conformation. The addition of locked nucleic acids in an MCJ dsRNA agent or MCJ antisense polynucleotide agent of the invention may increase stability in serum, and to reduce off-target effects (Elmen, J. et al., (2005) Nucleic Acids Research 33(1):439-447; Mook, O R. et al., (2007) Mol Canc Ther 6(3):833-843; Grunweller, A. et al., (2003) Nucleic Acids Research 31(12):3185-3193). Means of preparing dsRNA agents or MCJ antisense polynucleotide agents that comprise locked nucleic acid(s) are routinely practiced in the art and such methods can be used to prepare certain modified MCJ dsRNA agents of the invention.

Another modification that may be included in the RNA of certain embodiments of MCJ dsRNA agents or MCJ antisense polynucleotide agents of the invention, comprises chemically linking to the RNA one or more ligands, moieties or conjugates that enhance one or more characteristics of the MCJ dsRNA agent or MCJ antisense polynucleotide agent, respectively. Non-limiting examples of characteristics that may be enhanced are: MCJ dsRNA agent or MCJ antisense polynucleotide agent activity, cellular distribution, delivery of an MCJ dsRNA agent or MCJ antisense polynucleotide agent, pharmacokinetic properties of an MCJ dsRNA agent or MCJ antisense polynucleotide agent, and cellular uptake of the MCJ dsRNA agent or MCJ antisense polynucleotide agent. In some embodiments of the invention, an MCJ dsRNA agent or MCJ antisense polynucleotide agent comprises one or more targeting groups or linking groups, which in certain embodiments of MCJ dsRNA agents of the invention are conjugated to the sense strand. A non-limiting example of a targeting group is a compound comprising N-acetyl-galactosamine (GalNAc). The terms "targeting group", "targeting agent", "linking agent" and "targeting ligand" may be used interchangeably herein. In certain embodiments of the invention an MCJ dsRNA agent comprises a targeting group that is conjugated to the 5'-terminal end of the sense strand. In some embodiments of the invention, an MCJ dsRNA agent or MCJ antisense polynucleotide agent comprises a targeting group that comprises GalNAc. In certain embodiments of the invention an MCJ dsRNA agent does not include a targeting group that is conjugated to the 5'-terminal end of the sense strand. In certain embodiments of the invention an MCJ dsRNA agent does not include a GalNAc targeting group conjugated to the 5'-terminal end of the sense strand.

Additional targeting and linking agents are well known in the art, for example, targeting and linking agents that may be used in certain embodiments of the invention include but are not limited to lipid moieties such as a cholesterol moiety (Letsinger et al., Proc. Natl. Acid. Sci. USA, 1989, 86: 6553-6556), cholic acid (Manoharan et al., Biorg. Med. Chem. Let., 1994, 4:1053-1060), a thioether, e.g., beryl-S-tritylthiol (Manoharan et al., Ann. N.Y. Acad. Sci., 1992, 660:306-309; Manoharan et al., Biorg. Med. Chem. Let., 1993, 3:2765-2770), a thiocholesterol (Oberhauser et al., Nucl. Acids Res., 1992, 20:533-538), an aliphatic chain, e.g., dodecandiol or undecyl residues (Saison-Behmoaras et al., EMBO J, 1991, 10:1111-1118; Kabanov et al., FEBS Lett., 1990, 259:327-330; Svinarchuk et al., Biochimie, 1993, 75:49-54), a phospholipid, e.g., di-hexadecyl-rac-glycerol or triethyl-ammonium 1,2-di-O-hexadecyl-rac-glycero- 3-phosphonate (Manoharan et al., Tetrahedron Lett., 1995, 36:3651-3654; Shea et al., Nucl. Acids Res., 1990, 18:3777-3783), a polyamine or a polyethylene glycol chain (Manoharan et al., Nucleosides & Nucleotides, 1995, 14:969-973), or adamantane acetic acid (Manoharan et al., Tetrahedron Lett., 1995, 36:3651-3654), a palmityl moiety (Mishra et al., Biochim. Biophys. Acta, 1995, 1264:229-237), or an octadecylamine or hexylamino-carbonyloxycholesterol moiety (Crooke et al., J. Pharmacol. Exp. Ther., 1996, 277:923-937).

Certain embodiments of a composition comprising an MCJ dsRNA agent or MCJ antisense polynucleotide agent may comprise a ligand that alters distribution, targeting, or etc. of the MCJ dsRNA agent. In some embodiments of a composition comprising an MCJ dsRNA agent or MCJ antisense polynucleotide agent of the invention, the ligand increases affinity for a selected target, e.g., molecule, cell or cell type, compartment, e.g., a cellular or organ compartment, tissue, organ or region of the body, as, e.g., compared to a species absent such a ligand. A ligands useful in a composition and/or method of the invention may be a naturally occurring substance, such as a protein (e.g., human serum albumin (HSA), low-density lipoprotein (LDL), or globulin); a carbohydrate (e.g., a dextran, pullulan, chitin, chitosan, inulin, cyclodextrin or hyaluronic acid); or a lipid. A ligand may also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

A ligand included in a composition and/or method of the invention may comprise a targeting group, non-limiting examples of which are a cell or tissue targeting agent, e.g., a lectin, glycoprotein, lipid or protein, e.g., an antibody that binds to a specified cell type such as a kidney cell or a liver cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucosamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid, O3-(oleoyl) lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]2, polyamino, alkyl, substituted alkyl, radiolabeled markers, enzymes, haptens (e.g., biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

A ligand included in a composition and/or method of the invention may be a protein, e.g., glycoprotein, or peptide, for example a molecule with a specific affinity for a co-ligand, or an antibody, for example an antibody, that binds to a specified cell type such as a cancer cell, endothelial cell, cardiac cell, or bone cell. A ligand useful in an embodiment of a composition and/or method of the invention can be a hormone or hormone receptor. A ligand useful in an embodiment of a composition and/or method of the invention can be a lipid, lectin, carbohydrates, vitamin, cofactos, multivalent lactose, multivalent galactose, N-acetyl-galactosamine, N-acetyl-gulucosamine multivalent mannose, or multivalent fucose. A ligand useful in an embodiment of a composition and/or method of the invention can be a substance that can increase uptake of the MCJ dsRNA agent or MCJ antisense polynucleotide agent into the cell, for example, by disrupting the cell's cytoskeleton, e.g., by disrupting the cell's microtubules, microfilaments, and/or intermediate filaments. Non-limiting examples of this type of agent are: taxon, vincristine, vinblastine, cytochalasin, nocodazole, japlakinolide, latrunculin A, phalloidin, swinholide A, indanocine, and myoservin.

In some embodiments, a ligand attached to an MCJ dsRNA agent or MCJ antisense polynucleotide agent of the invention functions as a pharmacokinetic (PK) modulator. An example of a PK modulator that may be used in compositions and methods of the invention includes but is not limited to: a lipophiles, a bile acid, a steroid, a phospholipid analogue, a peptide, a protein binding agent, PEG, a vitamin, cholesterol, a fatty acid, cholic acid, lithocholic acid, dialkylglycerides, diacylglyceride, a phospholipid, a sphingolipid, naproxen, ibuprofen, vitamin E, biotin, an aptamer that binds a serum protein, etc. Oligonucleotides comprising a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone may also be used in compositions and/or methods of the invention as ligands.

MCJ dsRNA Agent Compositions

In some embodiments of the invention, an MCJ dsRNA agent or MCJ antisense polynucleotide agent is in a composition. A composition of the invention may include one or more MCJ dsRNA agent or MCJ antisense polynucleotide agent and optionally one or more of a pharmaceutically acceptable carrier, a delivery agent, a targeting agent, detectable label, etc. A non-limiting example of a targeting agent that may be useful according to some embodiments of methods of the invention is an agent that directs an MCJ dsRNA agent or MCJ antisense polynucleotide agent of the invention to and/or into a cell to be treated. A targeting agent of choice will depend upon such elements as: the nature of the MCJ-associated disease or condition, and on the cell type being targeted. In a non-limiting example, in some embodiments of the invention it may be desirable to target an MCJ dsRNA agent or MCJ antisense polynucleotide agent to and/or into a liver cell. It will be understood that in some embodiments of methods of the invention, a therapeutic agent comprises a MCJ dsRNA agent or MCJ antisense polynucleotide agent with only a delivery agent, such as a delivery agent comprising N-Acetylgalactosamine (GalNAc), without any additional attached elements. For example, in some aspects of the invention an MCJ dsRNA agent or MCJ antisense polynucleotide agent may be attached to a delivery agent comprising GalNAc and included in a composition comprising a pharmaceutically acceptable carrier and administered to a cell or subject without any detectable labels, or targeting agents, etc. attached to the MCJ dsRNA agent.

In cases where an MCJ dsRNA agent or MCJ antisense polynucleotide agent of the invention is administered with and/or attached to one or more delivery agents, targeting agents, labeling agents, etc. a skilled artisan will be aware of and able to select and use suitable agents for use in methods of the invention. Labeling agents may be used in certain methods of the invention to determine the location of an MCJ dsRNA agent or MCJ antisense polynucleotide agent in cells and tissues and may be used to determine a cell, tissue, or organ location of a treatment composition comprising an MCJ dsRNA agent MCJ antisense polynucleotide agent that has been administered in methods of the invention. Procedures for attaching and utilizing labeling agents such as enzymatic labels, dyes, radiolabels, etc. are well known in the art.

Delivery of dsRNA Agents and MCJ Antisense Polynucleotide Agents

Certain embodiments of methods of the invention, includes delivery of an MCJ dsRNA agent or a MCJ antisense polynucleotide agent into a cell. As used herein the term, "delivery" means facilitating or effecting uptake or absorption into the cell. Absorption or uptake of a dsRNA agent or MCJ antisense polynucleotide agent can occur through unaided diffusive or active cellular processes, or by use of delivery agents, targeting agents, etc. that may be associated with an MCJ dsRNA agent or MCJ antisense polynucleotide agent of the invention. Delivery means that are suitable for use in methods of the invention include, but are not limited to: in vivo delivery, in which an MCJ dsRNA agent or MCJ antisense polynucleotide agent is in injected into a tissue site or administered systemically. In some embodiments of the invention, an MCJ dsRNA agent or MCJ antisense polynucleotide agent is attached to a delivery agent. Art-recognized difficulties with siRNA delivery have been overcome using a number of delivery technologies that can be used for successful in vivo delivery of therapeutic siRNAs.

Non-limiting examples of methods that can be used to deliver MCJ siRNA agents to cells, tissues and/or subjects include: siRNA-GalNAc conjugates, SAMiRNA technology, LNP-based delivery methods, and naked siRNA delivery. These and other delivery methods have been used successfully in the art to deliver therapeutic siRNA agents for treatment of various diseases and conditions, such as but not limited to: liver diseases, acute intermittent porphyria (AIP), hemophilia, pulmonary fibrosis, etc. Details of various siRNA delivery means are found in publications such as: Nikam, R. R. & K. R. Gore (2018) Nucleic Acid Ther, 28 (4), 209-224 August 2018; Springer A. D. & S. F. Dowdy (2018) Nucleic Acid Ther. June 1; 28(3): 109-118; Lee, K. et al., (2018) Arch Pharm Res, 41(9), 867-874; and Nair, J. K. et al., (2014) J. Am. Chem. Soc. 136:16958-16961, the content each of which is incorporated by reference herein.

Some embodiments of the invention comprise use of lipid nanoparticles (LNPs) to deliver an MCJ dsRNA agent or MCJ antisense polynucleotide agent of the invention to a cell, tissue, and/or subject. LNPs are routinely used for in vivo delivery of siRNA agents, including therapeutic siRNA agents. One benefit of using an LNP or other siRNA delivery agent is an increased stability of the siRNA agent when it is delivered to a subject using the LNP or other delivery agent. In some embodiments of the invention an LNP comprises a cationic LNP that is loaded with one or more siRNA molecules, for example, one or more MCJ siRNA molecules of the invention. The LNP comprising the MCJ siRNA molecule(s) is administered to a subject, the LNPs and their attached MCJ siRNA are taken up by cells via endocytosis, their presence results in release of RNAi trigger molecules, which mediate RNAi.

Another non-limiting example of a delivery agent that may be used in embodiments of the invention to delivery an MCJ dsRNA agent of the invention to a cell, tissue and/or subject is an agent comprising GalNAc that is attached to an MCJ dsRNA agent of the invention and delivers the MCJ dsRNA agent to a cell, tissue, and/or subject. Examples of certain additional delivery agents comprising GalNAc that can be used in certain embodiments of methods and composition of the invention are disclosed in PCT Application: WO2020191183A1. A non-limiting example of a GalNAc targeting ligand that can be used in compositions and methods of the invention to deliver an siMCJ to a cell is a targeting ligand cluster referred to herein as: MITO-F. MITO-F is illustrated below with an siRNA attached (far right). As indicated below "X" is either Oxygen (O) or Sulfur (S).

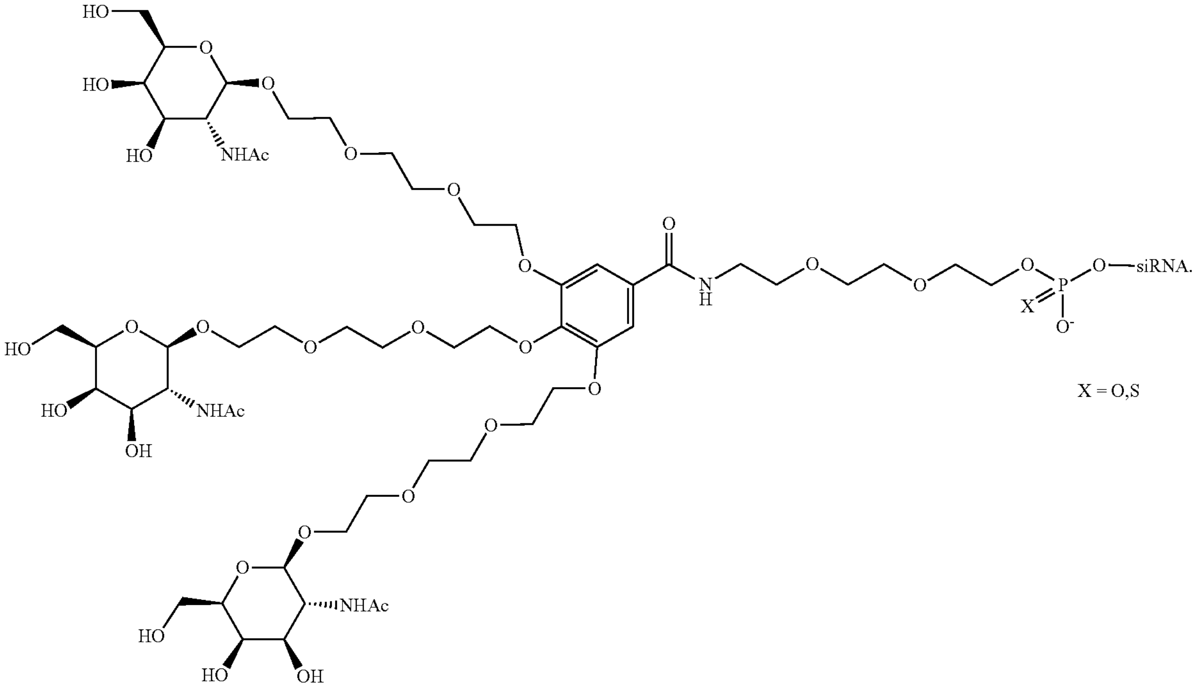

X = O,S

In some embodiments of the invention, in vivo delivery can also be by a beta-glucan delivery system, such as those described in U.S. Pat. Nos. 5,032,401 and 5,607,677, and U.S. Publication No. 2005/0281781, which are hereby incorporated by reference in their entirety. In vitro introduction of an MCJ siRNA agent into a cell may also be done using art-known methods such as electroporation and lipofection. In certain embodiments of methods of the invention, an MCJ dsRNA is delivered without a targeting agent. These siRNAs may be delivered as "naked" RNA molecules. As a non-limiting example, an MCJ dsRNA of the invention may be administered to a subject to treat an MCJ-associated disease or condition in the subject, such as a kidney disease, in a pharmaceutical composition comprising the siRNA, but not including a targeting agent such as a GalNAc targeting agent.

In addition to certain delivery means described herein, it will be understood that siRNA delivery means, such as but not limited to those described herein and those used in the art, can be used in conjunction with embodiments of MCJ siRNA agents and treatment methods described herein.

MCJ dsRNA agents and MCJ antisense polynucleotide agents of the invention may be administered to a subject in an amount and manner effective to reduce a level and activity of MCJ polypeptide in a cell and/or subject. In some embodiments of methods of the invention one or more MCJ dsRNA agents or MCJ antisense polynucleotide agents are administered to a cell and/or subject to treat a disease or condition associated with MCJ expression and activity. Methods of the invention, in some embodiments, include administering one or more MCJ dsRNA agents or MCJ antisense polynucleotide agents to a subject in need of such treatment to reduce a disease or condition associated with MCJ expression in the subject. MCJ dsRNA agents or MCJ antisense polynucleotide agents of the invention can be administered to reduce MCJ expression and/or activity in one more of in vitro, ex vivo, and in vivo cells.

In some embodiments of the invention, a level, and thus an activity, of MCJ polypeptide in a cell is reduced by delivering (e.g. introducing) an MCJ dsRNA agent or MCJ antisense polynucleotide agent into a cell. Targeting agents and methods may be used to aid in delivery of a MCJ dsRNA agent or MCJ antisense polynucleotide agent to a specific cell type, cell subtype, organ, spatial region within a subject, and/or to a sub-cellular region within a cell. An MCJ dsRNA agent or MCJ antisense polynucleotide agent can be administered in certain methods of the invention singly or in combination with one or more additional compounds. In some embodiments 2, 3, 4, or more independently selected MCJ dsRNA agents or MCJ antisense polynucleotide agents are administered. In certain embodiments of the invention, an MCJ dsRNA agent or MCJ antisense polynucleotide agent is administered in conjunction with one or more non-MCJ dsRNA agent, MCJ antisense polynucleotide agent, therapeutic agent, or therapeutic activity. An MCJ dsRNA agent or MCJ antisense polynucleotide agent of the invention administered to a cell or subject to treat an MCJ-associated disease or condition may act in a synergistic manner with one or more other therapeutic agents or activities and increase the effectiveness of the one or more therapeutic agents or activities and/or to increase the effectiveness of the MCJ dsRNA agent or MCJ antisense polynucleotide agent at treating an MCJ-associated disease or condition.

Treatment methods of the invention that include administration of an MCJ dsRNA agent or MCJ antisense polynucleotide agent can be used prior to the onset of an MCJ-associated disease or condition and/or when an MCJ-associated disease or condition is present, including at an early stage, mid-stage, and late stage of the disease or condition and all times before and after any of these stages. Methods of the invention may also be to treat subjects who have previously been treated for an MCJ-associated disease or condition with one or more other therapeutic agents and/or therapeutic activities that were not successful, were minimally successful, and/or are no longer successful at treating the MCJ-associated disease or condition in the subject.

Vector Encoded dsRNAs

In certain embodiments of the invention, an MCJ dsRNA agent can be delivered into a cell using a vector. MCJ dsRNA agent transcription units can be included in a DNA or RNA vector. Prepare and use of such vectors encoding transgenes for delivering sequences into a cell and or subject are well known in the art. Vectors can be used in methods of the invention that result in transient expression of MCJ dsRNA, for example for at least 1, 2, 3, 4, 5, 6, 7, 8, 9, 10 or more hours, 1, 2, 3, 4, 5, 6, 7, 8, 9, 10 or more weeks. The length of the transient expression can be determined using routine methods based on elements such as, but not limited to the specific vector construct selected and the target cell and/or tissue. Such transgenes can be introduced as a linear construct, a circular plasmid, or a viral vector, which can be an integrating or non-integrating vector. The transgene can also be constructed to permit it to be inherited as an extrachromosomal plasmid (Gassmann, et al., Proc. Natl. Acad. Sci. USA (1995) 92:1292).

An individual strand or strands of an MCJ dsRNA agent can be transcribed from a promoter on an expression vector. Where two separate strands are to be expressed to generate, for example, a dsRNA, two separate expression vectors can be co-introduced to a cell using means such as transfection or infection. In certain embodiments each individual strand of an MCJ dsRNA agent of the invention can be transcribed by promoters that are both included on the same expression vector. In certain embodiments of the invention an MCJ dsRNA agent is expressed as inverted repeat polynucleotides joined by a linker polynucleotide sequence such that the MCJ dsRNA agent has a stem and loop structure.

Non-limiting examples of RNA expression vectors are DNA plasmids or viral vectors. Expression vectors useful in embodiments of the invention can be compatible with eukaryotic cells. Eukaryotic cell expression vectors are routinely used in the art and are available from a number of commercial sources. Delivery of MCJ dsRNA expressing vectors can be systemic, such as by intravenous or intramuscular administration, by administration to target cells ex-planted from a subject followed by reintroduction into the subject, or by any other means that allows for introduction into a desired target cell.

Viral vector systems that may be included in an embodiment of a method of the include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Constructs for the recombinant expression of an MCJ dsRNA agent may include regulatory elements, such as promoters, enhancers, etc., which may be selected to provide constitutive or regulated/inducible expression. Viral vector systems, and the use of promoters and enhancers, etc. are routine in the art and can be used in conjunction with methods and compositions described herein.

Certain embodiments of the invention include use of viral vectors for delivery of MCJ dsRNA agents into cells. Numerous adenovirus-based delivery systems are routinely used in the art for deliver to, for example, lung, liver, the central nervous system, endothelial cells, and muscle. Non-limiting examples of viral vectors that may be used in methods of the invention are: AAV vectors, a pox virus such as a vaccinia virus, a Modified Virus Ankara (MVA), NYVAC, an avipox such as fowl pox or canary pox.

Certain embodiments of the invention include methods of delivering MCJ dsRNA agents into cells using a vector and such vectors may be in a pharmaceutically acceptable carrier that may, but need not, include a slow release matrix in which the gene delivery vehicle is imbedded. In some embodiments, a vector for delivering an MCJ dsRNA can be produced from a recombinant cell, and a pharmaceutical composition of the invention may include one or more cells that produced the MCJ dsRNA delivery system.

Pharmaceutical Compositions Containing MCJ dsRNA or MCJ Antisense Polynucleotide Agents Certain embodiments of the invention include use of pharmaceutical compositions containing an MCJ dsRNA agent or MCJ antisense polynucleotide agent and a pharmaceutically acceptable carrier. The pharmaceutical composition containing the MCJ dsRNA agent or MCJ antisense polynucleotide agent can be used in methods of the invention to reduce MCJ gene expression and MCJ activity in a cell and is useful to treat an MCJ-associated disease or condition. Such pharmaceutical compositions can be formulated based on the mode of delivery. Non-limiting examples of formulations for modes of delivery are: a composition formulated for subcutaneous delivery, a composition formulated for systemic administration via parenteral delivery, a composition formulated for intravenous (IV) delivery, a composition formulated for intrathecal delivery, a composition formulated for direct delivery into brain, etc. Administration of a pharmaceutic composition of the invention to deliver an MCJ dsRNA agent or MCJ antisense polynucleotide agent into a cell may be done using one or more means such as: topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration. An MCJ dsRNA agent or MCJ antisense polynucleotide agent can also be delivered directly to a target tissue, for example directly into the liver, directly into a kidney, etc. It will be understood that "delivering an MCJ dsRNA agent" or "delivering an MCJ antisense polynucleotide agent" into a cell encompasses delivering an MCJ dsRNA agent or MCJ antisense polynucleotide agent, respectively, directly as well as expressing an MCJ dsRNA agent in a cell from an encoding vector that is delivered into a cell, or by any suitable means with which the MCJ dsRNA or MCJ antisense polynucleotide agent becomes present in a cell. Preparation and use of formulations and means for delivering inhibitory RNAs are well known and routinely used in the art.

As used herein, a "pharmaceutical composition" comprises a pharmacologically effective amount of an MCJ dsRNA agent or MCJ antisense polynucleotide agent of the invention and a pharmaceutically acceptable carrier. The term "pharmaceutically acceptable carrier" refers to a carrier for administration of a therapeutic agent. Such carriers include, but are not limited to, saline, buffered saline, dextrose, water, glycerol, ethanol, and combinations thereof. The term specifically excludes cell culture medium. For drugs administered orally, pharmaceutically acceptable carriers include, but are not limited to pharmaceutically acceptable excipients such as inert diluents, disintegrating agents, binding agents, lubricating agents, sweetening agents, flavoring agents, coloring agents and preservatives. Suitable inert diluents include sodium and calcium carbonate, sodium and calcium phosphate, and lactose, while corn starch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract. Agents included in drug formulations are described further herein below.

As used herein terms such as: "pharmacologically effective amount," "therapeutically effective amount" and "effective amount" refers to that amount of an MCJ dsRNA agent or MCJ antisense polynucleotide agent of the invention to produce the intended pharmacological, therapeutic or preventive result. For example, if a given clinical treatment is considered effective when there is at least a 10% reduction in a measurable parameter associated with a disease or disorder, a therapeutically effective amount of a drug for the treatment of that disease or disorder is the amount necessary to effect at least a 10% reduction in that parameter. For example, a therapeutically effective amount of an MCJ dsRNA agent or MCJ antisense polynucleotide agent can reduce MCJ polypeptide levels by at least 10%.

Effective Amounts

Methods of the invention, in some aspects comprise contacting a cell with an MCJ dsRNA agent or MCJ antisense polynucleotide agent in an effective amount to reduce MCJ gene expression in the contacted cell. Certain embodiments of methods of the invention comprise administering an MCJ dsRNA agent or MCJ antisense polynucleotide agent to a subject in an amount effective to reduce MCJ gene expression and treat an MCJ-associated disease or condition in the subject. An "effective amount" used in terms of reducing expression of MCJ and/or for treating an MCJ-associated disease or condition, is an amount necessary or sufficient to realize a desired biologic effect. For example, an effective amount of an MCJ dsRNA agent or MCJ antisense polynucleotide agent to treat an MCJ-associated disease or condition could be that amount necessary to (i) slow or halt progression of the disease or condition; or (ii) reverse, reduce, or eliminate one or more symptoms of the disease or condition. In some aspects of the invention, an effective amount is that amount of an MCJ dsRNA agent or MCJ antisense polynucleotide agent that when administered to a subject in need of a treatment of an MCJ-associated disease or condition, results in a therapeutic response that prevents and/or treats the disease or condition. According to some aspects of the invention, an effective amount is that amount of an MCJ dsRNA agent or MCJ antisense polynucleotide agent of the invention that when combined or co-administered with another therapeutic treatment for an MCJ-associated disease or condition, results in a therapeutic response that prevents and/or treats the disease or condition. In some embodiments of the invention, a biologic effect of treating a subject with an MCJ dsRNA agent or MCJ antisense polynucleotide agent of the invention may be the amelioration and or absolute elimination of symptoms resulting from the MCJ-associated disease or condition. In some embodiments of the invention, a biologic effect is the complete abrogation of the MCJ-associated disease or condition, as evidenced for example, by a diagnostic test that indicates the subject is free of the MCJ-associated disease or condition. A non-limiting example of a physiological symptom that may be detected includes a reduction in lipid accumulation in liver of a subject following administration of an agent of the invention. Additional art-known means of assessing the status of an MCJ-associated disease or condition can be used to determine an effect of an agent and/or methods of the invention on an MCJ-associated disease or condition.

Typically an effective amount of an MCJ dsRNA agent or MCJ antisense polynucleotide agent to decrease MCJ polypeptide activity to a level to treat an MCJ-associated disease or condition will be determined in clinical trials, establishing an effective dose for a test population versus a control population in a blind study. In some embodiments, an effective amount will be that results in a desired response, e.g., an amount that diminishes an MCJ-associated disease or condition in cells, tissues, and/or subjects with the disease or condition. Thus, an effective amount of an MCJ dsRNA agent or MCJ antisense polynucleotide agent to treat an MCJ-associated disease or condition that can be treated by reducing MCJ polypeptide activity may be the amount that when administered decreases the amount of MCJ polypeptide activity in the subject to an amount that is less than the amount that would be present in the cell, tissue, and/or subject without the administration of the MCJ dsRNA agent or MCJ anti sense polynucleotide agent. In certain aspects of the invention the level of MCJ polypeptide activity, and/or MCJ gene expression present in a cell, tissue, and/or subject that has not been contacted with or administered an MCJ dsRNA agent or MCJ antisense polynucleotide agent of the invention is referred to as a "control" amount. In some embodiments of methods of the invention a control amount for a subject is a pre-treatment amount for the subject, in other words, a level in a subject before administration of an MCJ agent can be a control level for that subject and compared to a level of MCJ polypeptide activity and/or MCJ gene expression in the subject following siRNA administered to the subject. In the case of treating an MCJ-associated disease or condition the desired response may be reducing or eliminating one or more symptoms of the disease or condition in the cell, tissue, and/or subject. The reduction or elimination may be temporary or may be permanent. It will be understood that the status of an MCJ-associated disease or condition can be monitored using methods of determining MCJ polypeptide activity, MCJ gene expression, symptom evaluation, clinical testing, etc. In some aspects of the invention, a desired response to treatment of an MCJ-associated disease or condition is delaying the onset or even preventing the onset of the disease or condition.

An effective amount of a compound that decreases MCJ polypeptide activity may also be determined by assessing physiological effects of administration of an MCJ dsRNA agent or MCJ antisense polynucleotide agent on a cell or subject, such as a decrease of an MCJ-associated disease or condition following administration. Assays and/or symptomatic monitoring of a subject can be used to determine efficacy of an MCJ dsRNA agent or MCJ antisense polynucleotide agent of the invention, which may be administered in a pharmaceutical compound of the invention, and to determine the presence or absence of a response to the treatment. A non-limiting example, is that one or more art-known tests of liver function can be used to determine the status of the MCJ-associated liver disease or condition in a subject before and after treatment of the subject with an MCJ dsRNA agent of the invention.

It will be understood that the amount of an MCJ dsRNA agent or MCJ antisense polynucleotide agent administered to a subject can be modified based, at least in part, on such determinations of disease and/or condition status. The amount of a treatment may be varied for example by increasing or decreasing the amount of an MCJ-dsRNA agent or MCJ antisense polynucleotide agent, by changing the composition in which the MCJ dsRNA agent or MCJ antisense polynucleotide agent, respectively, is administered, by changing the route of administration, by changing the dosage timing and so on. The effective amount of an MCJ dsRNA agent or MCJ anti sense polynucleotide agent will vary with the particular condition being treated, the age and physical condition of the subject being treated; the severity of the condition, the duration of the treatment, the nature of the concurrent therapy (if any), the specific route of administration, and additional factors within the knowledge and expertise of the health practitioner. For example, an effective amount may depend upon the desired level of MCJ polypeptide activity and or MCJ gene expression that is effective to treat the MCJ-associated disease or condition. A skilled artisan can empirically determine an effective amount of a particular MCJ dsRNA agent or MCJ antisense polynucleotide agent of the invention for use in methods of the invention without necessitating undue experimentation. Combined with the teachings provided herein, by selecting from among various MCJ dsRNA agents or MCJ antisense polynucleotide agents of the invention, and weighing factors such as potency, relative bioavailability, patient body weight, severity of adverse side-effects and preferred mode of administration, an effective prophylactic or therapeutic treatment regimen can be planned that is effective to treat the particular subject. As used in embodiments of the invention, an effective amount of an MCJ dsRNA agent or MCJ antisense polynucleotide agent of the invention can be that amount that when contacted with a cell results in a desired biological effect in the cell.

It will be recognized that MCJ gene silencing may be determined in any cell expressing MCJ, either constitutively or by genomic engineering, and by any appropriate assay. In some embodiments of the invention, MCJ gene expression is reduced by at least 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, or 100% by administration of an MCJ dsRNA agent of the invention. In some embodiments of the invention, MCJ gene expression is reduced by at between 5% and 10%, 5% and 25%, 10% and 50%, 10% and 75%, 25% and 75%, 25% and 100%, or 50% and 100% by administration of an MCJ dsRNA agent of the invention.

Dosing

MCJ dsRNA agents and MCJ antisense polynucleotide agents are delivered in pharmaceutical compositions in dosages sufficient to inhibit expression of MCJ genes. In certain embodiments of the invention, a dose of MCJ dsRNA agent or MCJ antisense polynucleotide agent is in a range of 0.01 to 200.0 milligrams per kilogram body weight of the recipient per day, generally in the range of 1 to 50 mg per kilogram body weight, 5 to 40 mg/kg body weight, 10 to 30 mg/kg body weight, 1 to 20 mg/kg body weight, 1 to 10 mg/kg body weight, 4 to 15 mg/kg body weight per day, inclusive. For example, the MCJ dsRNA agent or MCJ antisense polynucleotide agent can be administered in an amount that is from about 0.01 mg/kg, 0.05 mg/kg, 0.1 mg/kg, 0.2 mg/kg, 0.3 mg/kg, 0.4 mg/kg, 0.5 mg/kg, 1 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2 mg/kg, 2.1 mg/kg, 2.2 mg/kg, 2.3 mg/kg, 2.4 mg/kg, 2.5 mg/kg, 2.6 mg/kg, 2.7 mg/kg, 2.8 mg/kg, 2.9 mg/kg, 3.0 mg/kg, 3.1 mg/kg, 3.2 mg/kg, 3.3 mg/kg, 3.4 mg/kg, 3.5 mg/kg, 3.6 mg/kg, 3.7 mg/kg, 3.8 mg/kg, 3.9 mg/kg, 4 mg/kg, 4.1 mg/kg, 4.2 mg/kg, 4.3 mg/kg, 4.4 mg/kg, 4.5 mg/kg, 4.6 mg/kg, 4.7 mg/kg, 4.8 mg/kg, 4.9 mg/kg, 5 mg/kg, 5.1 mg/kg, 5.2 mg/kg, 5.3 mg/kg, 5.4 mg/kg, 5.5 mg/kg, 5.6 mg/kg, 5.7 mg/kg, 5.8 mg/kg, 5.9 mg/kg, 6 mg/kg, 6.1 mg/kg, 6.2 mg/kg, 6.3 mg/kg, 6.4 mg/kg, 6.5 mg/kg, 6.6 mg/kg, 6.7 mg/kg, 6.8 mg/kg, 6.9 mg/kg, 7 mg/kg, 7.1 mg/kg, 7.2 mg/kg, 7.3 mg/kg, 7.4 mg/kg, 7.5 mg/kg, 7.6 mg/kg, 7.7 mg/kg, 7.8 mg/kg, 7.9 mg/kg, 8 mg/kg, 8.1 mg/kg, 8.2 mg/kg, 8.3 mg/kg, 8.4 mg/kg, 8.5 mg/kg, 8.6 mg/kg, 8.7 mg/kg, 8.8 mg/kg, 8.9 mg/kg, 9 mg/kg, 9.1 mg/kg, 9.2 mg/kg, 9.3 mg/kg, 9.4 mg/kg, 9.5 mg/kg, 9.6 mg/kg, 9.7 mg/kg, 9.8 mg/kg, 9.9 mg/kg, 10 mg/kg, 11 mg/kg, 12 mg/kg, 13 mg/kg, 14 mg/kg, 15 mg/kg, 16 mg/kg, 17 mg/kg, 18 mg/kg, 19 mg/kg, 20 mg/kg, 21 mg/kg, 22 mg/kg, 23 mg/kg, 24 mg/kg, 25 mg/kg, 26 mg/kg, 27 mg/kg, 28 mg/kg, 29 mg/kg, 30 mg/kg, 31 mg/kg, 32 mg/kg, 33 mg/kg, 34 mg/kg, 35 mg/kg, 36 mg/kg, 37 mg/kg, 38 mg/kg, 39 mg/kg, 40 mg/kg, 41 mg/kg, 42 mg/kg, 43 mg/kg, 44 mg/kg, 45 mg/kg, 46 mg/kg, 47 mg/kg, 48 mg/kg, 49 mg/kg, through 50 mg/kg body per single dose.

Various factors may be considered in the determination of dosage and timing of delivery of an MCJ dsRNA agent of the invention. The absolute amount of an MCJ dsRNA agent or MCJ antisense polynucleotide agent delivered will depend upon a variety of factors including a concurrent treatment, the number of doses and the individual subject parameters including age, physical condition, size and weight. These are factors well known to those of ordinary skill in the art and can be addressed with no more than routine experimentation. In some embodiments, a maximum dose can be used, that is, the highest safe dose according to sound medical judgment.

Methods of the invention may in some embodiments include administering to a subject 1, 2, 3, 4, 5, 6, 7, 8, 9, 10, or more doses of an MCJ dsRNA agent or MCJ antisense polynucleotide agent. In some instances, a pharmaceutical compound, (e.g., comprising an MCJ dsRNA agent or comprising an MCJ antisense polynucleotide agent) can be administered to a subject at least daily, every other day, weekly, every other week, monthly, etc. Doses may be administered once per day or more than once per day, for example, 2, 3, 4, 5, or more times in one 24 hour period. A pharmaceutical composition of the invention may be administered once daily, or the MCJ dsRNA agent or MCJ antisense polynucleotide agent may be administered as two, three, or more sub-doses at appropriate intervals throughout the day or even using continuous infusion or delivery through a controlled release formulation. In some embodiments of methods of the invention, a pharmaceutical composition of the invention is administered to a subject one or more times per day, one or more times per week, one or more times per month, or one or more times per year.

Methods of the invention, in some aspects, include administration of a pharmaceutical compound alone, in combination with one or more other MCJ dsRNA agents or MCJ antisense polynucleotide agents, and/or in combination with other drug therapies or treatment activities or regimens that are administered to subjects with an MCJ-associated disease or condition. Pharmaceutical compounds may be administered in pharmaceutical compositions. Pharmaceutical compositions used in methods of the invention may be sterile and contain an amount of an MCJ dsRNA agent or MCJ antisense polynucleotide agent that will reduce activity of an MCJ polypeptide to a level sufficient to produce the desired response in a unit of weight or volume suitable for administration to a subject. A dose administered to a subject of a pharmaceutical composition that includes an MCJ dsRNA agent or MCJ antisense polynucleotide agent to reduce MCJ protein activity can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

Treatment

MCJ-associated diseases and conditions in which a decrease in a level and/or activity of MCJ polypeptide is effective to treat the disease or condition, can be treated using methods and MCJ dsRNA agents of the invention to inhibit MCJ expression. Examples of diseases and conditions that may be treated with an MCJ dsRNA agent or MCJ antisense polynucleotide agent of the invention and a treatment method of the invention, include, but are not limited to: a metabolic disease or condition, a lipid accumulation disease or condition, a cancer, a liver disease or condition, a cardiac disease or condition, a kidney disease or condition, an immune system disease or condition, a neurological disease or condition, and a lung disease or condition. Further non-limiting examples of a diseases and conditions that can be treated with MCJ dsRNA agents and MCJ antisense polynucleotide agents and methods of the invention are: hepatitis, non-alcoholic fatty liver disease (NAFLD), overweight, weight gain, obesity, diabetes, insulin-resistance, alcoholic fatty liver disease, dyslipidemia, steatosis (e.g., liver steatosis, heart steatosis, kidney steatosis, muscle steatosis), abeta-lipoproteinemia, glycogen storage disease, Weber-Christian disease, lipodystrophy; a liver disease, liver inflammation, hepatitis, cholestasis, liver failure, non-alcoholic steatohepatitis (NASH), steatohepatitis, fibrosis, cirrhosis, Hepatitis C, Genotype 3 Hepatitis C, Alpha 1-antitrypsin deficiency, acute fatty liver of pregnancy, Wilson disease; a kidney disease; chronic kidney disease, polycystic kidney disease, a cardiac disease, hypertension, ischemia, heart failure, cardiomyopathy; overdose, a drug-induced condition, hepatocellular carcinoma, decompensated liver, a post-cancer liver condition, a post-transplant liver condition, poisoning; HIV; a neurodegenerative disease, liver transplantation, kidney transplantation, heart transplantation, Parkinson's disease, Alzheimer's disease; cancer, or physical exercise. Further non-limiting examples of kidney diseases and conditions that can be treated with MCJ dsRNA agents and MCJ antisense polynucleotide agents and methods of the invention are: acute kidney disease (AKD), diabetic kidney disease, kidney failure, pyelonephritis, IgA nephropathy, and child nephrotic syndrome. Such diseases and conditions may be referred to herein as "MCJ-associated diseases and conditions" and "diseases and conditions caused and/or modulated by MCJ."

In certain aspects of the invention, a subject may be administered an MCJ dsRNA agent or MCJ antisense polynucleotide agent of the invention at a time that is one or more of before or after diagnosis of an MCJ-associated disease or condition. In some aspects of the invention, a subject is at risk of having or developing an MCJ-associated disease or condition. A subject at risk of developing an MCJ-associated disease or condition is one who has an increased probability of developing the MCJ-associated disease or condition, compared to a control risk of developing the MCJ-associated disease or condition. In some embodiments of the invention, a level of risk may be statistically significant compared to a control level of risk. A subject at risk may include, for instance, a subject who is, or will be, a subject who has a preexisting disease and/or a genetic abnormality that makes the subject more susceptible to an MCJ-associated disease or condition than a control subject without the preexisting disease or genetic abnormality; a subject having a family and/or personal medical history of the MCJ-associated disease or condition; and a subject who has previously been treated for an MCJ-associated disease or condition. It will be understood that a preexisting disease and/or a genetic abnormality that makes the subject more susceptible to an MCJ-associated disease or condition, may be a disease or genetic abnormality that when present has been previously identified as having a correlative relation to a higher likelihood of developing an MCJ-associated disease or condition.

As used herein, the terms "treat", "treated", or "treating" when used with respect to an MCJ-associated disease or condition may refer to a prophylactic treatment that decreases the likelihood of a subject developing the MCJ-associated disease or condition, and also may refer to a treatment after the subject has developed an MCJ-associated disease or condition in order to eliminate or reduce the level of the MCJ-associated disease or condition, prevent the MCJ-associated disease or condition from becoming more advanced (e.g., more severe), and/or slow the progression of the MCJ-associated disease or condition in a subject compared to the subject in the absence of the therapy to reduce activity in the subject of MCJ polypeptide.

Certain embodiments of agents, compositions, and methods of the invention can be used to inhibit MCJ gene expression. As used herein in reference to expression of an MCJ gene, the terms "inhibit," "silence," "reduce," "down-regulate," and "knockdown" mean the expression of the MCJ gene, as measured by one or more of: a level of RNA transcribed from the gene, a level of activity of MCJ expressed, and a level of MCJ polypeptide, protein or protein subunit translated from the mRNA in a cell, group of cells, tissue, organ, or subject in which the MCJ gene is transcribed, is reduced when the cell, group of cells, tissue, organ, or subject is contacted with (e.g., treated with) an MCJ dsRNA agent or MCJ antisense polynucleotide agent of the invention, compared to a control level of RNA transcribed from the MCJ gene, a level of activity of expressed MCJ, or a level of MCJ translated from the MRNA, respectively. In some embodiments, a control level is a level in a cell, tissue, organ or subject that has not been contacted with (e.g. treated with) the MCJ dsRNA agent or MCJ antisense polynucleotide agent.

Administration Methods

A variety of administration routes for an MCJ dsRNA agent or MCJ antisense polynucleotide agent are available for use in methods of the invention. The particular delivery mode selected will depend at least in part, upon the particular condition being treated and the dosage required for therapeutic efficacy. Methods of this invention, generally speaking, may be practiced using any mode of administration that is medically acceptable, meaning any mode that produces effective levels of treatment of an MCJ-associated disease or condition without causing clinically unacceptable adverse effects. In some embodiments of the invention, an MCJ dsRNA agent or MCJ antisense polynucleotide agent may be administered via an oral, enteral, mucosal, subcutaneous, and/or parenteral route. The term "parenteral" includes subcutaneous, intravenous, intrathecal, intramuscular, intraperitoneal, and intrasternal injection, or infusion techniques. Other routes include but are not limited to nasal (e.g., via a gastro-nasal tube), dermal, vaginal, rectal, and sublingual. Delivery routes of the invention may include intrathecal, intraventricular, or intracranial. In some embodiments of the invention, an MCJ dsRNA agent or MCJ antisense polynucleotide agent may be placed within a slow release matrix and administered by placement of the matrix in the subject. In some aspects of the invention, an MCJ dsRNA agent or MCJ antisense polynucleotide agent may be delivered to a subject cell using nanoparticles coated with a delivery agent that targets a specific cell or organelle. Various delivery means, methods, agents are known in the art. Non-limiting examples of delivery methods and delivery agents are additionally provided elsewhere herein. In some aspects of the invention, the term "delivering" in reference to an MCJ dsRNA agent or MCJ antisense polynucleotide agent may mean administration to a cell or subject of one or more "naked" MCJ dsRNA agent or MCJ antisense polynucleotide agent sequences and in certain aspects of the invention "delivering" means administration to a cell or subject via transfection means, delivering a cell comprising an MCJ dsRNA agent or MCJ antisense polynucleotide agent to a subject, delivering a vector encoding an MCJ dsRNA agent or MCJ antisense polynucleotide agent into a cell and/or subject, etc. Delivery of an MCJ dsRNA agent or MCJ antisense polynucleotide agent using a transfection means may include administration of a vector to a cell and/or subject.

In some methods of the invention one or more MCJ dsRNA agents or MCJ antisense polynucleotide agents may be administered in formulations, which may be administered in pharmaceutically acceptable solutions, which may routinely contain pharmaceutically acceptable concentrations of salt, buffering agents, preservatives, compatible carriers, adjuvants, and optionally other therapeutic ingredients. In some embodiments of the invention an MCJ dsRNA agent or MCJ antisense polynucleotide agent may be formulated with another therapeutic agent for simultaneous administration. According to methods of the invention, an MCJ dsRNA agent or MCJ antisense polynucleotide agent may be administered in a pharmaceutical composition. In general, a pharmaceutical composition comprises an MCJ dsRNA agent or MCJ antisense polynucleotide agent and optionally, a pharmaceutically-acceptable carrier. Pharmaceutically-acceptable carriers are well-known to those of ordinary skill in the art. As used herein, a pharmaceutically-acceptable carrier means a non-toxic material that does not interfere with the effectiveness of the biological activity of the active ingredients, e.g., the ability of the MCJ dsRNA agent or MCJ antisense polynucleotide agent to inhibit MCJ gene expression in a cell or subject. Numerous methods to administer and deliver dsRNA agents or MCJ antisense polynucleotide agents for therapeutic use are known in the art and may be utilized in methods of the invention.

Pharmaceutically acceptable carriers include diluents, fillers, salts, buffers, stabilizers, solubilizers and other materials that are well-known in the art. Exemplary pharmaceutically acceptable carriers are described in U.S. Pat. No. 5,211,657 and others are known by those skilled in the art. Such preparations may routinely contain salt, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

Some embodiments of methods of the invention include administering one or more MCJ dsRNA agents or MCJ antisense polynucleotide agents directly to a tissue. In some embodiments, the tissue to which the compound is administered is a tissue in which the MCJ-associated disease or condition is present or is likely to arise, non-limiting examples of which are the liver or kidney. Direct tissue administration may be achieved by direct injection or other means. Many orally delivered compounds naturally travel to and through the liver and kidneys and some embodiments of treatment methods of the invention include oral administration of one or more MCJ dsRNA agents to a subject. MCJ dsRNA agents or MCJ antisense polynucleotide agents, either alone or in conjunction with other therapeutic agents, may be administered once, or alternatively they may be administered in a plurality of administrations. If administered multiple times, the MCJ dsRNA agent or MCJ antisense polynucleotide agent may be administered via different routes. For example, though not intended to be limiting, a first (or first several) administrations may be made via subcutaneous means and one or more additional administrations may be oral and/or systemic administrations.

For embodiments of the invention in which it is desirable to administer an MCJ dsRNA agent or MCJ antisense polynucleotide agent systemically, the MCJ dsRNA agent or MCJ antisense polynucleotide agent may be formulated for parenteral administration by injection, e.g., by bolus injection or continuous infusion. Formulations for injection may be presented in unit dosage form, e.g., in ampoules or in multi-dose containers, with or without an added preservative. MCJ dsRNA agent formulations (also referred to as pharmaceutical compositions) may take such forms as suspensions, solutions or emulsions in oily or aqueous vehicles, and may contain formulatory agents such as suspending, stabilizing and/or dispersing agents.

Preparations for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringer's, or fixed oils. Intravenous vehicles include fluid and nutrient replenishers, electrolyte replenishers (such as those based on Ringer's dextrose), and the like. Preservatives and other additives may also be present such as, for example, antimicrobials, anti-oxidants, chelating agents, and inert gases and the like. Lower doses will result from other forms of administration, such as intravenous administration. In the event that a response in a subject is insufficient at the initial doses applied, higher doses (or effectively higher doses by a different, more localized delivery route) may be employed to the extent that patient tolerance permits. Multiple doses per day may be used as needed to achieve appropriate systemic or local levels of one or more MCJ dsRNA agents or MCJ antisense polynucleotide agents and to achieve appropriate reduction in MCJ protein activity.

In yet other embodiments, methods of the invention include use of a delivery vehicle such as biocompatible microparticle, nanoparticle, or implant suitable for implantation into a recipient, e.g., a subject. Exemplary bioerodible implants that may be useful in accordance with this method are described in PCT Publication No. WO 95/24929 (incorporated by reference herein), which describes a biocompatible, biodegradable polymeric matrix for containing a biological macromolecule.

Both non-biodegradable and biodegradable polymeric matrices can be used in methods of the invention to deliver one or more MCJ dsRNA agents or MCJ antisense polynucleotide agents to a subject. In some embodiments, a matrix may be biodegradable. Matrix polymers may be natural or synthetic polymers. A polymer can be selected based on the period of time over which release is desired, generally in the order of a few hours to a year or longer. Typically, release over a period ranging from between a few hours and three to twelve months can be used. The polymer optionally is in the form of a hydrogel that can absorb up to about 90% of its weight in water and further, optionally is cross-linked with multivalent ions or other polymers.

In general, MCJ dsRNA agents or MCJ antisense polynucleotide agents may be delivered in some embodiments of the invention using the bioerodible implant by way of diffusion, or by degradation of the polymeric matrix. Exemplary synthetic polymers for such use are well known in the art. Biodegradable polymers and non-biodegradable polymers can be used for delivery of MCJ dsRNA agents or MCJ antisense polynucleotide agents using art-known methods. Bioadhesive polymers such as bioerodible hydrogels (see H. S. Sawhney, C. P. Pathak and J. A. Hubell in Macromolecules, 1993, 26, 581-587, the teachings of which are incorporated by reference herein) may also be used to deliver MCJ dsRNA agents or MCJ antisense polynucleotide agents for treatment of an MCJ-associated disease or condition. Additional suitable delivery systems can include time-release, delayed release or sustained release delivery systems. Such systems can avoid repeated administrations of an MCJ dsRNA agent or MCJ antisense polynucleotide agent, increasing convenience to the subject and the medical care professional. Many types of release delivery systems are available and known to those of ordinary skill in the art. (See for example: U.S. Pat. Nos. 5,075,109; 4,452,775; 4,675,189; 5,736,152; 3,854,480; 5,133,974; and 5,407,686 (the teaching of each of which is incorporated herein by reference). In addition, pump-based hardware delivery systems can be used, some of which are adapted for implantation.

Use of a long-term sustained release implant may be suitable for prophylactic treatment of subjects and for subjects at risk of developing a recurrent MCJ-associated disease or condition. Long-term release, as used herein, means that the implant is constructed and arranged to deliver a therapeutic level of an MCJ dsRNA agent or MCJ antisense polynucleotide agent for at least up to 10 days, 20 days, 30 days, 60 days, 90 days, six months, a year, or longer. Long-term sustained release implants are well-known to those of ordinary skill in the art and include some of the release systems described above.

Therapeutic formulations of MCJ dsRNA agents or MCJ antisense polynucleotide agents may be prepared for storage by mixing the molecule or compound having the desired degree of purity with optional pharmaceutically acceptable carriers, excipients or stabilizers [Remington's Pharmaceutical Sciences 21st edition, (2006)], in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN®, PLURONICS® or polyethylene glycol (PEG).

Cells, Subjects, and Controls

Methods of the invention may be used in conjunction with cells, tissues, organs and/or subjects. In some aspects of the invention a subject is a human or vertebrate mammal including but not limited to a dog, cat, horse, cow, goat, mouse, rat, and primate, e.g., monkey. Thus, the invention can be used to treat MCJ-associated diseases or conditions in human and non-human subjects. In some aspects of the invention a subject may be a farm animal, a zoo animal, a domesticated animal or non-domesticated animal and methods of the invention can be used in veterinary prevention and treatment regimens. In some embodiments of the invention, the subject is a human and methods of the invention can be used in human prevention and treatment regimens.

Non-limiting examples of subjects to which the present invention can be applied are subjects who are diagnosed with, suspected of having, or at risk of having, a liver disease or condition associated with MCJ expression. Methods of the invention may be applied to a subject who, at the time of treatment, has been diagnosed as having a liver disease or condition, or a subject who is considered to be at risk for having or developing a liver disease or condition. In some aspects of the invention a liver disease or condition is an acute liver disease or condition, and in certain aspects of the invention a liver disease or condition is a chronic liver disease or condition.

Another non-limiting example of subjects to whom certain embodiments of methods and compositions of the present invention can be applied are subjects who are diagnosed with, suspected of having, or at risk of having, a kidney disease or condition associated with MCJ expression. Methods of the invention may be applied to a subject who, at the time of treatment, has been diagnosed as having such a kidney disease or condition, or a subject who is considered to be at risk for having or developing such a kidney disease or condition. In some aspects of the invention a kidney disease or condition is an acute kidney disease or condition, and in certain aspects of the invention a kidney disease or condition is a chronic kidney disease or condition.

A cell to which methods of the invention may be applied include cells that are in vitro, in vivo, ex vivo cells. Cells may be in a subject, in culture, and/or in suspension, or in any other suitable state or condition. A cell to which a method of the invention may be applied can be a liver cell, a kidney cell, a cardiac cell, a lung cell, or other type of vertebrate cell, including human and non-human mammalian cells. In certain aspects of the invention, a cell to which methods of the invention may be applied is a healthy, normal cell that is not known to be a disease cell. In certain embodiments of the invention a cell to which methods and compositions of the invention may be applied is a liver cell, a kidney cell, a cancerous liver cell, a metastatic cancer cell, a precancerous liver cell, a cirrhotic liver cell, a post-cancer liver cell, a fibrotic liver cell, a hepatocyte, an inflammatory liver cancer cell, and a chemo-resistant cancerous cell, a cancerous cell, a cardiac cell, an immune system cell, a neuron, and a lung cell, etc. In certain aspects of the invention, a control cell is a normal cell, but it will be understood that a cell having a disease or condition (for example but not limited to a liver disease or condition or a kidney disease or condition) may also serve as a control cell in particular circumstances for example to compare results in a treated cell having a disease or condition versus an untreated cell having the disease or condition, etc.

A level of MCJ polypeptide activity can be determined and compared to control level of MCJ polypeptide activity, according to methods of the invention. A control may be a predetermined value, which can take a variety of forms. It can be a single cut-off value, such as a median or mean. It can be established based upon comparative groups, such as in groups having normal levels of MCJ polypeptide and/or MCJ polypeptide activity and groups having increased levels of MCJ polypeptide and/or MCJ polypeptide activity. Another non-limiting example of comparative groups may be groups having one or more symptoms of or a diagnosis of a liver disease or condition or a kidney disease or condition and groups without having one or more symptoms of or a diagnosis of the liver disease or condition or the kidney disease or condition, respectively. Typically, a control may be based on apparently healthy normal individuals in an appropriate age bracket or apparently healthy cells. It will be understood that controls according to the invention may be, in addition to predetermined values, samples of materials tested in parallel with the experimental materials. Examples include samples from control populations or control samples generated through manufacture to be tested in parallel with the experimental samples. In some embodiments of the invention, a control may include a cell or subject not contacted or treated with an MCJ dsRNA agent of the invention and in such instances, a control level of MCJ polypeptide and/or MCJ polypeptide activity can be controlled to a level of MCJ polypeptide and/or MCJ polypeptide activity in a cell or subject contacted with an MCJ dsRNA agent or MCJ antisense polynucleotide agent of the invention.

In some aspects of the invention, values of one or more of MCJ polypeptide activity determined for a subject may serve as control values for later determinations of MCJ polypeptide activity, in that same subject, thus permitting assessment of changes from a "baseline" MCJ polypeptide activity in a subject. Thus, an initial MCJ polypeptide level and/or initial MCJ polypeptide activity level may be present and/or determined in a subject, cell, or tissue and methods and compounds of the invention may be used to decrease the level of MCJ polypeptide and/or MCJ polypeptide activity in the subject, with the initial level serving as a control level for that subject. Using methods and MCJ dsRNA agents or MCJ antisense polynucleotide agents of the invention, a level of MCJ polypeptide in a cell and/or subject may be decreased by at least 0.5%, 1%, 5%, 10%, 20%, 30%, 40%, 50%, 60%, 70%, 80%, 90%, 95%, or more compared to the initial level as a treatment for a disease or condition associated with MCJ polypeptide activity in the cell and/or subject, respectively, or compared to a non-contacted control level in a cell and/or subject, respectively. It will be understood that a level of MCJ polypeptide and a level of MCJ polypeptide activity both correlate with a level of MCJ gene expression. Thus, administering methods and compositions of the invention to a cell, tissue, and/or subject in an amount effective to inhibit MCJ gene expression will result in a lower level of MCJ polypeptide and a lower level of MCJ polypeptide activity in the cell, tissue, and/or subject, respectively. Using methods and compositions of the invention, a level of MCJ activity in a cell may be decreased by at least 0.5%, 1%, 5%, 10%, 20%, 30%, 40%, 50%, 60%, 70%, 80%, 90%, 95%, or more compared to the initial level in the cell, prior to such contact or as compared to a non-contacted control cell level.

Kits

Also within the scope of the invention are kits that comprise one or more MCJ dsRNA agents and/or MCJ antisense polynucleotide agents and instructions for its use in methods of the invention. Kits of the invention may include one or more of an MCJ dsRNA agent or MCJ antisense polynucleotide agent that may be used to treat an MCJ-associated disease or condition. Kits containing one or more MCJ dsRNA agents or MCJ antisense polynucleotide agents can be prepared for use in treatment methods of the invention. Components of kits of the invention may be packaged either in aqueous medium or in lyophilized form. A kit of the invention may comprise a carrier being compartmentalized to receive in close confinement therein one or more container means or series of container means such as test tubes, vials, flasks, bottles, syringes, or the like. A first container means or series of container means may contain one or more compounds such as an MCJ dsRNA agent and/or MCJ antisense polynucleotide agent. A second container means or series of container means may contain a targeting agent, a labelling agent, a delivery agent, etc. that may be included as a portion of an MCJ dsRNA agent or MCJ antisense polynucleotide agent to be administered in an embodiment of a treatment method of the invention.

A kit of the invention may also include instructions. Instructions typically will be in written form and will provide guidance for carrying-out a treatment embodied by the kit and for making a determination based upon that treatment.

The following examples are provided to illustrate specific instances of the practice of the present invention and are not intended to limit the scope of the invention. As will be apparent to one of ordinary skill in the art, the present invention will find application in a variety of compositions and methods.

EXAMPLES

Example 1

MCJ dsRNA Screening and Assessment

Effects of human MCJ siRNA assessed in a human cell line. The term "siRNA" corresponds to the term "dsRNA agent" as described elsewhere herein. To screen the selected human siRNA for human MCJ sequences, 56 siRNAs expanding the human MCJ coding region were synthesized. The first screening was performing in the breast cancer MCF7 cells, human cell line. This cell line was selected because these cells express high levels of MCJ and are easy to transfect. MCF7 cells were transfected using RNAiMAX and 1 or 10 nM of the different siMCJs, per manufacturer's instructions.

Briefly, the siRNA was diluted in OPTI-MEM, and mixed with siRNA diluted in OPTIMEM. The mixture was incubated for 20 min at room temperature (RT). Then the mixture was transferred to culture plates containing MCF7 cells. 48 h later, cells were harvested and RNA was isolated using Qiagen Micro RNeasy kit, per manufacturer's instructions. cDNA was made from the RNA and used for detection of human MCJ mRNA by real time RT-PCR.

MCJ siRNAs: MITO-4, MITO-5, MITO-6, MITO-7, MITO-8, MITO-12, MITO-13, MITO-14, MITO-15, MITO-16, MITO-20, MITO-21, MITO-22, MITO-23, MITO-24, MITO-28, MITO-29, MITO-30, MITO-31, MITO-32, MITO-36, MITO-37, MITO-38, MITO-39, MITO-40, MITO-44, MITO-45, MITO-46, MITO-47, MITO-48, MITO-52, MITO-53, MITO-54, MITO-55, and MITO-56 were individually tested at a concentration of 1 nM.

MCJ siRNAs: MITO-1, MITO-2, MITO-3, MITO-9, MITO-10, MITO-11, MITO-17, MITO-18, MITO-19, MITO-25, MITO-26, MITO-27, MITO-33, MITO-34, MITO-35, MITO-41, MITO-42, MITO-43, MITO-49, MITO-50, and MITO-51 were individually tested at a concentration of 10 nM.

Results

Results of certain experiments are shown in Table 3. The first column in Table 3 identifies the name assigned to the MCJ siRNA. The second column identifies the corresponding position in MCJ RNA sequence. Tables 1 and 2 provide the siRNA sequences and position information based on alignment with MCJ RNA. Table 3, third column shows results of experiments in which Human MCF-7 cells were contacted with the indicated siRNA at a concentration of 1 nM. Table 3, fourth column shows results of experiments in which Human MCF-7 cells were contacted with the indicated siRNA at a concentration of 10 nM. Results are shown as "% knock down" (% KD) at the different siRNA concentrations, which indicates the % reduction in MCJ expression resulting from the siRNA contact, versus MCF-7 cells not contacted with an MCJ siRNA (transfecting reagent alone). The results indicate a significant reduction in MCJ gene expression resulting from contact with the siRNAs.

| siRNAs Identification Numbers | Sequence position | Human MCF-7% KD at 1 nM | Human MCF-7% KD at 10 nM | Mouse Hepal-6% KD at 1 nM |
|---|---|---|---|---|
| Mito-1 | 482 | | 70% | |
| Mito-2 | 524 | | 92% | 24.8% |
| Mito-3 | 526 | | 93% | 25.9% |
| Mito-4 | 527 | 91.2% | | 28.5% |
| Mito-5 | 528 | 82.6% | | −12.6% |
| Mito-6 | 537 | 90.0% | | 80.9% |
| Mito-7 | 542 | 73.2% | | |
| Mito-8 | 545 | 74.9% | | |
| Mito-9 | 546 | | 77% | |
| Mito-10 | 551 | | 90% | |
| Mito-11 | 552 | | 88% | |
| Mito-12 | 555 | 88.1% | | |
| Mito-13 | 556 | 80.1% | | |
| Mito-14 | 557 | 64.3% | | |
| Mito-15 | 558 | 82.9% | | |
| Mito-16 | 559 | 85.4% | | −1.7% |
| Mito-17 | 570 | | 92% | 75.0% |
| Mito-18 | 571 | | 89% | 64.5% |
| Mito-19 | 579 | | 90% | 91.9% |
| Mito-20 | 580 | 90.9% | | 91.9% |
| Mito-21 | 588 | 88.8% | | 85.6% |
| Mito-22 | 632 | 84.7% | | 13.7% |
| Mito-23 | 635 | 87.6% | | 67.1% |
| Mito-24 | 636 | 94.1% | | 90.9% |
| Mito-25 | 637 | | 95% | 80.4% |
| Mito-26 | 641 | | −72% | |
| Mito-27 | 642 | | 61% | |
| Mito-28 | 643 | 68.2% | | |
| Mito-29 | 669 | 89.6% | | |
| Mito-30 | 690 | 62.1% | | |
| Mito-31 | 691 | 81.9% | | −16.0% |
| Mito-32 | 692 | 90.6% | | 62.7% |
| Mito-33 | 700 | | 55% | |
| Mito-34 | 702 | | 63% | |
| Mito-35 | 704 | | 98% | 87.8% |
| Mito-36 | 711 | 79.8% | | |
| Mito-37 | 715 | 88.0% | | 34.9% |
| Mito-38 | 716 | 86.3% | | −22.1% |
| Mito-39 | 717 | 90.1% | | 47.9% |
| Mito-40 | 718 | 90.0% | | 67.3% |
| Mito-41 | 720 | | 94% | 55.9% |
| Mito-42 | 721 | | 96% | 66.2% |
| Mito-43 | 722 | | 97% | 50.3% |
| Mito-44 | 723 | 83.0% | | 34.8% |
| Mito-45 | 725 | 90.6% | | 25.8% |
| Mito-46 | 728 | 93.7% | | 88.8% |
| Mito-47 | 773 | 89.1% | | 41.2% |

-continued

| siRNAs Identification Numbers | Sequence position | Human MCF-7% KD at 1 nM | Human MCF-7% KD at 10 nM | Mouse Hepal-6% KD at 1 nM |
|---|---|---|---|---|
| Mito-48 | 774 | 90.2% | | 15.0% |
| Mito-49 | 775 | | 92% | 79.1% |
| Mito-50 | 780 | | 93% | −1.4% |
| Mito-51 | 781 | | 82% | 63.2% |
| Mito-52 | 782 | 94.7% | | 85.6% |
| Mito-53 | 783 | 93.9% | | 76.0% |
| Mito-54 | 784 | 89.5% | | 52.9% |
| Mito-55 | 785 | 84.8% | | 51.0% |
| Mito-56 | 814 | 69.7% | | |

Example 2

Human siRNAs were screened for cross-reactivity on mouse MCJ using a mouse cell line. The term "siRNA" corresponds to the term "dsRNA agent" as described elsewhere herein Experiments were performed to test the efficacy of selected human siMCJs to reduce the expression of mouse MCJ. The selected siMCJs had been determined as described above, to reduce human MCJ expression by at least 80%. To test for cross-reactivity, human siMCJ were transfected into the hepatocellular carcinoma HEPA 1-6 mouse cell line. As described in Example 1 herein, HEPA 1-6 cells were transfected with 1 nM of human siMCJ using RNAiMAX. 48 h later, RNA was isolated and used for cDNA and detection of mouse MCJ mRNA by real time RT-PCR.

MCJ siRNAs: MITO-2, MITO-3, MITO-4, MITO-5, MITO-6, MITO-16, MITO-17, MITO-18, MITO-19, MITO-20, MITO-21, MITO-22, MITO-23, MITO-24, MITO-25, MITO- 31, MITO-32, MITO-35, MITO-37, MITO-38, MITO-39, MITO-40, MITO-41, MITO-42, MICT-43, MITO-44, MITO-45, MITO-46, MITO-47, MITO-48, MITO-49, MITO-50, MITO-51, MITO-52, MITO-53, MITO-54, and MITO-55 were individually tested at a concentration of 1 nM.

Results

Results of certain experiments are shown in Table 3. The first column in Table 3 identifies the name assigned to the MCJ siRNA. The second column identifies the corresponding position in MCJ RNA sequence. Tables 1 and 2 provide the siRNA sequences and position information based on alignment with MCJ RNA. Table 3, fifth column shows results of experiments in which mouse Hepa1-6 cells were contacted with the indicated siRNA at a concentration of 1 nM. Results are shown as "% knock down" (% KD) at the 1 nM siRNA concentration, which indicates the % reduction in MCJ expression resulting from the siRNA contact, as compared to the level of MCJ expression in Hepa1-6 cells not contacted with an MCJ siRNA. The results indicate a significant reduction in MCJ gene expression resulting from contact with the siRNAs.

Example 3

Synthesis of GalNAc Conjugated siMCJ 3.1 Solid Phase Synthesis of Sense Strand and Antisense Strand Both sense and antisense were synthesized using phosphoramidite technology for solid phase oligonucleotide synthesis. AKTA oligo pilot plus 10 (GE Healthcare) or Mermade analogous synthesizer (DNAChem) was used. Synthesis was performed on controlled pore glass solid support (Universal CPG, loading: 36.2 μmol/g, 1000 Å). All 2'-modified nucleoside phosphoramidites were purchased from commercial sources. Specifically, the following 2'-O-methyl and 2'-fluoro nucleoside phosphoramidites were used: DMT-2'-F-Bz-dA phosphoramidite, DMT-2'-F-dU phosphoramidite, DMT-2'-F-ibu-dG phosphoramidite, DMT-2'-F-Ac-dC phosphoramidite, DMT-2'-OMe-Bz-A phosphoramidite, DMT-2'-OMe-U phosphoramidite, DMT-2'-OMe-ibu-G phosphoramidite, DMT-2'-OMe-Ac-C phosphoramidite. Phosphoramidite of GalNAc targeting ligand cluster Mito-F was synthesized according to a published procedure (PCT Application: WO2020191183A1). All the phosphoramidites were dissolved in anhydrous acetonitrile (100 mM) and dried over molecular sieves (3 Å) before using. 5-ethylthio-1H-tetrazole (ETT, 600 mM in acetonitrile) was used as the activator. General conditions of the solid phase synthesis cycle are shown in Table 4.

TABLE 4

Synthesis condition for sense and antisense use 2'-modified amidite.

| Step | Operation | Reagent | Times(min) |
|---|---|---|---|
| 1 | Deblocking | 3% $CCl_3COOH$ in $CH_2Cl_2$ | 1 |
| 2 | Coupling | ETT 0.25M/ BTT 0.30M v/v, 1/1 in acetonitrile + 0.05M amidite in acetonitrile (8 eq.) | 10 |
| 3 | Oxidation/ Thiolation | Oxidation: 0.05M $I_2$ in pyridine/$H_2O$/THF(2/1/7, v/v/v) | 1 |
| | | Thiolation: PADS 0.20M in pyridine/Acetonitrile (1/1, v/v) | 1 |
| 4 | Capping | $Ac_2O$/THF(10/90, v/v) pyridine/imidazole/ THF(10/16/74, v/v/v) | 1 |

3.2 Attaching GalNAc Ligand Cluster to 5' Position of Sense Strand on Solid Support.

Targeting ligand cluster Mito-F was attached to 5' position of sense strand by manual operation in a glove box. To CPG support with sense strand (5 μmol) from synthesizer was added anhydrous Acetonitrile (3 mL). The mixture was dried over molecular sieves (3 Å) for 30 min. Mito-F phosphoramidite (40 μmol, 8 eq.) in anhydrous Acetonitrile (1 mL, dried over molecular sieves (3 Å) for 30 min) was added. Activator (ETT, 0.5 mL, 0.6 M in Acetonitrile, dried over molecular sieves 3 Å) was added to the resulting mixture. The reaction mixture was shaken for 1.5 hours at 20° C. Solvent was removed by syringe. The CPG support resin was treated with (PADS 0.20 M in pyridine/acetonitrile (1/1, v/v) at 20° C. The reaction suspension was hold at 20° C. for 20 min. CPG support was washed with acetonitrile (5 mL×4) by filtration to generate the corresponding sense strand on CPG support.

3.3 Cleavage and Deprotection of Sense and Antisense Strand from CPG Support

CPG support with sense or antisense strand attached was treated with a 1:1 mixture of 40% methylamine in water and 28% ammonium hydroxide solution (2 mL) for 15 min. at 20° C., and then was heated at 65° C. for 15 min. Reaction mixture was filtered, and the resulting solution was evaporated at 40° C. under vacuum with centrifuge to afford white solid.

3.4 Purification of Sense and Antisense Stand

Crude oligonucleotides were purified by HPLC using Durashell column (C18 10×100 mm, 5 μm). Mobile Phase A: 220 μM HFIP and 8.8 μM TEA in Milli Q water, pH 7.5 and mobile; Phase B: methanol. Gradient: mobile phase B from 5% to 29% in 16 min. Flow rate: 3.5 mL/min; Column temperature: 50° C. UV monitor was set at 260 nm.

3.5 Annealing Sense and Antisense Strands to Form Duplex siRNA.

The sense was mixed with the equimolar antisense in Phosphate-Buffered Saline (pH 7.4) to form the duplex. The annealing temperature was set at 20° C. The oligonucleotide concentration was 3 μmol in 400 μl 1×PBS. The annealing progress was monitored by HPLC using Waters BEH C18 2.5 μm*3*100 mm column with column temperature set at 20° C. UV detection was set at 260 nm. Mobile phase A was 100 mM HFIP and 20 mM HA in Milli Q water containing 5% acetonitrile. Mobile phase B was 20% Milli Q water in acetonitrile.

3.6 Purification of Duplex siRNA

The duplex was purified by IP-RP HPLC using Durashell C18(L) 10×100 mm, 5 μm column. Mobile Phase A: 100 mM HFIP and 20 mM HA in Milli Q water containing 5% acetonitrile and Mobile Phase. Mobile B: 20% Milli Q water in acetonitrile. The gradient: mobile phase B from 18% to 35% in 18 min. Flow rate: 4 mL/min. The column temperature was set at 17° C. UV detection was set at 260 nm. The resulting fraction was lyophilized to give desired duplex siMCJ. Table 5 sets forth abbreviations and symbols used in Table 6.

Table 5 shows abbreviations and symbols of nucleotide monomers used in nucleic acid sequence representation in Table 6. The monomers, when present in an oligonucleotide, are mutually linked by 5'-3'-phosphodiester bonds

| Abbreviation | Nucleotides |
|---|---|
| a | 2'-O-methyladenosine-3'-phosphate |
| a• | 2'-O-methyladenosine-3'-phosphorothioate |
| A | 2'-fluoroadenosine-3'-phosphate |

-continued

| Abbreviation | Nucleotides |
|---|---|
| A• | 2'-fluoroadenosine-3'-phosphorothioate |
| c | 2'-O-methylcytidine-3'-phosphate |
| c• | 2'-O-methylcytidine-3'-phosphorothioate |
| C | 2'-fluorocytidine-3'-phosphate |
| C• | 2'-fluorocytidine-3'-phosphorothioate |
| g | 2'-O-methylguanosine-3'-phosphate |
| g• | 2'-O-methylguanosine-3'-phosphorothioate |
| G | 2'-fluoroguanosine-3'-phosphate |
| G• | 2'-fluoroguanosine-3'-phosphorothioate |
| u | 2'-O-methyluridine-3'-phosphate |
| u• | 2'-O-methyluridine-3'-phosphorothioate |
| U | 2'-fluorouridine-3'-phosphate |
| U• | 2'-fluorouridine-3'-phosphorothioate |
| L | Targeting Ligand cluster (a non-limiting example of which is MITO-F) |

Compounds in Table 6 were synthesized according to the general procedure outlined above. Table 6 provides describes certain Mito-F conjugated siMCJs. Abbreviations and symbols used in Table 6 are described in Table 5. In some studies siMCJ molecules were conjugated to a GalNAc targeting ligand cluster. A non-limiting example of one targeting ligand cluster that was used in certain studies is identified herein as MITO-F. The position of the GalNAc targeting ligand cluster is indicated in Table 6 with "L" and the structure of the MITO-F targeting ligand cluster is illustrated below. The siRNA attachment is shown and as indicated X=O, S.). GalNAc targeting ligand cluster Mito-F was synthesized according to a published procedure (PCT Application: WO2020191183A1) and additional GalNAc ligand clusters were also tested in conjunction with siRNAs set forth herein.

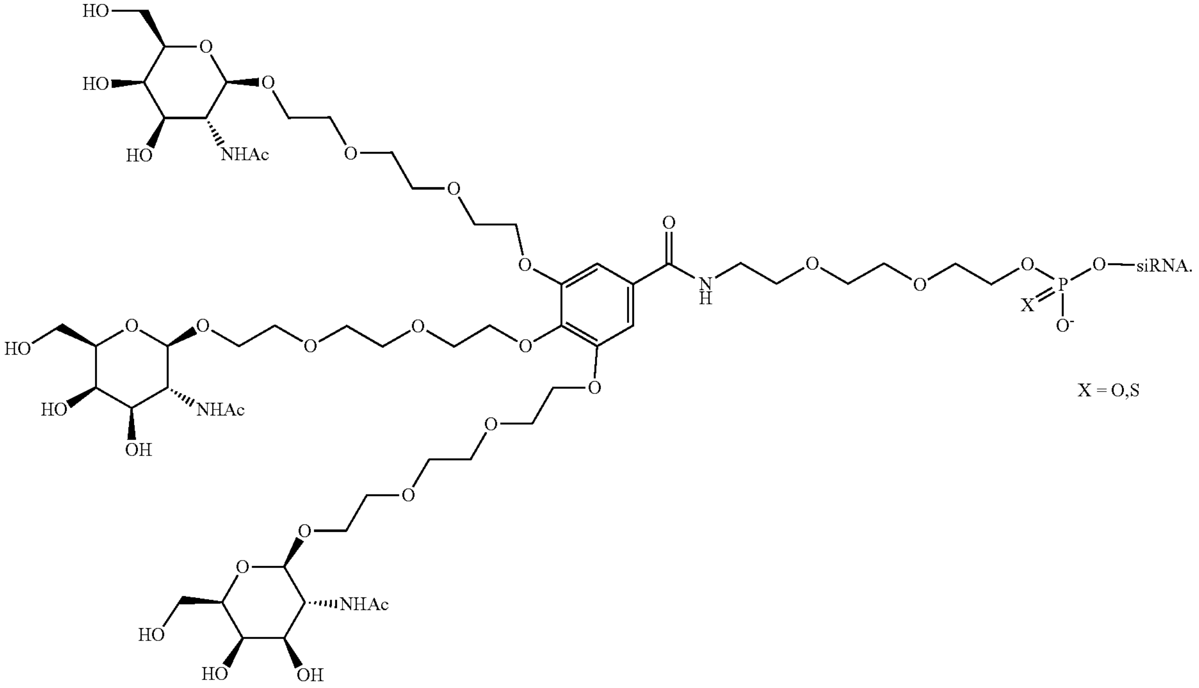

X = O,S

Table 6 shows the assigned identifiers of double-stranded siMCJ RNAs conjugated to a GalNAc ligand cluster are provided in the second column from left. The sense and antisense strands for each of the double-stranded siMCJ RNAs are provided in the right-most column, with each sense and antisense strand assigned a SEQ ID NO. Table 5 is a key to the abbreviations and symbols for sequences in Table 6 are shown in Table 5.

TABLE 6

Summary of Mito-F conjugated siMCJs. "Pos" is Position. "S" is Sense and "AS" is antisense. The L corresponds to an optional linker such as a GalNAc ligand

| SEQ ID NO | Assigned Identifier | Pos | | Sense (S) and Antisense (AS) strand 5' to 3' |
|---|---|---|---|---|
| 171 | MITO-F-siMCJ-1 | 570 | S | L•acgcauuuCGGaucuggaa•a•a |
| 172 | | | AS | u•UuUcCaGaUcCgAaAuGc•G•u |
| 173 | MITO-F-siMCJ-2 | 579 | S | L•ggaucuggAAAccucuaga•a•a |
| 174 | | | AS | u•UuCuAgAgGuUuCcAgAu•C•c |
| 175 | MITO-F-siMCJ-3 | 580 | S | L•gaucuggaAACcucuagaa•c•a |
| 176 | | | AS | u•GuUcUaGaGgUuUcCaGa•U•c |
| 177 | MITO-F-siMCJ-4 | 588 | S | L•aaccucuaGAAcaaguuau•c•a |
| 178 | | | AS | u•GaUaAcUuGuUcUaGaGg•U•u |
| 179 | MITO-F-siMCJ-5 | 692 | S | L•gcuggucuUAUuuuaggug•u•a |
| 180 | | | AS | u•AcAcCuAaAaUaAgAcCa•G•c |
| 181 | MITO-F-siMCJ-6 | 704 | S | L•uuagguguAAGcccaucug•c•a |
| 182 | | | AS | u•GeAgAuGgGcUuAcAcCu•A•a |
| 183 | MITO-F-siMCJ-7 | 775 | S | L•cccagauaAAGguggaucu•c•a |
| 184 | | | AS | u•GaGaUcCaCcUuUaUcUg•G•g |
| 185 | MITO-F-siMCJ-8 | 780 | S | L•auaaagguGGAucuccuua•c•a |
| 186 | | | AS | u•GuAaGgAgAuCcAcCuUu•A•u |
| 187 | MITO-F-siMCJ-9 | 782 | S | L•aaagguggAUCuccuuacg•u•a |
| 188 | | | AS | u•AcGuAaGgAgAuCcAcCu•U•u |
| 189 | MITO-F-siMCJ-10 | 783 | S | L•aagguggaUCUccuuacgu•a•a |
| 190 | | | AS | u•UaCgUaAgGaGaUcCaCc•U•u |
| 191 | MITO-F-siMCJ-11 | 579 | S | L•gaucuggAAAccucuaga•a•a |
| 192 | | | AS | u•UuCuAgAgGuUuCcAgAuC•u•u |
| 193 | MITO-F-siMCJ-12 | | S | L•gaucuggAAAccucuagaaa•u•u |
| 194 | | | AS | u•UuCuAgAgGuUuCcAgAuC•u•u |
| 195 | MITO-F-siMCJ-13 | | S | L•ggaucuggAAAccucuaga•a•a |
| 196 | | | AS | u•Uucuagagguuu Ccagau•c•c |
| 197 | MITO-F-siMCJ-14 | | S | L•ggaucuggAAAccucuaga•a•a |
| 198 | | | AS | u•UucuAgagguuuCcAgau•c•c |
| 199 | MITO-F-siMCJ-15 | | S | L•ggaucuggAAAccucuaga•a•a |
| 200 | | | AS | u•UucuAgAgguUuCcAgau•c•c |
| 201 | MITO-F-siMCJ-16 | | S | L•ggaucuggAAAccucuaga•a•a |
| 202 | | | AS | u•UucuAgAgguUuCcAgau•c•c |
| 203 | MITO-F-siMCJ-17 | 580 | S | L•ucuggaAACcucuagaa•c•a |
| 304 | | | AS | u•GuUcUaGaGgUuUcCaGa•U•c |
| 205 | MITO-F-siMCJ-18 | | S | L•gaucuggaAACcucuagaa•c•a |
| 206 | | | AS | u•GuUcUaGaGgUuUcCaGaUc•u•u |
| 207 | MITO-F-siMCJ-19 | | S | L•gaucuggaAACcucuagaa•c•a |
| 208 | | | AS | u•GuucuagagguuUccaga•a•c |
| 209 | MITO-F-siMCJ-20 | | S | L•gaucuggaAACcucuagaa•c•a |
| 210 | | | AS | u•GuucuaGaggUuUccaga•a•c |
| 211 | MITO-F-siMCJ-21 | | S | L•gaucuggaAACcucuagaa•c•a |
| 212 | | | AS | u•GuucUaGaggUuUcCaga•a•c |
| 213 | MITO-F-siMCJ-22 | | S | L•gaucuggaAACcucuagaa•c•a |
| 214 | | | AS | u•G•uucUaGaggUuUcCaga•a•c |
| 215 | MITO-F-siMCJ-23 | | S | L•gaucuggaAACcucuagaa•c•a |
| 216 | | | AS | u•GuucUaGaggUuUcCagauc•u•u |
| 217 | MITO-F-siMCJ-24 | | S | L•gaucuggaAACcucuagaa•c•a |
| 218 | | | AS | u•GuucUaGaggUuUcCagauc•c•g |
| 219 | MITO-F-siMCJ-25 | | S | L•gaucuggaAACcucuagaa•c•a |
| 220 | | | AS | u•GuucU aGaggUuU cCaga•u•c |
| 221 | MITO-F-siMCJ-26 | | S | L•gaucugGaAACcucuagaa•c•a |
| 222 | | | AS | u•GuucUaGaggUuUcCaga•u•c |
| 223 | MITO-F-siMCJ-27 | | S | L•gaucuggaAACcucuagaa•c•a |
| 224 | | | AS | u•GuucUaGaggUuUcCaga•u•c |

TABLE 6-continued

Summary of Mito-F conjugated siMCJs. "Pos" is Position. "S" is Sense and "AS" is antisense. The L corresponds to an optional linker such as a GalNAc ligand

| SEQ ID NO | Assigned Identifier | Pos | | Sense (S) and Antisense (AS) strand 5' to 3' |
|---|---|---|---|---|
| 225 | MITO-F-siMCJ-28 | | S | L•gcucuggaAACcucuagaa•c•a |
| 226 | | | AS | u•GuucUaGaggUuUcCaga•g•c |
| 227 | MITO-F-siMCJ-29 | | S | L•cucuggaAACcucuagaa•c•a |
| 228 | | | AS | u•GuucUaGaggUuUcCag•a•g |
| 229 | MITO-F-siMCJ-30 | | S | L•gaucugGaAACcucuagaa•c•a |
| 230 | | | AS | u•G•uucUaGAgguuUcCagauc•c•g |
| 231 | MITO-F-siMCJ-31 | | S | L•gaucugGaAACcucuagaa•c•a |
| 231 | | | AS | u•G•uucU•aGAgguuUcCaga•u•c |
| 233 | MITO-F-siMCJ-32 | | S | L•gcucugGaAACcucuagaa•c•a |
| 234 | | | AS | u•G•uucU•aGAgguuUcCaga•g•c |
| 235 | MITO-F-siMCJ-33 | 581 | S | L•cucuggaaACCucuagaac•a•a |
| 236 | | | AS | u•UguuCuAgagGuUuCcag•a•g |
| 237 | MITO-F-siMCJ-34 | 583 | S | L•cuggaaacCUCuagaacaa•g•a |
| 238 | | | AS | u•CuugUuCuagAgGuUucc•a•g |
| 239 | MITO-F-siMCJ-35 | 584 | S | L•uggaaaccUCUagaacaag•u•a |
| 240 | | | AS | u•AcuuGuUcuaGaGgUuuc•c•a |
| 241 | MITO-F-siMCJ-36 | 585 | S | L•ggaaaccuCUAgaacaagu•u•a |
| 242 | | | AS | u•AacuUgUucuAgAgGuuu•c•c |
| 243 | MITO-F-siMCJ-37 | 586 | S | L•gaaaccucUAGaacaaguu•a•a |
| 244 | | | AS | u•UaacUuGuucUaGaGguu•u•c |
| 245 | MITO-F-siMCJ-38 | 587 | S | L•caaccucuAGAacaaguua•u•a |
| 246 | | | AS | u•AuaaCuUguuCuAgAggu•u•g |
| 247 | MITO-F-siMCJ-39 | 588 | S | L•ccucuaGAAcaaguuau•c•a |
| 248 | | | AS | u•GaUaAcUuGuUcUaGaGg•U•u |
| 249 | MITO-F-siMCJ-40 | | S | L•caccucuaGAAcaaguuau•c•a |
| 250 | | | AS | u GaUaAcUuGuUcUaGaGg•U•g |
| 251 | MITO-F-siMCJ-41 | | S | L•aaccucuaGAAcaaguuau•c•a |
| 252 | | | AS | u•GaUaAcUuGuUcUaGaGgUu•u•c |
| 253 | MITO-F-siMCJ-42 | | S | L•caccucuaGAAcaaguuau•c•a |
| 254 | | | AS | u•GauaAcUuguUcUaGagg•u•g |
| 255 | MITO-F-siMCJ-43 | | S | L•caccucuaGAAcaaguuau•c•a |
| 256 | | | AS | u•GauaAcUuguUcUaGagg•u•g |
| 257 | MITO-F-siMCJ-44 | | S | L•gaccucuaGAAcaaguuau•c•a |
| 258 | | | AS | u•GauaAcUuguUcUaGagg•u•c |
| 259 | MITO-F-siMCJ-45 | | S | L•caccucuaGAAcaaguuau•c•a |
| 260 | | | AS | u•GauaAcUuguUcUaGagg•u•g |
| 261 | MITO-F-siMCJ-46 | | S | L•caccucuaGAAcaaguuau•c•a |
| 262 | | | AS | u•GauaAcUUguucUaGagg•u•g |
| 263 | MITO-F-siMCJ-47 | | S | L•ccucuaGAAcaaguuau•c•a |
| 264 | | | AS | u•GauaAcUUguucUaGa•g•g |
| 265 | MITO-F-siMCJ-48 | | S | L•caccucuaGAAcaaguuau•c•a |
| 266 | | | AS | u•GauaAcUUguucUaGagg•u•g |
| 267 | MITO-F-siMCJ-49 | | S | L•caccucUaGAAcaaguaau•c•a |
| 268 | | | AS | u•GauuAcUUguucUaGagg•u•g |
| 269 | MITO-F-siMCJ-50 | 589 | S | L•gccucuagAACaaguuauc•a•a |
| 270 | | | AS | u•UgauAaCuugUuCuAgag•g•c |
| 271 | MITO-F-siMCJ-51 | 590 | S | L•ccucuagaACAaguuauca•c•a |
| 272 | | | AS | u•GugaUaAcuuGuUcUaga•g•g |
| 273 | MITO-F-siMCJ-52 | 775 | S | L•ccagauaAAGguggaucu•c•a |
| 274 | | | AS | u•GaGaUcCaCcUuUaUcU•g•g |
| 275 | MITO-F-siMCJ-53 | 780 | S | L•caaagguGGAucuccuua•c•a |
| 276 | | | AS | u•GuAaGgAgAuCcAcCuU•u•g |
| 277 | MITO-F-siMCJ-54 | 782 | S | L•agguggAUCuccuuacg•u•a |
| 278 | | | AS | u•AcGuAaGgAgAuCcAcCu•U•u |
| 279 | MITO-F-siMCJ-55 | | S | L•cagguggAUCuccuuacg•u•a |
| 280 | | | AS | u•AcGuAaGgAgAuCcAcC•u•g |
| 218 | MITO-F-siMCJ-56 | | S | L•caagguggAUCuccuuacg•u•a |
| 282 | | | AS | u•AcguAaggagauCcaccu•u•g |

Table 7 provides additional results obtained following synthesis of SEQ ID NOs: 171-282. Column one provides SEQ ID NO assigned to each double-stranded siMCJ RNA conjugated to a GalNAc ligand cluster (see Table 6 for sequences); column two indicates mass calculated; column three indicates mass observed, and column four shows the purity of the synthesized product as determined by LCMS.

| SEQ ID NO | Mass Calculated. | Mass observed | Purity by LCMS |
|---|---|---|---|
| 171 | 8396.04 | 8396.12 | 93.4% |
| 172 | 6856.35 | 6856.46 | |
| 173 | 8419.05 | 8419.44 | 97.1% |
| 174 | 6833.31 | 6833.45 | |
| 175 | 8379.03 | 8379.03 | 95.2% |
| 176 | 6874.35 | 6873.4 | |
| 177 | 8325 | 8324.36 | 91.6% |
| 178 | 6898.95 | 6898.55 | |
| 179 | 8344.86 | 8345.34 | 91.8% |
| 180 | 6892.49 | 6892.64 | |
| 181 | 8348.95 | 8349.09 | 95.5% |
| 182 | 6918.43 | 6918.59 | |
| 183 | 8395.03 | 8395.39 | 97.0% |
| 184 | 6872.35 | 6872.53 | |
| 185 | 8357.98 | 8357.44 | 97.1% |
| 186 | 6880.38 | 6880.88 | |
| 187 | 8372.97 | 8373.46 | 96.7% |
| 188 | 6879.39 | 6879.89 | |
| 189 | 8372.97 | 8373.46 | 96.9% |
| 190 | 6879.39 | 6879.9 | |
| 191 | 8059.82 | 8060.76 | 91.9% |
| 192 | 7154.4 | 7155.35 | |
| 193 | 8700.21 | 8701.41 | 88.9% |
| 194 | 7154.49 | 7455.58 | |
| 195 | 8419.05 | 8419.51 | 97.1% |
| 196 | 6929.6 | 6929.78 | |
| 197 | 8419.05 | 8419.51 | 96.4% |
| 198 | 6906.51 | 6905.77 | |
| 199 | 8419.05 | 8419.5 | 96.9% |
| 200 | 6881.46 | 6881.68 | |
| 201 | 8419.05 | 8419.42 | 96.0% |
| 202 | 6897.52 | 6897.82 | |
| 203 | 7676.57 | 7677.51 | 87.2% |
| 304 | 6873.34 | 6874.45 | |
| 205 | 8379.03 | 8379.96 | 97.9% |
| 206 | 7513.72 | 7514.72 | |
| 207 | 8379.03 | 8379.48 | 97.6% |
| 208 | 6992.66 | 6992.96 | |
| 209 | 8379.03 | 8379.49 | 97.9% |
| 210 | 6968.59 | 6968.85 | |
| 211 | 8379.03 | 8379.48 | 99.1% |
| 212 | 6944.52 | 6944.78 | |
| 213 | 8379.03 | 8379.41 | 96.5% |
| 214 | 6960.59 | 6960.77 | |
| 215 | 8379.03 | 8379.52 | 95.0% |
| 216 | 7561.87 | 7562.06 | |
| 217 | 8379.03 | 8379.59 | 96.3% |
| 218 | 7599.92 | 7600.43 | |
| 219 | 8379.03 | 8379.63 | 96.5% |
| 220 | 6921.48 | 6922.06 | |
| 221 | 8369 | 8367.55 | 95.7% |
| 222 | 6921.48 | 6922.05 | |
| 223 | 8379.03 | 8379.58 | 95.8% |
| 224 | 6937.55 | 6937.98 | |
| 225 | 8355.01 | 8355.52 | 95.1% |
| 226 | 6960.52 | 6961.03 | |
| 227 | 7995.77 | 7996.12 | 99.6% |
| 228 | 6641.31 | 6641.5 | |
| 229 | 8367 | 8367.65 | 98.2% |
| 230 | 7615.99 | 7616.6 | |
| 231 | 8367 | 8367.63 | 99.5% |
| 231 | 6937.55 | 6938.26 | |
| 233 | 8342.97 | 8343.61 | 99.8% |
| 234 | 6976.59 | 6977.26 | |
| 235 | 8339.01 | 8339.52 | 99.0% |
| 236 | 6961.5 | 6961.97 | |
| 237 | 8402.07 | 8402.58 | 81.0% |
| 238 | 6898.44 | 6898.58 | |
| 239 | 8403.06 | 8403.53 | 90.9% |
| 240 | 6882.44 | 6882.9 | |
| 241 | 8403.06 | 8403.49 | 99.5% |
| 242 | 6882.44 | 6882.58 | |
| 243 | 8387.06 | 8387.53 | 87.4% |
| 244 | 6883.43 | 6883.6 | |
| 245 | 8323.99 | 8324.48 | 82.4% |
| 246 | 6946.49 | 6946.99 | |
| 247 | 7637.53 | 7638.54 | 92.6% |
| 248 | 6898.35 | 6899.63 | |
| 249 | 8299.97 | 8300.96 | 98.1% |
| 250 | 6937.39 | 6938.51 | |
| 251 | 8323.99 | 8324.86 | 90.9% |
| 252 | 7537.75 | 7538.75 | |
| 253 | 8299.97 | 8300.45 | 95.1% |
| 254 | 6985.53 | 6985.92 | |
| 255 | 8299.97 | 8300.45 | 93.1% |
| 256 | 7001.6 | 7001.88 | |
| 257 | 8339.99 | 8340.45 | 95.6% |
| 258 | 6945.51 | 6945.65 | |
| 259 | 8287.93 | 8288.45 | 94.8% |
| 260 | 6985.53 | 6986.1 | |
| 261 | 8299.97 | 8300.56 | 96.6% |
| 262 | 6985.53 | 6985.91 | |
| 263 | 7637.53 | 7637.84 | 100.0% |
| 264 | 6306.11 | 6306.32 | |
| 265 | 8287.93 | 8288.53 | 99.8% |
| 266 | 7001 | 7002.28 | |
| 267 | 8310.97 | 8311.57 | 92.8% |
| 268 | 6978.56 | 6978.99 | |
| 269 | 8339.99 | 8340.46 | 99.3% |
| 270 | 6945.51 | 6945.94 | |
| 271 | 8299.97 | 8300.43 | 99.3% |
| 272 | 6985.53 | 6985.98 | |
| 273 | 8075.82 | 8076.81 | 97.4% |
| 274 | 6525.16 | 6526 | |
| 275 | 8012.76 | 8013.85 | 94.3% |
| 276 | 6588.22 | 6589.14 | |
| 277 | 7686.51 | 7687.66 | 92.1% |
| 278 | 6879.39 | 6880.5 | |
| 279 | 8005.72 | 8006.83 | 95.2% |
| 280 | 6610.28 | 6611.47 | |
| 218 | 8348.95 | 8350.32 | 95.2% |
| 282 | 7002.68 | 7003.85 | |

Example 4

In Vivo Testing of Mito-F Conjugated siMCJs in Mice

Mito-F conjugated siMCJs were tested for efficacy knocking down MCJ in mouse liver. Eight-week-old male C57BL/6J mice were used for all the studies. At day 0, each mouse was given a single subcutaneous administration of Mito-F conjugated siMCJs formulated in a pharmaceutically acceptable PBS buffer, or vehicle control (PBS buffer with no RNAi agent). Three mice were used for each group, and total 33 mice were used for this study. At preset dates post dosing (day 7 or 14), mice were sacrificed. Whole liver was collected and quickly flushed with cold saline. Two pieces of liver tissue from the left portion of the middle lobe were cut and sliced to small pieces to a frozen tube. MCJ expression was determined by RT-qPCR normalized with expression level of GAPDH. Knockdown activity was calculated by comparing the MCJ expression in mouse livers of treated group versus the control group. Result is summarized in Table 8 and Table 9.

TABLE 8

Percent knockdown of MCJ expression in mouse liver one week following single subcutaneous injection of Mito-F-siMCJs at 3 mg/kg.

| Number | Percent knockdown of MCJ in mice liver |
|---|---|
| MITO-F-siMCJ-1 | 11% |
| MITO-F-siMCJ-2 | 65% |
| MITO-F-siMCJ-3 | 61% |
| MITO-F-siMCJ-4 | 63% |
| MITO-F-siMCJ-5 | 17% |
| MITO-F-siMCJ-6 | 60% |
| MITO-F-siMCJ-7 | 62% |
| MITO-F-siMCJ-8 | 61% |
| MITO-F-siMCJ-9 | 66% |
| MITO-F-siMCJ-10 | 8% |

TABLE 9

Percent knockdown of MCJ expression in mouse liver two weeks following single subcutaneous injection of Mito-F-siMCJs at 3 mg/kg.

| Number | Percent knockdown of MCJ in mice liver |
|---|---|
| MITO-F-siMCJ-11 | 51% |
| MITO-F-siMCJ-12 | 45% |
| MITO-F-siMCJ-13 | 55% |
| MITO-F-siMCJ-14 | 60% |
| MITO-F-siMCJ-15 | 62% |
| MITO-F-siMCJ-16 | 63% |
| MITO-F-siMCJ-17 | 80% |
| MITO-F-siMCJ-18 | 80% |
| MITO-F-siMCJ-19 | 70% |
| MITO-F-siMCJ-20 | 74% |
| MITO-F-siMCJ-21 | 81% |
| MITO-F-siMCJ-22 | 72% |
| MITO-F-siMCJ-23 | 85% |
| MITO-F-siMCJ-24 | 87% |
| MITO-F-siMCJ-25 | 82% |
| MITO-F-siMCJ-26 | 85% |
| MITO-F-siMCJ-27 | 87% |
| MITO-F-siMCJ-28 | 85% |
| MITO-F-siMCJ-29 | 95% |
| MITO-F-siMCJ-30 | 82% |
| MITO-F-siMCJ-31 | 82% |
| MITO-F-siMCJ-32 | 85% |
| MITO-F-siMCJ-33 | 86% |
| MITO-F-siMCJ-34 | 83% |
| MITO-F-siMCJ-35 | 52% |
| MITO-F-siMCJ-36 | 84% |
| MITO-F-siMCJ-37 | 88% |
| MITO-F-siMCJ-38 | 79% |
| MITO-F-siMCJ-39 | 75% |
| MITO-F-siMCJ-40 | 75% |
| MITO-F-siMCJ-41 | 56% |
| MITO-F-siMCJ-42 | 83% |
| MITO-F-siMCJ-43 | 85% |
| MITO-F-siMCJ-44 | 82% |
| MITO-F-siMCJ-45 | 86% |
| MITO-F-siMCJ-46 | 90% |
| MITO-F-siMCJ-47 | 68% |
| MITO-F-siMCJ-48 | 75% |
| MITO-F-siMCJ-49 | 82% (1.5 mpk)* |
| MITO-F-siMCJ-50 | 77% |
| MITO-F-siMCJ-51 | 88% |
| MITO-F-siMCJ-52 | 62% |
| MITO-F-siMCJ-53 | 36% |
| MITO-F-siMCJ-54 | 14% |
| MITO-F-siMCJ-55 | 57% |
| MITO-F-siMCJ-56 | 61% |

*MITO-F-siMCJ-49 was dosed at 1.5 mg/kg

Example 5

In Vivo Time Course and Dose Response Study of Mito-F-siMCJ-9 in Mice.

To assess the knockdown efficacy and durability, a time course and dose response study in mice with Mito-F-siMCJ-9 was carried out. At day 0, each mouse was given a single subcutaneous administration of Mito-F-siMCJ-9 formulated in a pharmaceutically acceptable PBS buffer, or vehicle control (PBS buffer with no RNAi agent). Three mice were used for each group, and total 27 mice were used for this study. Each group of mice were sacrificed according to the schedule in Table 10. MCJ expression in mouse liver was determined by RT-qPCR normalized with expression level of GAPDH. Knockdown activity was calculated by comparing the MCJ expression in mouse liver of treated group versus the control group (sacrificed at day 14). Result is summarized in Table 10.

TABLE 10

Percent knockdown of MCJ expression in mouse liver following single subcutaneous injection of Mito-F-siMCJ-9.

| Dosage (mpk) | Sacrificed at days post dosing | MCJ % Knockdown | STDV |
|---|---|---|---|
| PBS | 14 | 0% | 0.13 |
| 0.3 | 14 | 19% | 0.04 |
| 1.0 | 14 | 36% | 0.02 |
| 3.0 | 14 | 76% | 0.02 |
| 10.0 | 14 | 92% | 0.01 |
| 50.0 | 14 | 93% | 0.01 |
| 3.0 | 3 | 59% | 0.04 |
| 3.0 | 7 | 68% | 0.04 |
| 3.0 | 21 | 76% | 0.03 |

Example 6

In Vivo Dose Response Study of Mito-F-siMCJ-29, Mito-F-siMCJ-32, Mito-F-siMCJ-46 and Mito-F-siMCJ-48 in Mice.

Dose response study in mice with Mito-F-siMCJ-29, Mito-F-siMCJ-32, Mito-F-siMCJ-46 and Mito-F-siMCJ-48 was carried out. At day 0, each mouse was given a single subcutaneous administration of Mito-F-siMCJ-29, Mito-F-siMCJ-32, Mito-F-siMCJ-46 and Mito-F-siMCJ-48 formulated in a pharmaceutically acceptable PBS buffer, or vehicle control (PBS buffer with no RNAi agent). Three mice were used for each group, and total 39 mice were used for this study. Each group of mice were sacrificed at day 14 (2 weeks post dosing). MCJ expression in mouse liver was determined by RT-qPCR normalized with expression level of GAPDH. Knockdown activity was calculated by comparing the MCJ expression in mouse liver of treated group versus the control group. Result is summarized in Table 11.

TABLE 11

Percent knockdown of MCJ expression in mouse liver two weeks following single subcutaneous injection of Mito-F-siMCJ-29, Mito-F-siMCJ-32, Mito-F-siMCJ-46 and Mito-F-siMCJ-48 at given dosage.

| | Percent Knockdown at dosage | | |
|---|---|---|---|
| Compound | 1 mpk | 3 mpk | 10 mpk |
| MITO-F-siMCJ-29 | 35% | 52% | 77% |
| MITO-F-siMCJ-32 | 64% | 82% | 93% |

TABLE 11-continued

Percent knockdown of MCJ expression in mouse liver two weeks following single subcutaneous injection of Mito-F-siMCJ-29, Mito-F-siMCJ-32, Mito-F-siMCJ-46 and Mito-F-siMCJ-48 at given dosage.

| | Percent Knockdown at dosage | | |
|---|---|---|---|
| Compound | 1 mpk | 3 mpk | 10 mpk |
| MITO-F-siMCJ-46 | 74% | 85% | 91% |
| MITO-F-siMCJ-48 | 76% | 83% | 92% |

Example 7

In Vivo Testing of Mito-F-siMCJ-32 and Mito-F-siMCJ-48 in Cynomolgus Monkeys.

Mito-F-siMCJ-32 and Mito-F-siMCJ-48 were tested in Cynomolgus Monkeys for assessing efficacy of knocking down MCJ expression in monkey liver. Two male Cynomolgus Monkeys were used for testing each of the compounds. On day 0, each monkey was dosed with either Mito-F-siMCJ-32 or Mito-F-siMCJ-48 via subcutaneous injection at 3 mg/kg, formulated in a pharmaceutically acceptable PBS buffer solution. Ultrasound guided liver biopsy using a 16-18 G biopsy needle was conducted with each of animals at 7 days before and 14, 28 and 42 days post-dosing, following an overnight fasting under sedation/anesthesia (Zoletil 50, 3-5 mg/kg IM). One piece of liver tissue sample (5 to 10 mg) was collected from each of animals. The collected liver biopsy samples were weighed and immediately placed in 1 ml RNAlater™ and then stored at 4° C. overnight. All excess RNAlater™ was removed by aspirating or blotting tissue on laboratory wipes and liver tissues were stored at −80° C. until analysis. MCJ expression was determined by qPCR normalized with GAPDH expression. Knockdown activity was calculated by comparing MCJ expression in liver samples from the same monkey pre-treatment and at each of the time points post dosing. Result is summarized in Table 12.

TABLE 12

Percent knockdown of MCJ expression in cynomolgus monkey liver following a single subcutaneous injection of Mito-F-siMCJ-32 and Mito-F-siMCJ-48 at 3 mg/kg.

| | | Percent Knockdown of MCJ | | |
|---|---|---|---|---|
| Compound | Monkey | Day 14 | Day 28 | Day 42 |
| MITO-F-siMCJ-32 | Monkey1 | 49% | 53% | 51% |
| | Monkey2 | 46% | 70% | 66% |
| MITO-F-siMCJ-48 | Monkey3 | 37% | 66% | 61% |
| | Monkey4 | 64% | 78% | 74% |

Example 8

In Vivo Testing of siMCJs in Mouse Kidney siMCJs [sense strand: 5'-c•a•ccucUaGAAcaaguuau•c•a-3' (SEQ ID NO: 265); antisense strand: 5'-u•G•auaAcUUguucUaGagg•u•g-3' (SEQ ID NOP: 266)] not conjugated to GalNAc are tested for efficacy knocking down MCJ in mouse kidney. Eight-week-old male C57BL/6J mice are used in these experiments. At day 0, each mouse is given a single intravenous administration of siMCJs formulated in a pharmaceutically acceptable PBS buffer, or vehicle control (PBS buffer with no RNAi agent). Three doses are tested (1, 3 and 10 mg/Kg). Three mice are included in each group, and total 33 mice are used for this study. At preset dates post dosing (day 3, 7 or 14), mice are sacrificed. Whole kidney is collected and quickly flushed with cold saline. Two pieces of kidney tissue are cut and sliced to small pieces in a frozen tube. MCJ expression is determined by Western blot analysis and normalized with expression level of GAPDH, and real time RT-PCR and normalized with expression levels of GAPDH. Knockdown activity is calculated by comparing the MCJ expression in mouse kidney of treated group versus the control group. Result shows knockdown of MCJ expression resulting from the administered siMCJs.

Results show siMCJ shown to be effective to reducer MCJ polypeptide activity when administered conjugated to GalNAc for delivery to liver reduced MCJ polypeptide activity in kidney when administered without conjugation to GalNAc. Total kidney is used, and siMCJ is identified predominantly (but not exclusively) by the proximal tubule cells in the kidney where MCJ is more predominantly expressed.

EQUIVALENTS

Although several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto; the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified, unless clearly indicated to the contrary.

All references, patents and patent applications and publications that are cited or referred to in this application are incorporated herein in their entirety herein by reference.

The invention claimed is:

1. A double-stranded ribonucleic acid (dsRNA) agent for inhibiting expression of methylation-controlled J-protein (MCJ), wherein the dsRNA agent comprises a sense strand corresponding to SEQ ID NO: 43 and an antisense strand corresponding to SEQ ID NO: 44, optionally comprising a targeting ligand.

2. The dsRNA agent of claim 1, wherein the dsRNA agent comprises at least one modified nucleotide.

3. The dsRNA agent of claim 1, wherein the dsRNA agent comprises at least one phosphorothioate internucleoside linkage.

4. The dsRNA agent of claim 1, wherein the nucleotides of the sense strand and the antisense strand are modified nucleotides.

5. The dsRNA agent of claim 1, wherein the dsRNA agent comprises at least one modified nucleotide and further comprises one or more targeting groups or linking groups.

6. The dsRNA agent of claim 5, wherein the one or more targeting groups or linking groups are conjugated to the sense strand.

7. The dsRNA agent of claim 5, wherein the one or more targeting groups or linking groups comprises N-acetyl-galactosamine (GalNAc).

8. The dsRNA agent of claim 7, wherein the GalNAc is targeting ligand Mito-F.

9. The dsRNA agent of claim 1, wherein the dsRNA agent comprises a targeting group that is conjugated to the 5'-terminal end of the sense strand.

10. The dsRNA agent of claim 1, wherein the dsRNA agent has two blunt ends.

11. The dsRNA agent of claim 1, wherein at least one of the sense strand and the antisense strand comprises a 3' overhang of 1 to 6 nucleotides.

12. The dsRNA agent of claim 1, wherein at least one of the sense strand and the antisense strand comprises a 3' overhang of 2 to 6 nucleotides.

13. A composition comprising the dsRNA agent of claim 1, optionally further comprising a pharmaceutically acceptable carrier, and optionally further comprising one or more additional therapeutic agents.

14. A method of inhibiting the expression of a methylation-controlled J-protein (MCJ) gene in a cell, the method comprising preparing a cell comprising an effective amount of the dsRNA agent of claim 1 to inhibit expression of the MCJ gene in the cell.

15. The method of claim 14, wherein the dsRNA agent comprises at least one modified nucleotide.

* * * * *